(12) United States Patent
Hu et al.

(10) Patent No.: US 12,319,725 B2
(45) Date of Patent: *Jun. 3, 2025

(54) IL-2 MUTANT AND APPLICATION THEREOF

(71) Applicant: HAINAN SIMCERE PHARMACEUTICAL CO., LTD., Haikou (CN)

(72) Inventors: Yingying Hu, Shanghai (CN); Zhuoxiao Cao, Shanghai (CN); Renhong Tang, Jiangsu (CN); Hu Ge, Shangai (CN); Yayuan Fu, Shanghai (CN); Jinsheng Ren, Jiangsu (CN)

(73) Assignee: HAINAN SIMCERE PHARMACEUTICAL CO., LTD., Haikou (CN)

( * ) Notice: Subject to any disclaimer, the term of this patent is extended or adjusted under 35 U.S.C. 154(b) by 47 days.

This patent is subject to a terminal disclaimer.

(21) Appl. No.: 18/626,591

(22) Filed: Apr. 4, 2024

(65) Prior Publication Data

US 2024/0247041 A1    Jul. 25, 2024

Related U.S. Application Data

(63) Continuation of application No. 18/390,606, filed on Dec. 20, 2023, now abandoned, which is a continuation of application No. 18/024,151, filed as application No. PCT/CN2021/116463 on Sep. 3, 2021.

(30) Foreign Application Priority Data

Sep. 4, 2020 (CN) .......................... 202010918842.0
Aug. 13, 2021 (CN) .......................... 202110932286.7

(51) Int. Cl.
C07K 14/55 (2006.01)
A61P 37/02 (2006.01)
C12N 15/63 (2006.01)

(52) U.S. Cl.
CPC .............. *C07K 14/55* (2013.01); *A61P 37/02* (2018.01); *C12N 15/63* (2013.01); *C07K 2319/31* (2013.01)

(58) Field of Classification Search
CPC .................................................... C07K 14/55
See application file for complete search history.

(56) References Cited

U.S. PATENT DOCUMENTS

2005/0142106 A1    6/2005  Wittrup et al.
2023/0265148 A1    8/2023  Hu et al.

FOREIGN PATENT DOCUMENTS

| CN | 1442427 A | 9/2003 |
|---|---|---|
| CN | 102665754 A | 9/2012 |
| CN | 104231068 A | 12/2014 |
| CN | 110642934 A | 1/2020 |
| TW | I687435 B | 3/2020 |
| WO | 2014023679 A1 | 2/2014 |
| WO | 2019028425 A1 | 2/2019 |
| WO | 2019173832 A2 | 9/2019 |
| WO | 2020069398 A1 | 4/2020 |
| WO | 2020125743 A1 | 6/2020 |

OTHER PUBLICATIONS

Mei, L., et al., "Site-Mutation of Hydrophobic Core Residues Synchronically Poise Super Interleukin 2 for Signaling: Identifying Distant Structural Effects through Affordable Computations," Int. J. Mol. Sci., 19(916): 1-23 (2008).
Ghelani, A., et al., "Defining the Threshold IL-2 Signal Required for Induction of Selective Treg Cell Responses Using Engineered IL-2 Muteins," Frontiers in Immunology, 11(1106): 1-19 (2020).
Rao, B.M., et al., "Interleukin-2 mutants with enhanced a-receptor subunit binding affinity," Protein Engineering, 16(12): 1081-1087 (2003).
Levin, A.M., et al., "Exploiting a natural conformational switch to engineer an Interleukin-2 superkine," Nature, 484 (7395): 529-533 (2012).
Emerson, S.D., et al., "NMR characterization of interleukin-2 in complexes with the IL-2Ra receptor component, and with low molecular weight compounds that inhibit the IL-2/IL-Ra interaction," Protein Science, 12: 811-822 (2003).
Office Action from Taiwan Application No. 110132852 dated Feb. 21, 2024.
Office Action from Eurasian Application No. 202390721 dated Mar. 26, 2024.
Office Action from Japanese Application No. 2023-515158 dated Apr. 23, 2024.
Silva, DA. et al. (2019). De novo design of potent and selective mimics of IL-2 and IL-15. Nature. 565: 186-191.
Office Action from Chilean Application No. 202300631 dated Dec. 23, 2024.
Search Report from Chilean Application No. 202300631 dated Dec. 23, 2024.

*Primary Examiner* — Prema M Mertz
(74) *Attorney, Agent, or Firm* — Harness Dickey & Pierce P.L.C.

(57) ABSTRACT

The present disclosure discloses IL-2 mutants and uses thereof. More specifically, the disclosure provides IL-2 mutants and corresponding fusion proteins, conjugates, nucleic acid fragments, vectors, host cells, methods for preparing the mutants or fusion proteins, IL-2 mutants or fusion proteins prepared according to the methods, pharmaceutical compositions, pharmaceutical uses, methods for treating diseases, and methods for preferentially stimulating regulatory T cells. Compared to wild-type IL-2, the IL-2 mutants of the present disclosure have higher Tm values and improved stability; alternatively, the IL-2 mutants of the present disclosure have an increased yield or changed binding activity to the IL-2Rβγ complexes compared to wild-type IL-2.

16 Claims, 22 Drawing Sheets

Specification includes a Sequence Listing.

IL-2 MUTANT AND APPLICATION THEREOF

CROSS-REFERENCE TO RELATED PATENT APPLICATIONS

This patent application is a continuation of U.S. patent application Ser. No. 18/390,606 filed on 20 Dec. 2023 which is a continuation of U.S. patent application Ser. No. 18/024,151 filed on 1 Mar. 2023, which is a national stage application under 35 U.S.C. § 371 of PCT International Application No. PCT/CN2021/116463, which has an international filing date of 3 Sep. 2021 and claims priority under 35 U.S.C. § 119 to Chinese Patent Application No. 202110932286.7 filed on 13 Aug. 2021 and Chinese Patent Application No. 202010918842.0 filed on 4 Sep. 2020. The contents of each application recited above are incorporated herein by reference in their entirety.

REFERENCE TO AN ELECTRONIC SEQUENCE LISTING

This application contains references to amino acid sequences and/or nucleic acid sequences which have been submitted concurrently herewith as the sequence listing .xml file entitled "ST26_SL_20_Dec_2023.xml", file size 68 KiloBytes (KB), created on 20 Dec. 2023. The aforementioned sequence listing is hereby incorporated by reference in its entirety.

TECHNICAL FIELD

The disclosure relates to the field of biomedicine, in particular to IL-2 mutants and uses thereof.

BACKGROUND

Interleukin-2 (IL-2), initially identified as a T cell growth factor (TCGF), has been found to bind to its receptors and activate the proliferation and activation of immune cells such as T cells and NK cells in subsequent studies.

IL-2 receptors include IL-2R α subunit (CD25), IL-2R β subunit (CD122) and IL-2R γ subunit (CD132). Different subunits can form receptor complexes with different affinity, including high affinity receptor IL-2R αβγ, intermediate affinity receptor IL-2R βγ and low affinity receptor IL-2R α or IL-2R αβ. Different cells express different types of IL-2R subunits. For example, traditional T cells (CD4$^+$ T and CD8$^+$ T) in their resting state generally express on cell surface IL-2 receptor β (IL-2R β, CD122) and IL-2 receptor γ (IL-2R γ, CD132), but hardly express IL-2 α receptor (IL-2R α, CD25). However, in addition to IL-2R β and IL-2R γ, IL-2R α is constitutively highly expressed in regulatory T cells (Tregs).

At present, researchers are trying to use IL-2 or its mutants to activate immune cells or a subset of immune cells to treat tumors or autoimmune diseases. For example, high doses of IL-2 have been approved for the treatment of malignant melanoma or metastatic renal cell carcinoma, and a PEG-IL-2 conjugate, NKTR-358, has been approved for clinical trials of autoimmune diseases.

Therefore, it is of great significance for development of IL-2 drugs to improve the stability and yield of IL-2 and/or change its binding ability to certain receptor complexes. In view of this, the present disclosure is proposed.

SUMMARY

The present disclosure provides IL-2 mutants, fusion proteins, conjugates, nucleic acid fragments, vectors, host cells, methods for preparing the mutants or fusion proteins, IL-2 mutants or fusion proteins prepared according to the methods, pharmaceutical compositions, pharmaceutical uses, therapeutic methods, and methods for preferentially stimulating regulatory T cells.

In a first aspect, the disclosure provides an IL-2 mutant comprising one or more mutation(s) at Q13, L18, G27, Y31, A73, H79, P82, I89, N90, V91, V93, F117 or R120 compared to wild-type IL-2.

In some specific embodiments, the mutation is deletion, insertion or substitution, preferably substitution.

In some specific embodiments, the IL-2 mutant comprises one or more mutation(s) of Q13L, L18I, G27W, Y31V, A73L, H79Q, P82L, I89L, N90Y, V91A, V93I, F117W or R120F.

In some specific embodiments, the IL-2 mutant comprises at least one group of mutation(s) in groups (a)-(h):
(a). mutations at Y31/A73/H79; preferably, Y31V/A73L/H79Q;
(b). a mutation at Q13; preferably, Q13L;
(c). a mutation at R120; preferably, R120F;
(d). mutations at L18/V91/F117; preferably, L18I/V91A/F117W;
(e). mutations at L18/I89/V93; preferably, L18I/I89L/V93I;
(f). mutations at G27/R120; preferably, G27W/R120F;
(g). mutations at P82/R120; preferably, P82L/R120F;
(h). mutations at N90/R120; preferably, N90Y/R120F.

In some specific embodiments, the IL-2 mutant has an amino acid sequence as shown in any one of SEQ ID NOs: 2 to 9.

In some specific embodiments, the IL-2 mutant has a Tm value higher than that of the wild-type IL-2.

In some specific embodiments, the wild-type IL-2 has an amino acid sequence as shown in SEQ ID NO: 60 or SEQ ID NO: 1.

In some specific embodiments, the IL-2 mutant further comprises one or more mutation(s) selected from the group consisting of mutation at H16, D20, N88, V91 or Q126, e.g., H16E, D20A, D20H, D20Y, N88A, N88I, N88G, N88R, N88D, V91R, V91K, Q126L or Q126F.

Preferably, the IL-2 mutant further comprises at least one group of mutation(s) selected from groups (i)-(iv):
(i). a mutation at H16; preferably, H16E;
(ii). a mutation at D20; preferably, D20A;
(iii). a mutation at V91; preferably V91R;
(iv). mutations at H16/V91; preferably, H16E/V91R.

In some specific embodiments, the IL-2 mutant comprises at least one group of mutation(s) in groups (a)-(n):
(a). mutations at H16/Y31/A73/H79; preferably, H16E/Y31V/A73L/H79Q;
(b). mutations at H16/R120; preferably, H16E/R120F;
(c). mutations at H16/L18/V91/F117; preferably, H16E/L18I/V91A/F117W;
(d). mutations at H16/L18/I89/V93; preferably, H16E/L18I/I89L/V93I;
(e). mutations at H16/G27/R120; preferably, H16E/G27W/R120F;
(f). mutations at H16/P82/R120; preferably, H16E/P82L/R120F;
(g). mutations at D20/Y31/A73/H79; preferably, D20A/Y31V/A73L/H79Q;
(h). mutations at D20/R120; preferably, D20A/R120F;
(i). mutations at V91/Y31/A73/H79; preferably, V91R/Y31V/A73L/H79Q;
(j). mutations at V91/Q13; preferably, V91R/Q13L;
(k). mutations at V91/R120; preferably, V91R/R120F;

(l). mutations at V91/L18/I89/V93; preferably, V91R/L18I/I89L/V93I;

(m). mutations at H16/V91/Y31/A73/H79; preferably, H16E/V91R/Y31V/A73L/H79Q;

(n). mutations at H16/V91/L18/I89/V93, preferably, H16E/V91R/L18I/I89L/V93I.

In some specific embodiments, the IL-2 mutant has an amino acid sequence as shown in any one of SEQ ID NOs: 22 to 27, SEQ ID NOs:29 to 30, SEQ ID NOs:32 to 35 or SEQ ID NOs:37 to 38.

In some specific embodiments, the IL-2 mutant further comprises one or more mutation(s) selected from the group consisting of mutation at N26, N29, N30, N71, Q11, L132, L70, P82, G27 or F28.

Preferably, the IL-2 mutant further comprises one or more mutation(s) selected from the group consisting of N26Q, N29S, N30S, N71Q, Q11C, L132C, L70C, P82C, G27C or F78C. More preferably, the IL-2 mutant further comprises at least one group of mutation(s) in groups (a)-(g):
(a). N26Q;
(b). N29S;
(c). N30S;
(d). N71Q;
(e). Q11C/L132C;
(f). L70C/P82C;
(g). G27C/F78C.

In some specific embodiments, the IL-2 mutant further comprises one or more mutation(s) selected from the group consisting of mutation at F42, Y45 or L72, preferably, F42A, Y45A or L72G.

In some specific embodiments, the IL-2 mutant has a reduced binding ability to IL-2Rβγ subunit complex compared to the wild-type IL-2; preferably, the binding ability $_{IL-2R\beta\gamma\ subunit\ complex}$/binding ability $_{IL-2\ \alpha\beta\gamma\ subunit\ complex}$ decreases.

In some specific embodiments, the mutant has a reduced stimulation ability to non-regulatory T cells or NK (natural killer) cells compared to the wild-type IL-2; the stimulation can be selected from intracellular STAT5 phosphorylation or cell proliferation.

In some specific embodiments, the mutant preferentially stimulates regulatory T cells (Tregs) in peripheral blood or T cell population compared to non-regulatory T cells or NK (natural killer) cells; said preferentially stimulating can be selected from preferentially stimulating STAT5 phosphorylation in regulatory T cells, preferentially stimulating regulatory T cell proliferation, increasing regulatory T cells to non-regulatory T cells ratio, or increasing regulatory T cells to NK cells ratio.

In a second aspect, the disclosure provides an IL-2 mutant comprising one or more mutation(s) at H16, D20 or V91 compared to wild-type IL-2; preferably, the IL-2 mutant comprises at least one group of mutation(s) selected from the groups (i)-(iv):
(i). a mutation at H16; preferably, H16E;
(ii). a mutation at D20; preferably, D20A;
(iii) a mutation at V91; preferably V91R;
(iv). mutations at H16/V91; preferably, H16E/V91R.

In some specific embodiments, the IL-2 mutant has an amino acid sequence as shown in SEQ ID NOs: 21, 28, 31 or 36.

In some specific embodiments, the IL-2 mutant further comprises one or more mutation(s) selected from the group consisting of mutation at N26, N29, N30, N71, Q11, L132, L70, P82, G27 or F28.

Preferably, the IL-2 mutant further comprises one or more mutations selected from the group consisting of N26Q, N29S, N30S, N71Q, Q11C, L132C, L70C, P82C, G27C or F78C.

More preferably, the IL-2 mutant further comprises at least one group of mutation(s) in groups (a)-(g):
(a). N26Q;
(b). N29S;
(c). N30S;
(d). N71Q;
(e). Q11C/L132C;
(f). L70C/P82C;
(g). G27C/F78C.

In some specific embodiments, the IL-2 mutant has a reduced binding ability to IL-2R βγ subunit complex compared to the wild-type IL-2; preferably, the binding ability $_{IL-2R\beta\gamma\ subunit\ complex}$/binding ability $_{IL-2\alpha\beta\gamma\ subunit\ complex}$ decreases.

In some specific embodiments, the mutant has reduced stimulation ability to non-regulatory T cells or NK (natural killer) cells compared to the wild-type IL-2, and the stimulation can be selected from intracellular STAT5 phosphorylation or cell proliferation.

In some specific embodiments, the mutant preferentially stimulates regulatory T cells (Tregs) in peripheral blood or T cell population compared to non-regulatory T cells or NK cells; said preferentially stimulating can be selected from preferentially stimulating STAT5 phosphorylation in regulatory T cells, preferentially stimulating regulatory T cell proliferation, increasing regulatory T cells to non-regulatory T cells ratio, or increasing regulatory T cells to NK cells ratio.

In some specific embodiments, the mutation comprises deletion, insertion or substitution, preferably substitution.

In some specific embodiments, the wild-type IL-2 has an amino acid sequence as shown in SEQ ID NO: 60 or SEQ ID NO: 1.

In a third aspect, the present disclosure provides a fusion protein comprising a first polypeptide and a second polypeptide, wherein the first polypeptide is the IL-2 mutant as described above and the second polypeptide is a non-IL-2 polypeptide.

In some specific embodiments, the second polypeptide is an Fc, a tumor-antigen-binding molecule or an IL-2 receptor subunit;

optionally, the Fc is a human IgG Fc, for example a human IgG1 Fc;

preferably, the human IgG1 Fc comprises at least one group of mutation(s) selected from the groups (a)-(i):
(a). C220S;
(b). N297G;
(c). C220S and N297G;
(d). A327Q;
(e). L234A and L235A;
(f). A287C and L306C;
(g). A259C and L306C;
(h). R292C and V302C;
(i). V323C and I332C;

more preferably, the human IgG1 Fc has an amino acid sequence as shown in SEQ ID NO: 11;

optionally, the tumor antigen comprises EDB-FN (extra domain of fibronectin), Muc1, p53, FAP, GD2, EpCAM, tenascin-C, CD20, CEA, MAdCAM-1 or WT1 (Wilms Tumor Protein 1);

optionally, the tumor-antigen-binding molecule is an antibody, such as scFv, sdFv, Fab, Fab', F(ab')$_2$ or Fv;

optionally, the IL-2 receptor subunit is an IL-2 receptor α subunit.

In some specific embodiments, C-terminus of the first polypeptide is linked to N-terminus of the second polypeptide with or without a linker; or N-terminus of the first polypeptide is linked to C-terminus of the second polypeptide with or without a linker;

preferably, the linker is selected from: $(G_4S)_n$, $(GGNGT)_n$ or $(YGNGT)_n$, and the n is selected from 1, 2, 3, 4 or 5;

more preferably, the C-terminus of the first polypeptide is linked to the N-terminus of the second polypeptide by a linker $(G_4S)_3$.

In some specific embodiments, the fusion protein comprises an amino acid sequence as shown in any one of SEQ ID NOs: 13 to 20 or SEQ ID NOs: 39 to 56.

In a fourth aspect, the present disclosure provides a conjugate comprising the mutant or the fusion protein as described above, and further comprising a stabilizer, drug or tracer molecule conjugated to the mutant or fusion protein; wherein the stabilizer can be selected from polyethylene glycol, such as monomethoxy polyethylene glycol.

In a fifth aspect, the present disclosure provides an isolated nucleic acid fragment encoding the mutant or the fusion protein as described above.

In a sixth aspect, the present disclosure provides a vector comprising the nucleic acid fragment as described above.

In a seventh aspect, the present disclosure provides a host cell comprising the vector as described above.

In some specific embodiments, the host cell is a prokaryotic cell or a eukaryotic cell; the prokaryotic cell or the eukaryotic cell can be selected from *Escherichia coli*, yeast, insect cells or mammalian cells, and the mammalian cells can be selected from a CHO cell line or a HEK293 cell line.

In an eighth aspect, the present disclosure provides a method for preparing the mutant or the fusion protein as described above, wherein the method comprises culturing the aforementioned host cell and isolating the IL-2 mutant or fusion protein expressed by the host cell.

In a ninth aspect, the present disclosure provides an IL-2 mutant or fusion protein prepared according to the aforementioned method.

In a tenth aspect, the present disclosure provides a pharmaceutical composition comprising the aforementioned mutant, fusion protein, conjugate, nucleic acid fragment, vector or host cell; and a pharmaceutically acceptable carrier, diluent or adjuvant;

preferably, the pharmaceutical composition is a pharmaceutical composition for injection, e.g. for intravenous or subcutaneous injection; more preferably, the pharmaceutical composition per dose comprises an effective amount of fusion protein to be administrated to a subject; most preferably, the effective amount is 0.001-10 mpk, such as 0.001 mpk, 0.002 mpk, 0.003 mpk, 0.004 mpk, 0.005 mpk, 0.006 mpk, 0.007 mpk, 0.008 mpk, 0.009 mpk, 0.01 mpk, 0.02 mpk, 0.03 mpk, 0.04 mpk, 0.05 mpk, 0.06 mpk, 0.07 mpk, 0.08 mpk, 0.09 mpk, 0.1 mpk, 0.2 mpk, 0.3 mpk, 0.4 mpk, 0.5 mpk, 0.6 mpk, 0.7 mpk, 0.8 mpk, 0.9 mpk, 1 mpk, 2 mpk, 3 mpk, 4 mpk, 5 mpk, 6 mpk, 7 mpk, 8 mpk, 9 mpk or 10 mpk.

In an eleventh aspect, the present disclosure provides use of the aforementioned mutant, fusion protein, conjugate, nucleic acid fragment, vector or host cell in the manufacture of a medicament for treating disease;

preferably, the medicament is a medicament for injection, e.g., for intravenous or subcutaneous injection;

preferably, the medicament per dose comprises an effective amount of fusion protein to be administrated to a subject; most preferably, the effective amount is 0.001-10 mpk, such as 0.001 mpk, 0.002 mpk, 0.003 mpk, 0.004 mpk, 0.005 mpk, 0.006 mpk, 0.007 mpk, 0.008 mpk, 0.009 mpk, 0.01 mpk, 0.02 mpk, 0.03 mpk, 0.04 mpk, 0.05 mpk, 0.06 mpk, 0.07 mpk, 0.08 mpk, 0.09 mpk, 0.1 mpk, 0.2 mpk, 0.3 mpk, 0.4 mpk, 0.5 mpk, 0.6 mpk, 0.7 mpk, 0.8 mpk, 0.9 mpk, 1 mpk, 2 mpk, 3 mpk, 4 mpk, 5 mpk, 6 mpk, 7 mpk, 8 mpk, 9 mpk or 10 mpk;

preferably, the medicament is used for treating an autoimmune disease, proliferative disease, or viral infection;

more preferably, the autoimmune disease comprises rheumatoid arthritis, ankylosing spondylitis, systemic lupus erythematosus, cutaneous lupus erythematosus, lupus nephritis, IgA nephropathy, Sjogren's syndrome, polymyositis, dermatomyositis, scleroderma, psoriasis, plaque psoriasis, alopecia areata, multiple sclerosis, amyotrophic lateral sclerosis, inflammatory bowel disease, ulcerative colitis, Crohn's disease, graft-versus-host disease, organ transplant rejection, autoimmune hepatitis, type I diabetes, autoimmune vasculitis, eczema or asthma;

more preferably, the proliferative disease comprises neoplasm, solid tumor, hematological tumor, malignant ascites or malignant pleural effusion; wherein the solid tumor can be benign or malignant, primary or metastatic, the malignant solid tumor can be a cancer or a sarcoma, for example, epithelial cell carcinoma, endothelial cell carcinoma, squamous cell carcinoma, teratoma, lung tumor, papillomavirus-induced cancer, adenocarcinoma, carcinoma, melanoma, angiosarcoma, neuroblastoma, metastatic lung cancer, non-small cell lung cancer, small cell lung cancer, breast cancer, Merkel cell cancer, ovarian cancer, renal cell cancer, metastatic renal cancer, head and neck cancer, bladder cancer, non-muscle invasive bladder cancer; the hematological tumor can be leukemia, lymphoma, multiple myeloma, such as B-cell lymphoma, T-cell lymphoma, cutaneous T-cell lymphoma, T-cell large granular lymphocytic leukemia;

more preferably, the viral infection is selected from HIV infection, novel coronavirus infection or HPV viral infection.

In a twelfth aspect, the present disclosure provides a method for treating an autoimmune disease, proliferative disease, or viral infection, wherein the method comprises a step of administering to a subject an effective amount of the aforementioned IL-2 mutant, fusion protein, conjugate, nucleic acid fragment, vector, host cell or pharmaceutical composition;

preferably, the step of administering is performed via injection, e.g. intravenous or subcutaneous injection;

preferably, the effective amount is 0.001-10 mpk, such as 0.001 mpk, 0.002 mpk, 0.003 mpk, 0.004 mpk, 0.005 mpk, 0.006 mpk, 0.007 mpk, 0.008 mpk, 0.009 mpk, 0.01 mpk, 0.02 mpk, 0.03 mpk, 0.04 mpk, 0.05 mpk, 0.06 mpk, 0.07 mpk, 0.08 mpk, 0.09 mpk, 0.1 mpk, 0.2 mpk, 0.3 mpk, 0.4 mpk, 0.5 mpk, 0.6 mpk, 0.7 mpk, 0.8 mpk, 0.9 mpk, 1 mpk, 2 mpk, 3 mpk, 4 mpk, 5 mpk, 6 mpk, 7 mpk, 8 mpk, 9 mpk or 10 mpk;

preferably, the autoimmune disease comprises rheumatoid arthritis, ankylosing spondylitis, systemic lupus erythematosus, cutaneous lupus erythematosus, lupus nephritis, IgA nephropathy, Sjogren's syndrome, polymyositis, dermatomyositis, scleroderma, psoriasis, plaque psoriasis, alopecia areata, multiple sclerosis, amyotrophic lateral sclerosis, inflammatory bowel disease, ulcerative colitis, Crohn's disease, graft-versus-host disease, organ transplant rejection, autoimmune hepatitis, type I diabetes, autoimmune vasculitis, eczema or asthma;

preferably, the proliferative disease comprises neoplasm, solid tumor, hematological tumor, malignant ascites or malignant pleural effusion; wherein the solid tumor is optionally selected from benign or malignant, primary or metastatic, the malignant solid tumor is optionally selected from a cancer or a sarcoma, for example, epithelial cell carcinoma, endothelial cell carcinoma, squamous cell carcinoma, teratoma, lung tumor, papillomavirus-induced cancer, adenocarcinoma, carcinoma, melanoma, angiosarcoma, neuroblastoma, metastatic lung cancer, non-small cell lung cancer, small cell lung cancer, breast cancer, Merkel cell cancer, ovarian cancer, renal cell cancer, metastatic renal cancer, head and neck cancer, bladder cancer, non-muscle invasive bladder cancer; the hematological tumor is optionally selected from selected from leukemia, lymphoma, multiple myeloma, such as B-cell lymphoma, T-cell lymphoma, cutaneous T-cell lymphoma, T-cell large granular lymphocytic leukemia;

more preferably, the viral infection is selected from HIV infection, novel coronavirus infection or HPV viral infection.

In a thirteenth aspect, the present disclosure provides a method for preferentially stimulating a T cell population or regulatory T cells in peripheral blood, wherein the method comprises a step of contacting the T cell population or peripheral blood with the aforementioned IL-2 mutant, fusion protein, conjugate, nucleic acid fragment, vector, host cell, or pharmaceutical composition;

preferably, said preferential stimulating comprises:
(a) preferentially stimulating STAT5 phosphorylation of regulatory T cells compared to non-regulatory T cells or NK cells;
(b) preferentially stimulating proliferation of regulatory T cells compared to non-regulatory T cells or NK cells; and/or
(c) increasing regulatory T cells to non-regulatory T cells ratio, or increasing regulatory T cells to NK cells ratio.

Terms and Definitions

Unless otherwise defined in the present disclosure, the scientific and technical terms related to the present disclosure shall have the meanings commonly understood by those skilled in the art.

As used herein, unless otherwise stated, the term "IL2" or "IL-2" refers to any natural or recombinant IL-2 derived from any vertebrates, including mammals such as primates (e.g., human) and rodents (e.g., mice and rats) and domesticated or farm mammals. The "IL2" or "IL-2" in the present disclosure includes any form ranging from unprocessed IL-2 (e.g., IL-2 comprising a signal peptide at N-terminus) to mature IL-2 in a cell. The "IL2" or "IL-2" in the present disclosure also includes natural variants and fragments of IL-2, such as splice variants or allelic variants. The "IL2" or "IL-2" as used herein also includes non-naturally occurring mutants, such as IL-2 mutants artificially modified by genetic engineering.

The term "wild-type IL-2" is the same as the IL-2 mutant, except that each amino acid at the mutation positions of the IL-2 mutant is maintained as wild-type amino acid. For example, if the IL-2 mutant is an unprocessed IL-2, then the wild-type form of the mutant is an unprocessed IL-2; if the IL-2 mutant is a mature IL-2, then the wild-type form of the mutant is a mature IL-2; if the IL-2 mutant is a truncated form of IL-2, then the wild-type form of the mutant is the corresponding truncated form of IL-2 with a wild-type sequence. As an example, the "wild-type IL-2" in the present disclosure may have an amino acid sequence as follow:

APTSSSTKKTQLQLEHLLLDLQMILNGINNYKNPK-LTRMLTFKFYMPKKATELKHL QCLEEELKPLEEVLN-LAQSKNFHLRPRDLISNINVIVLELKGSETTFMCEYA-DETATIVEFL NRWITFXQSIISTLT (SEQ ID NO: 60); wherein the 125th amino acid residue "X" represents C, S, A or V.

As used herein, the term "mutation" comprises amino acid substitution, deletion, insertion, or any combination thereof. The "mutation" in the present disclosure may be generated by genetic or chemical methods known in the art, including, but not limited to, site-directed mutagenesis, PCR, gene synthesis, and the like.

The numbering of "mutation site" of an IL-2 mutant starts from the first amino acid residue (A) of the "wild-type IL-2" as shown in SEQ ID NO: 60. As an example, the "Q13 mutation" refers to mutation of the amino acid residue (Gln, Q) at position 13 of the wild-type IL-2 as shown in SEQ ID NO: 60. For example, the "Q13L mutation" refers to an IL-2 mutant in which the amino acid Q (Gln) at position 13 of the wild-type IL-2 as shown in SEQ ID NO: 60 is mutated to L (Leu).

As used herein, the punctuation "/" used between mutation sites means "and", which indicates that the mutations before and after "/" coexist in the same IL-2 mutant at the same time. For example, "Y31/A73/H79" means that mutations occur simultaneously at Y31, A73 and H79 in the same IL-2 mutant, and "Y31V/A73L/H79Q" means that Y31V, A73L and H79Q coexist in the same IL-2 mutant at the same time.

As used herein, the term "Tm" (melting temperature) refers to a temperature at which 50% of protein is denatured. The "Tm" in present disclosure may be determined by any methods well known in the art. For example, the Tm value of protein can be determined by the method shown in example 3 or 6 of the present disclosure.

The term "fusion protein" in the present disclosure refers to a protein product obtained by connecting the coding regions of two or more genes by genetic recombination, chemical or other suitable methods, and expressing the protein product obtained by genetic recombination under the control of the same regulatory sequence. In the fusion protein of the present disclosure, the coding regions of two or more genes can be fused at one or several positions by the sequence encoding linker(s). Linker(s) can be used to construct the fusion protein of the present disclosure.

As used herein, the term "linker" refers to a peptide used to link IL-2 to another protein molecule or protein fragment to ensure the correct folding and stability of protein. Said another molecule includes, but is not limited to, Fc. Preferably, the "linker" in the disclosure is $(GGGGS)_n$, wherein n may be 0, 1, 2, 3, 4 or 5. If a linker sequence is too short, it may affect the folding of higher-order structure of two proteins, so that the two proteins interfere with each other. If a linker sequence is too long, it may involve immunogenicity, because the linker sequence itself is a new antigen.

As used herein, the term "second polypeptide" may be a single-chain polypeptide, such as scFv antibody. The "second polypeptide" also includes a multi-chain polypeptide, wherein at least one polypeptide chain is fused to IL-2 or a mutant thereof, and the other polypeptide chain(s) is or are linked to the at least one polypeptide chain as fused by covalent or non-covalent bond(s). For example, for Fab antibody, the heavy chain of Fab can be fused to IL-2 or a mutant thereof, and the light chain is linked to the heavy chain by disulfide bond(s).

As used herein, the term "Fc" refers to the constant region of an immunoglobulin chain, in particular the carboxyl terminus of the constant region of an immunoglobulin heavy chains or a part thereof. Fc has no antigen-binding activity and is the region where the antibodies interact with effector molecules or cells. "Fc" as used herein may be any Fc or a variant thereof, which is derived from human or non-human mammals. For example, an immunoglobulin Fc may comprise a combination of two or more domains (CH1, CH2, CH3 or CH4) of heavy chains and an immunoglobulin hinge region. Fc can be derived from different species, preferably derived from human immunoglobulin. According to the amino acid sequence of the constant region of heavy chains, immunoglobulin can be divided into different classes, mainly including five classes of immunoglobulins: IgA, IgD, IgE, IgG and IgM. Some of them can be further divided into subclasses (isotypes), such as IgG-1, IgG-2, IgG-3 and IgG-4; IgA-1 and IgA-2. Preferably, "Fc" comprises at least one immunoglobulin hinge region, as well as the CH2 and CH3 domains of the IgG. More preferably, "Fc" comprises a CH2 domain, a CH3 domain and an immunoglobulin hinge region of IgG1, and the starting amino acid position of the hinge region can be varied. Unless otherwise stated, the amino acid residues of the Fc, constant region or antibody of the present disclosure are numbered according to the EU numbering system, also known as EU index, as described in Kabat et al., Sequences of Proteins of Immunological Interest, 5th Edition, Public Health Service, National Institutions of Health, Bethesda, Md., 1991.

The "antibody" of the present disclosure is used in the broadest sense and encompasses various antibody structures, including but not limited to monoclonal antibodies, polyclonal antibodies, multispecific antibodies (e.g., bispecific antibodies) and antigen-binding fragments, as long as they exhibit the desired antigen-binding activity. The antibodies may include murine antibodies, human antibodies, humanized antibodies, chimeric antibodies and camel antibodies. Illustratively, the antibody can be an immunoglobulin, which is a tetrapeptide chain structure composed of two identical heavy chains and two identical light chains connected by interchain disulfide bonds. The immunoglobulin heavy chain constant regions are different in terms of amino acid composition and sequence, and thus antigenicity. Therefore, immunoglobulin can be divided into five classes, or isotypes of immunoglobulin, namely IgM, IgD, IgG, IgA and IgE, and their corresponding heavy chains are μ chain, δ chain, γ chain, α chain and ε chain respectively. According to the difference of amino acid composition in the hinge region and the number and position of heavy chain disulfide bonds, the same class of Ig can be divided into different subclasses, for example, IgG can be divided into IgG1, IgG2, IgG3 and IgG4. Light chains may be divided into κ chains or λ chains according to the difference of the constant region. Each of the five classes of Ig can have κ chains or λ chains. The "antibody" in present disclosure also includes scFv, sdFv, Fab, Fab', F(ab')$_2$ and Fv.

As used herein, the term "isolated" refers to removal of a material from its original or natural environment (e. g., the natural environment in which it naturally exists). Therefore, the natural polynucleotides or polypeptides present in living animals are not isolated, but the same polynucleotides or polypeptides isolated from some or all coexisting materials in the natural system by human intervention are isolated.

An "isolated nucleic acid fragment" is an RNA or DNA polymer, which is single-stranded or double-stranded, and optionally contains synthetic, unnatural or altered nucleotide bases. The isolated nucleic acid fragment in the form of a DNA polymer may consist of one or more cDNAs, genomic DNAs, or synthetic DNA fragments. The "nucleic acid fragment" of the present disclosure may be a part of a vector and integrated into a host cell chromosome at a heterologous site. The "nucleic acid fragment" of the present disclosure may be a part of a composition. Since such vector or composition is not a part of its natural environment, it is still isolated.

As used herein, the term "vector" includes a nucleic acid vector, such as a DNA vector (e. g., a plasmid), an RNA vector, a virus or other suitable replicon (e.g., a viral vector). Various vectors have been developed to deliver polynucleotides for encoding foreign proteins into prokaryotic or eukaryotic cells. The "vector" of the present disclosure may contain additional sequence elements for expressing proteins and/or integrating these polynucleotide sequences into the genome of mammalian cells, regulatory sequences (such as promoter and enhancer regions) for directing gene transcription, or sequences for enhancing the translation rate of genes or improving the stability or nuclear export of mRNA produced by gene transcription. The sequence elements include, for example, 5' and 3' untranslated regions, internal ribosomal entry sites (IRES) and polyadenylation signal sites in order to direct efficient transcription of genes carried on expression vectors. The "vector" of the present disclosure may further comprise a polynucleotide encoding a marker for selecting cells containing such a vector. Examples of suitable markers include genes encoding antibiotic resistance, such as ampicillin, chloramphenicol, kanamycin or nourseothricin.

As used herein, the term "host cell" refers to a cell into which an exogenous nucleic acid has been introduced, including progeny of such a cell. The "progeny" may have exactly the same nucleic acid content as their parent, or may contain mutations and is not exactly the same as the parent cell. The "progeny" includes mutant progeny that have the same function or biological activity as the function or biological activity screened or selected in the original transformed cells. As used herein, the term "pharmaceutical composition" refers to a mixture containing one or more of IL-2 mutants, fusion proteins, nucleic acid fragments, vectors or host cells of the present disclosure. The mixture further comprises other components, including but not limited to, pharmaceutically acceptable carriers, diluents or adjuvants thereof. The purpose of the pharmaceutical composition of the disclosure is to facilitate the administration of drugs to organisms, which promotes the absorption of active ingredients to exert their biological activity.

The term "treatment" of the present disclosure refers to a surgical or pharmaceutical treatment, the purpose of which is to prevent, or mitigate (reduce) the progression of undesirable physiological changes or lesions, such as cell proliferative disorders (e.g., cancers or infectious diseases), autoimmune diseases (e.g., systemic lupus erythematosus) in subjects in need of treatment. Beneficial or desired clinical results include, but are not limited to, relief of symptoms, alleviation of disease severity, stabilization (i.e., no deterioration) of the disease state, delay or slowdown of disease progression, improvement or mitigation of disease status, and remission (whether partial or complete), whether detectable or undetectable. The subjects in need of treatment include those who suffer from diseases or disorders, those who are susceptible to diseases or disorders or those who intend to prevent diseases or disorders. When the terms "alleviation", "reduction", "mitigation", "amelioration" and "remission" are used, it also means elimination, disappearance, non-occurrence, and the like.

As used herein, the term "subject" refers to an organism receiving treatment for specific diseases or disorders (such as cancers or infectious diseases or autoimmune diseases) as described herein. Examples of subjects and patients include mammals, such as humans, primates, pigs, goats, rabbits, hamsters, cats, dogs, guinea pigs, cattle or other members of bovine family, sheep and horses, receiving treatment for diseases or disorders.

As used herein, the term "effective amount" refers to an amount of a therapeutic agent that is effective in preventing or alleviating symptoms or progression of a disease, when the therapeutic agent is administered to a cell, tissue or subject, alone or in combination with another therapeutic agent. The "effective amount" also refers to an amount of a compound that is sufficient to relieve symptoms (such as, to treat, cure, prevent or relieve related medical conditions), or increase the rate of treating, curing, preventing or relieving those conditions. When an active ingredient is administered to an individual alone, the therapeutically effective amount refers solely to the active ingredient. When a combination is administrated, the therapeutically effective amount refers to the combined amount of active ingredients that have a therapeutic effect, whether they are administered in combination, continuously or simultaneously.

The term "autoimmune disease" of the present disclosure refers to a condition characterized by damage to cells, tissues and/or organs caused by the immune response of a subject to its own cells, tissues and/or organs. As an example, autoimmune diseases include but are not limited to rheumatoid arthritis, ankylosing spondylitis, systemic lupus erythematosus, cutaneous lupus erythematosus, lupus nephritis, IgA nephropathy, Sjogren's syndrome, polymyositis, dermatomyositis, scleroderma, psoriasis, plaque psoriasis, alopecia areata, multiple sclerosis, amyotrophic lateral sclerosis, inflammatory bowel disease, ulcerative colitis, Crohn's disease, graft-versus-host disease, organ transplant rejection, autoimmune hepatitis, type I diabetes, autoimmune vasculitis, eczema or asthma.

The term "proliferative disease" of the present disclosure refers to a condition in which the growth of cells or tissues is out of control and/or abnormal, which may lead to the development of undesired conditions or diseases. It may or may not be cancerous, including but not limited to neoplasms, solid tumors, hematological tumors, malignant ascites or malignant pleural effusion. The "solid tumor" of the present disclosure can be benign or malignant, primary or metastatic; and malignant solid tumors can be carcinomas or sarcomas. As an example, the "solid tumor" of the present disclosure includes, but is not limited to, epithelial cell carcinoma, endothelial cell carcinoma, squamous cell carcinoma, teratoma, lung tumor, papillomavirus-induced cancer, adenocarcinoma, carcinoma, melanoma, angiosarcoma, neuroblastoma, metastatic lung cancer, non-small cell lung cancer, small cell lung cancer, breast cancer, Merkel cell cancer, ovarian cancer, renal cell cancer, metastatic renal cancer, head and neck cancer, bladder cancer, non-muscle invasive bladder cancer. As an example, the "hematological tumor" of the present disclosure includes, but is not limited to, leukemia, lymphoma, multiple myeloma, such as B-cell lymphoma, T-cell lymphoma, cutaneous T-cell lymphoma, T-cell large granular lymphocytic leukemia.

As used herein, the term "IL-2 receptor α subunit" (IL-2Rα), also known as "CD25", refers to any natural IL-2 receptor α subunits or mutants thereof derived from any vertebrates, including mammals such as primates (e.g., humans) and rodents (e.g., mice and rats). The "IL-2 receptor α subunit" includes "full-length" unprocessed IL-2 receptor α subunits, any form of processed IL-2 receptor α subunits derived from cells, naturally occurring IL-2 receptor α subunit variants (such as splice variants or allelic variants), and artificially engineered mutants on the basis of natural IL-2 receptor α subunits. In certain embodiments, the IL-2 receptor α subunit is a human IL-2 receptor β subunit with an exemplary sequence as shown in SEQ ID NO: 57.

As used herein, the term "IL-2 receptor β subunit" (IL-2Rβ), also known as "CD122", refers to any natural IL-2 receptor β subunits or mutants thereof derived from any vertebrates, including mammals such as primates (e.g., humans) and rodents (e.g., mice and rats), The IL-2 receptor β subunit includes "full-length" unprocessed IL-2 receptor β subunits, any form of processed IL-2 receptor β subunits derived from cells, naturally occurring IL-2 receptor β subunit variants (such as splice variants or allelic variants), and artificially engineered mutants on the basis of natural IL-2 receptor β subunits. In certain embodiments, the IL-2 receptor β subunit is a human IL-2 receptor β subunit with an exemplary sequence as shown in SEQ ID NO: 58.

As used herein, the term "IL-2 receptor γ subunit" (IL-2Rγ), also known as "CD132", refers to any natural IL-2 receptor γ subunits or mutants thereof derived from any vertebrates, including mammals such as primates (e.g., humans) and rodents (e.g., mice and rats), The IL-2 receptor γ subunit includes "full-length" unprocessed IL-2 receptor γ subunits, any form of processed IL-2 receptor γ subunits derived from cells, naturally occurring IL-2 receptor γ subunit variants (such as splice variants or allelic variants), and artificially engineered mutants on the basis of natural IL-2 receptor γ subunits. In certain embodiments, the IL-2 receptor γ subunit is a human IL-2 receptor γ subunit with an exemplary sequence as shown in SEQ ID NO: 59.

As used herein, the term "Treg", also known as "regulatory T cell" or "$T_{regulatory\ cell}$", refers to a specialized CD4$^+$ T cell type which can inhibit the response of other T cells. Treg is characterized by expressing IL-2 receptor α subunit (CD25) and transcription factor Forkhead box protein P3 (FOXP3), and plays a key role in inducing and maintaining peripheral autologous tolerance to antigens. Treg needs IL-2 to perform its function, develop and induce its inhibitory characteristics.

As used herein, the term "binding ability" refers to the binding or interaction exhibited between paired molecules. The common paired molecules include ligand and receptor, antigen and antibody, enzyme and substrate, etc., more specifically, for example, IL2 and IL-2Rβγ subunit complex, or IL-2 and IL-2Rαβγ subunit complex. The "binding ability" of the present disclosure can be detected by conventional methods in the art, including but not limited to ELISA or FACS.

DESCRIPTION OF THE FIGURES

FIG. 3A shows the expression level of human IL-2 receptor β protein;

FIG. 3B shows the expression level of human IL-2 receptor γ protein;

FIG. 4A shows the expression level of human IL-2 receptor α protein;

FIG. 4B shows the expression level of human IL-2 receptor β protein;

FIG. 4C shows the expression level of human IL-2 receptor γ protein;

FIG. 5A shows the binding activity of mut7.36-linker2-hFc, mut11.08-linker2-hFc, mut61-linker2-hFc, mut61.08-linker2-hFc or mut61.46-linker2-hFc to CHO-K1 IL-2 receptor αβγ recombinant cells;

FIG. 5B shows the binding activity of mut11.31-linker2-hFc or mut7.66-linker2-hFc to CHO-K1 IL-2 receptor αβγ recombinant cells;

FIG. 5C shows the binding activity of mut7.36-linker2-hFc, mut11.08-linker2-hFc, mut61-linker2-hFc, mut61.08-linker2-hFc or mut61.46-linker2-hFc to CHO-K1 IL-2 receptor βγ recombinant cells;

FIG. 5D shows the binding activity of mut11.31-linker2-hFc or mut7.66-linker2-hFc to CHO-K1 IL-2 receptor βγ recombinant cells.

FIG. 6A shows the effect of mut7.36-linker2-hFc on the level of STAT5 phosphorylation in Tregs;

FIG. 6B shows the effect of mut11.08-linker2-hFc on the level of STAT5 phosphorylation in Tregs;

FIG. 6C shows the effect of mut11.31-linker2-hFc or mut7.66-linker2-hFc on the level of STAT5 phosphorylation in Tregs;

FIG. 6D shows the effect of mut7.36-linker2-hFc on the level of phosphorylation in $CD4^+CD25^-FoxP3^-$T cells;

FIG. 6E shows the effect of mut11.08-linker2-hFc on the level of phosphorylation in $CD4^+CD25^-FoxP3^-$T cells;

FIG. 6F shows the effect of mut11.31-linker2-hFc or mut7.66-linker2-hFc on the level of phosphorylation in $CD4^+CD25^-FoxP3^-$T cells;

FIG. 6G shows the effect of mut7.36-linker2-hFc on the level of phosphorylation in $CD8^+$ T cells;

FIG. 6H shows the effect of mut11.08-linker2-hFc on the level of phosphorylation in $CD8^+$ T cells;

FIG. 6I shows the effect of mut11.31-linker2-hFc or mut7.66-linker2-hFc on the level of phosphorylation in $CD8^+$ T cells;

FIG. 7A shows the effect of mut7.36-linker2-hFc or mut7.66-linker2-hFc on the level of proliferation of Tregs;

FIG. 7B shows the effect of mut11.08-linker2-hFc or mut11.31-linker2-hFc on the level of proliferation of Tregs;

FIG. 7C shows the effect of mut7.36-linker2-hFc or mut7.66-linker2-hFc on the level of proliferation of $CD4^+$ $CD25^-FoxP3^-$T cells;

FIG. 7D shows the effect of mut11.08-linker2-hFc or mut11.31-linker2-hFc on the level of proliferation of $CD4^+$ $CD25^-FoxP3^-$T cells;

FIG. 7E shows the effect of mut7.36-linker2-hFc or mut7.66-linker2-hFc on the level of proliferation of $CD8^+$ $CD25^-$T cells;

FIG. 7F shows the effect of mut11.08-linker2-hFc or mut11.31-linker2-hFc on the level of proliferation of $CD8^+$ $CD25^-$T cells;

DETAILED DESCRIPTION

Figure 1:
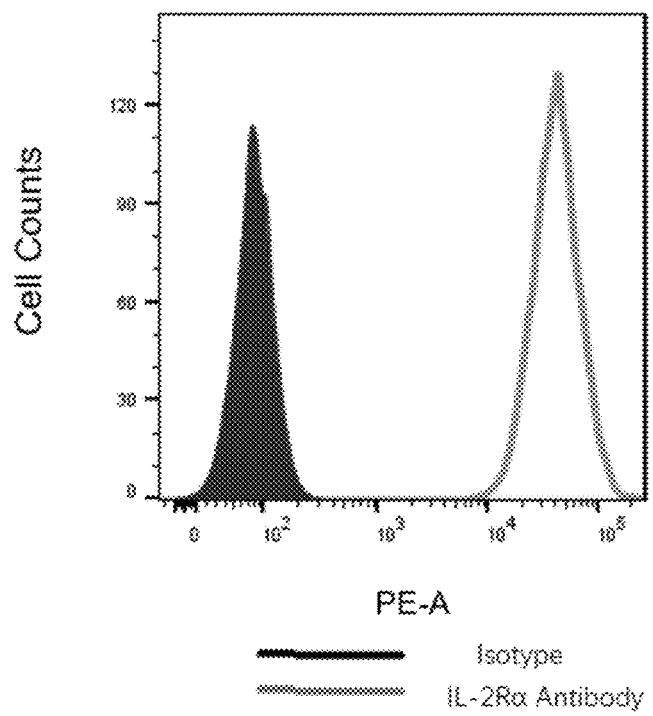
FIG. 1 shows the expression level of human IL-2 receptor α protein in the CHO-K1 hIL-2-Rα recombinant cell line (clone 1A6) detected by flow cytometry (FACS), wherein the IL-2 receptor α antibody is purchased from BioLegend; and the negative control refers to isotype control.

The present disclosure will be further described below with reference to specific examples. The advantages and features of the present disclosure will become clear with the description. If specific conditions are not indicated in the examples, the conventional conditions or the conditions suggested by the manufacturer shall be followed. If the manufacturer is not indicated, the reagents or instruments used are conventional products that can be purchased commercially.

The following examples of this disclosure are merely exemplary and not intended to limit the scope of the present disclosure. It should be understood by those skilled in the art that the details and forms of the technical solution of the present disclosure can be modified or substituted without departing from or exceeding the spirit or scope of the disclosure, and such modifications and substitutions all fall within the protection scope of the present disclosure.

Example 1—Design of IL-2 Mutants with Improved Thermal Stability and Construction of Expression Plasmid Various algorithms were used to obtain IL-2 mutants with improved thermal stability, and corresponding sequences were designed and synthesized. The nucleic acid fragments encoding wild-type IL-2 and the aforementioned IL-2 mutants were cloned into a pTT5 vector with an Fc tag, and then the plasmids encoding the following fusion proteins were prepared according to established standard methods in molecular biology: IL-2-linker2-hFc, mut0.08-linker2-hFc, mut0.31-linker2-hFc, mut0.36-linker2-hFc, mut0.39-linker2-hFc, mut0.46-linker2-hFc, mut0.57-linker2-hFc, mut0.66-linker2-hFc and mut0.68-linker2-hFc.

The specific sequences of the aforementioned fusion proteins and components are shown in Table 1, wherein "IL-2" represents the wild-type IL-2, and "mutXX" represents IL-2 mutants in which mutation occurs compared to wild-type IL-2.

TABLE 1

Sequences of IL-2 mutants with improved stability

| Mutant | SEQ ID NO | Sequence information |
|---|---|---|
| IL2 | SEQ ID NO: 1 | APTSSSTKKTQLQLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLT |
| mut0.08 (Y31V/A73L/H79Q) | SEQ ID NO: 2 | APTSSSTKKTQLQLEHLLLDLQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLT |
| mut0.31 (Q13L) | SEQ ID NO: 3 | APTSSSTKKTQLLLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLT |
| mut0.36 (R120F) | SEQ ID NO: 4 | APTSSSTKKTQLQLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLT |
| mut0.39 (L18I/V91A/F117W) | SEQ ID NO: 5 | APTSSSTKKTQLQLEHILDLQMILNGINNYKNPKLTRMLTFKFYMPK KATELKHLQCLEEELKPLEEVLNLAQSKNFHLRPRDLISNINAIVLELK GSETTFMCEYADETATIVEWLNRWITFAQSIISTLT |
| mut0.46 (L18I/I89L/V93I) | SEQ ID NO: 6 | APTSSSTKKTQLQLEHILDLQMILNGINNYKNPKLTRMLTFKFYMPK KATELKHLQCLEEELKPLEEVLNLAQSKNFHLRPRDLISNLNVIILELK GSETTFMCEYADETATIVEFLNRWITFAQSIISTLT |
| mut0.57 (G27W/R120F) | SEQ ID NO: 7 | APTSSSTKKTQLQLEHLLLDLQMILNWINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLT |
| mut0.66 (P82L/R120F) | SEQ ID NO: 8 | APTSSSTKKTQLQLEHLLLDLQMILNGINNYKNPKLTRMLTFKFYMPK KATELKHLQCLEEELKPLEEVLNLAQSKNFHLRLRDLISNINVIVLELK GSETTFMCEYADETATIVEFLNFWITFAQSIISTLT |

TABLE 1-continued

Sequences of IL-2 mutants with improved stability

| Mutant | SEQ ID NO | Sequence information |
|---|---|---|
| mut0.68 (N90Y/R120F) | SEQ ID NO: 9 | APTSSSTKKTQLQLEHLLLDLQMILNGINNYKNPKLTRMLTFKFYMPK KATELKHLQCLEEELKPLEEVLNLAQSKNFHLRPRDLISNIYVIVLELK GSETTFMCEYADETATIVEFLNFWITFAQSIISTLT |
| linker2 | SEQ ID NO: 10 | GGGGSGGGGSGGGGS |
| hFc (C220S/N297G) | SEQ ID NO: 11 | EPKSSDKTHTCPPCPAPELLGGPSVFLFPPKPKDTLMISRTPEVTCVVV DVSHEDPEVKFNWYVDGVEVHNAKTKPREEQYGSTYRVVSVLTVLH QDWLNGKEYKCKVSNKALPAPIEKTISKAKGQPREPQVYTLPPSRDEL TKNQVSLTCLVKGFYPSDIAVEWESNGQPENNYKTTPPVLDSDGSFFL YSKLTVDKSRWQQGNVFSCSVMHEALHNHYTQKSLSLSPGK |
| IL2-linker2-hFc, also known as WT IL-2-linker2-hFc (C220S/N297G) | SEQ ID NO: 12 | APTSSSTKKTQLQLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.08-linker2-hFc (Y31V/A73L/H79Q) | SEQ ID NO: 13 | APTSSSTKKTQLQLEHLLLDLQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.31-linker2-hFc (Q13L) | SEQ ID NO: 14 | APTSSSTKKTQLLLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.36-linker2-hFc (R120F) | SEQ ID NO: 15 | APTSSSTKKTQLQLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.39-linker2-hFc (L18I/V91A/F117W) | SEQ ID NO: 16 | APTSSSTKKTQLQLEHLILDLQMILNGINNYKNPKLTRMLTFKFYMPK KATELKHLQCLEEELKPLEEVLNLAQSKNFHLRPRDLISNINAIVLELK GSETTFMCEYADETATIVEWLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.46-linker2-hFc (L18I/I89L/V93I) | SEQ ID NO: 17 | APTSSSTKKTQLQLEHLILDLQMILNGINNYKNPKLTRMLTFKFYMPK KATELKHLQCLEEELKPLEEVLNLAQSKNFHLRPRDLISNLNVIILELK GSETTFMCEYADETATIVEFLNRWITFAQSIISTLTGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.57-linker2-hFc (G27W/R120F) | SEQ ID NO: 18 | APTSSSTKKTQLQLEHLLLDLQMILNWINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |

TABLE 1-continued

Sequences of IL-2 mutants with improved stability

| Mutant | SEQ ID NO | Sequence information |
|---|---|---|
| mut0.66-linker2-hFc (P82L/R120F) | SEQ ID NO: 19 | APTSSSTKKTQLQLEHLLLDLQMILNGINNYKNPKLTRMLTFKFYMPK KATELKHLQCLEEELKPLEEVLNLAQSKNFHLRLRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.68-linker2-hFc (N90Y/R120F) | SEQ ID NO: 20 | APTSSSTKKTQLQLEHLLLDLQMILNGINNYKNPKLTRMLTFKFYMPK KATELKHLQCLEEELKPLEEVLNLAQSKNFHLRPRDLISNIYVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |

Example 2—Production and Purification of IL-2 Mutants with Improved Thermal Stability HEK293 cells (purchased from the Cell Bank of the Chinese Academy of Sciences) were transiently transfected (PEI, Polysciences) with the plasmids constructed in Example 1 and then expanded at 37° C. in FreeStyle™ 293 Expression Medium (purchased from Gibco). After 7 days, the cell culture medium was collected, and the cell components were removed by centrifugation to obtain the culture supernatant containing IL-2-hFc fusion proteins.

The fusion proteins in the cell culture supernatant were purified using a 10 mL protein A column (purchased from Bestchrom). The protein A column was first equilibrated with 3 to 5 column volumes of an equilibrium buffer (PBS phosphate buffer, pH 7.4), and then loaded with the clear culture supernatant at a flow rate of 10 mL/min. After loading, the protein A column was washed with 3 to 5 column volumes of the equilibrium buffer. The proteins bound to the protein A column were eluted with an eluent buffer (0.02 M citric acid buffer, 0.1 M glycine, 0.1 M sodium chloride, pH 3.0), and the elution was monitored by a nucleic acid/protein detector (A280 ultraviolet absorption peak). The eluted proteins were collected and neutralized with the added buffer (1 M arginine, 0.4 M succinic acid, pH 9.0). The target proteins were then collected through a molecular sieve (purchased from Bestchrom) with a buffer system (20 mM PB, 200 mM sodium chloride, pH 6.0-6.5). The purified IL-2 mutant fusion proteins were obtained by aseptic filtration with a 0.22 μm filter and preserved in sterile condition.

The purified IL-2 mutant fusion proteins were tested and analyzed for protein yield, concentration (A280/1.4) and SEC purity. The purified IL-2 mutant fusion proteins with improved thermal stability (mutXX-linker2-hFc) were qualified, and had a significantly higher yield compared to wild-type IL-2 (IL2-linker2-hFc). The results of protein yield, concentration and purity are shown in Table 2

TABLE 2

Detection results of IL-2 mutant fusion proteins with improved thermal stability

| Mutant | Protein yield (mg/L) | Protein SEC purity | Protein concentration (mg/ml) |
|---|---|---|---|
| IL-2-linker2-hFc | 0.95 | 97.25% | 1.11 |
| mut0.08-linker2-hFc | 8.95 | 99.85% | 1.79 |
| mut0.31-linker2-hFc | 1.54 | 98.49% | 2.20 |
| mut0.36-linker2-hFc | 2.98 | 99.99% | 1.49 |
| mut0.39-linker2-hFc | 43.10 | 99.58% | 2.13 |
| mut0.46-linker2-hFc | 13.82 | 99.92% | 1.22 |
| mut0.57-linker2-hFc | 1.25 | 99.91% | 0.89 |
| mut0.66-linker2-hFc | 7.39 | 99.90% | 1.12 |
| mut0.68-linker2-hFc | 11.90 | 99.99% | 1.19 |

Example 3—Differential Scanning Fluorimetry (DSF) Assay of IL-2 Mutants with Improved Thermal Stability The buffer in Protein Thermal Shift Dye Kit (purchased from Applied Biosystems, Cat. No. 4461146) diluted to 50 times, the IL-2 mutant proteins (purified by the method described in Example 2) diluted to 0.5 mg/mL, and the dye diluted to 2 times were added to a 20 μL reaction system. After being mixed evenly, the mixture was added into 8-tube strips with 2 duplicate tubes for each sample. The tubes were covered, centrifuged for 5-10 seconds, and analyzed by the Applied Biosystems 7500. The Tm values were then obtained by using Boltzmann method to analyze the melting curve. As shown in Table 3, compared to wild-type IL-2 (IL2-linker2-hFc), the IL-2 mutants (mutXX-linker2-hFc) had increased Tm values by more than 3° C., and thus had significantly improved thermal stability.

TABLE 3

DSF assay results of IL-2 mutants with improved thermal stability

| Mutant | Tm (° C.) |
|---|---|
| IL-2-linker2-hFc | 46.74 |
| mut0.08-linker2-hFc | 54.91 |

TABLE 3-continued

DSF assay results of IL-2 mutants with improved thermal stability

| Mutant | Tm (° C.) |
|---|---|
| mut0.31-linker2-hFc | 57.53 |
| mut0.36-linker2-hFc | 56.59 |
| mut0.39-linker2-hFc | 55.93 |
| mut0.46-linker2-hFc | 53.83 |
| mut0.57-linker2-hFc | 57.98 |
| mut0.66-linker2-hFc | 57.24 |
| mut0.68-linker2-hFc | 54.77 |

Example 4—Design of IL-2 Mutants (IL-2 Mutants with Decreased Binding Ability to βγ Subunits and IL-2 Mutants with Decreased Binding Ability to βγ Subunits and with Improved Thermal Stability) and Construction of Expression Plasmid Various algorithms including MOE software were used to simulate the interaction interface between human IL-2 and corresponding receptor α, β, and γ subunits to obtain mutation sites having decreased binding ability to βγ subunits. The IL-2 mutant sequences with mutation sites having decreased binding activities to βγ subunits were designed and synthesized, together with the IL-2 mutant sequences with a combination of such mutation sites with mutation sites having improved thermal stability. The nucleic acid fragments encoding wild-type IL-2 and the aforementioned IL-2 mutants were cloned into a pTT5 vector with an Fc tag, and then the plasmids encoding the following fusion proteins were prepared according to established standard methods in molecular biology: IL-2-linker2-hFc, mut7-linker2-hFc, mut7.08-linker2-hFc, mut7.36-linker2-hFc, mut7.39-linker2-hFc, mut7.46-linker2-hFc, mut7.57-linker2-hFc, mut7.66-linker2-hFc, mut8-linker2-hFc, mut8.08-linker2-hFc, mut8.36-linker2-hFc, mut11-linker2-hFc, mut11.08-linker2-hFc, mut11.31-linker2-hFc, mut11.36-linker2-hFc, mut11.46-linker2-hFc, mut61-linker2-hFc, mut61.08-linker2-hFc and mut61.46-linker2-hFc. The specific sequences of the fusion proteins and components thereof are shown in Table 4, where "IL-2" represents wild-type IL-2 and "mutXX" represents IL-2 mutants in which mutation occurs compared to the wild-type IL-2.

TABLE 4

Sequences of IL-2 mutants

| Mutant | SEQ ID NO | Sequence information |
|---|---|---|
| IL2 | SEQ ID NO: 1 | Shown in Table 1 |
| mut7 (H16E) | SEQ ID NO: 21 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNRWITFAQSIISTLT |
| mut7.08 (H16E/Y31V/A73L/H79Q) | SEQ ID NO: 22 | APTSSSTKKTQLQLEELLLDLQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLT |
| mut7.36 (H16E/R120F) | SEQ ID NO: 23 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNFWITFAQSIISTLT |
| mut7.39 (H16E/L18I/V91A/F117W) | SEQ ID NO: 24 | APTSSSTKKTQLQLEELILDLQMILNGINNYKNPKLTRMLTFKFYMP KKATELKHLQCLEEELKPLEEVLNLAQSKNFHLRPRDLISNINAIVL ELKGSETTFMCEYADETATIVEWLNRWITFAQSIISTLT |
| mut7.46 (H16E/L18I/I89L/V93I) | SEQ ID NO: 25 | APTSSSTKKTQLQLEELILDLQMILNGINNYKNPKLTRMLTFKFYMP KKATELKHLQCLEEELKPLEEVLNLAQSKNFHLRPRDLISNLNVIIL ELKGSETTFMCEYADETATIVEFLNRWITFAQSIISTLT |
| mut7.57 (H16E/G27W/R120F) | SEQ ID NO: 26 | APTSSSTKKTQLQLEELLLDLQMILNWINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLT |
| mut7.66 (H16E/P82L/R120F) | SEQ ID NO: 27 | APTSSSTKKTQLQLEELLLDLQMILNGINNYKNPKLTRMLTFKFYM PKKATELKHLQCLEEELKPLEEVLNLAQSKNFHLRLRDLISNINVIV LELKGSETTFMCEYADETATIVEFLNFWITFAQSIISTLT |
| mut8 (D20A) | SEQ ID NO: 28 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLT |
| mut8.08 (D20A/Y31V/A73L/H79Q) | SEQ ID NO: 29 | APTSSSTKKTQLQLEHLLLALQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLT |
| mut8.36 (D20A/R120F) | SEQ ID NO: 30 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLT |
| mut11 (V91R) | SEQ ID NO: 31 | APTSSSTKKTQLQLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLT |

TABLE 4-continued

Sequences of IL-2 mutants

| Mutant | SEQ ID NO | Sequence information |
|---|---|---|
| mut11.08 (V91R/Y31V/A73L/H79Q) | SEQ ID NO: 32 | APTSSSTKKTQLQLEHLLLDLQMILNGINNVKNPKLTRMLTFKFYM PKKATELKHLQCLEEELKPLEEVLNLLQSKNFQLRPRDLISNINRIV LELKGSETTFMCEYADETATIVEFLNRWITFAQSIISTLT |
| mut11.31 (V91R/Q13L) | SEQ ID NO: 33 | APTSSSTKKTQLLLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLT |
| mut11.36 (V91R/R120F) | SEQ ID NO: 34 | APTSSSTKKTQLQLEHLLLDLQMILNGINNYKNPKLTRMLTFKFYMPK KATELKHLQCLEEELKPLEEVLNLAQSKNFHLRPRDLISNINRIVLELK GSETTFMCEYADETATIVEFLNFWITFAQSIISTLT |
| mut11.46 (V91R/L18I/I89L/V93I) | SEQ ID NO: 35 | APTSSSTKKTQLQLEHLILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLT |
| mut61 (H16E/V91R) | SEQ ID NO: 36 | APTSSSTKKTQLQLEELLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLT |
| mut61.08 (H16E/V91R/Y31V/A73L/H79Q) | SEQ ID NO: 37 | APTSSSTKKTQLQLEELLLDLQMILNGINNYKNPKLTRMLTFKFYM PKKATELKHLQCLEEELKPLEEVLNLLQSKNFQLRPRDLISNINRIV LELKGSETTFMCEYADETATIVEFLNRWITFAQSIISTLT |
| mut61.46 (H16E/V91R/L18I/I89L/V93I) | SEQ ID NO: 38 | APTSSSTKKTQLQLEELILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLT |
| linker2 | SEQ ID NO: 10 | Shown in Table 1 |
| hFc (C220S/N297G) | SEQ ID NO: 11 | Shown in Table 1 |
| IL2-linker2-hFc | SEQ ID NO: 12 | Shown in Table 1 |
| mut7-linker2-hFc (H16E) | SEQ ID NO: 39 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNRWITFAQSIISTLTGGGGSGG GGSGGGGSEPKSSDKTHTCPPCPAPELLGGPSVFLFPPKPKDTLMISRT PEVTCVVVDVSHEDPEVKFNWYVDGVEVHNAKTKPREEQYGSTYRV VSVLTVLHQDWLNGKEYKCKVSNKALPAPIEKTISKAKGQPREPQVYT LPPSRDELTKNQVSLTCLVKGFYPSDIAVEWESNGQPENNYKTTPPVL DSDGSFFLYSKLTVDKSRWQQGNVFSCSVMHEALHNHYTQKSLSLSP GK |
| mut7.08-linker2-hFc (H16E/Y31V/A73L/H79Q) | SEQ ID NO: 40 | APTSSSTKKTQLQLEELLLDLQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTCV VVDVSHEDPEVKFNWYVDGVEVHNAKTKPREEQYGSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| mut7.36-linker2-hFc (H16E/R120F) | SEQ ID NO: 41 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNFWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut7.39-linker2-hFc (H16E/L18I/V91A/F117W) | SEQ ID NO: 42 | APTSSSTKKTQLQLEELILDLQMILNGINNYKNPKLTRMLTFKFYMP KKATELKHLQCLEEELKPLEEVLNLAQSKNFHLRPRDLISNINAIVL ELKGSETTFMCEYADETATIVEWLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP |

TABLE 4-continued

Sequences of IL-2 mutants

| Mutant | SEQ ID NO | Sequence information |
|---|---|---|
| | | REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut7.46-linker2-hFc (H16E/L18I/I89L/V93I) | SEQ ID NO: 43 | APTSSSTKKTQLQLEELILDLQMILNGINNYKNPKLTRMLTFKFYMP KKATELKHLQCLEEELKPLEEVLNLAQSKNFHLRPRDLISNLNVIIL ELKGSETTFMCEYADETATIVEFLNRWITFAQSIISTLTGGGGSGGG GSGGGGSEPKSSDKTHTCPPCPAPELLGGPSVFLFPPKPKDTLMISR TPEVTCVVVDVSHEDPEVKFNWYVDGVEVHNAKTKPREEQYGST YRVVSVLTVLHQDWLNGKEYKCKVSNKALPAPIEKTISKAKGQPR EPQVYTLPPSRDELTKNQVSLTCLVKGFYPSDIAVEWESNGQPENN YKTTPPVLDSDGSFFLYSKLTVDKSRWQQGNVFSCSVMHEALHNH YTQKSLSLSPGK |
| mut7.57-linker2-hFc (H16E/G27W/R120F) | SEQ ID NO: 44 | APTSSSTKKTQLQLEELLLDLQMILNWINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTCV VVDVSHEDPEVKFNWYVDGVEVHNAKTKPREEQYGSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| mut7.66-linker2-hFc (H16E/P82L/R120F) | SEQ ID NO: 45 | APTSSSTKKTQLQLEELLLDLQMILNGINNYKNPKLTRMLTFKFYM PKKATELKHLQCLEEELKPLEEVLNLAQSKNFHLRLRDLISNINVIV LELKGSETTFMCEYADETATIVEFLNFWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut8-linker2-hFc (D20A) | SEQ ID NO: 46 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVT CVVVDVSHEDPEVKFNWYVDGVEVHNAKTKPREEQYGSTYRVVS VLTVLHQDWLNGKEYKCKVSNKALPAPIEKTISKAKGQPREPQVYT LPPSRDELTKNQVSLTCLVKGFYPSDIAVEWESNGQPENNYKTTPP VLDSDGSFFLYSKLTVDKSRWQQGNVFSCSVMHEALHNHYTQKSL SLSPGK |
| mut8.08-linker2-hFc (D20A/Y31V/A73L/H79Q) | SEQ ID NO: 47 | APTSSSTKKTQLQLEHLLLALQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVT CVVVDVSHEDPEVKFNWYVDGVEVHNAKTKPREEQYGSTYRVVS VLTVLHQDWLNGKEYKCKVSNKALPAPIEKTISKAKGQPREPQVYT LPPSRDELTKNQVSLTCLVKGFYPSDIAVEWESNGQPENNYKTTPP VLDSDGSFFLYSKLTVDKSRWQQGNVFSCSVMHEALHNHYTQKSL SLSPGK |
| mut8.36-linker2-hFc (D20A/R120F) | SEQ ID NO: 48 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVT CVVVDVSHEDPEVKFNWYVDGVEVHNAKTKPREEQYGSTYRVVS VLTVLHQDWLNGKEYKCKVSNKALPAPIEKTISKAKGQPREPQVYT LPPSRDELTKNQVSLTCLVKGFYPSDIAVEWESNGQPENNYKTTPP VLDSDGSFFLYSKLTVDKSRWQQGNVFSCSVMHEALHNHYTQKSL SLSPGK |
| mut11-linker2-hFc (V91R) | SEQ ID NO: 49 | APTSSSTKKTQLQLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |

TABLE 4-continued

Sequences of IL-2 mutants

| Mutant | SEQ ID NO | Sequence information |
|---|---|---|
| mut11.08-linker2-hFc (V91R/Y31V/A73L/H79Q) | SEQ ID NO: 50 | APTSSSTKKTQLQLEHLLLDLQMILNGINNVKNPKLTRMLTFKFYM PKKATELKHLQCLEEELKPLEEVLNLLQSKNFQLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut11.31-linker2-hFc (V91R/Q13L) | SEQ ID NO: 51 | APTSSSTKKTQLLLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut11.36-linker2-hFc (V91R/R120F) | SEQ ID NO: 52 | APTSSSTKKTQLQLEHLLLDLQMILNGINNYKNPKLTRMLTFKFYMPK KATELKHLQCLEEELKPLEEVLNLAQSKNFHLRPRDLISNINRIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTCV VVDVSHEDPEVKFNWYVDGVEVHNAKTKPREEQYGSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| mut11.46-linker2-hFc (V91R/L18I/I89L/V93I) | SEQ ID NO: 53 | APTSSSTKKTQLQLEHLILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLTGGGGSGG GSGGGGSEPKSSDKTHTCPPCPAPELLGGPSVFLFPPKPKDTLMISR TPEVTCVVVDVSHEDPEVKFNWYVDGVEVHNAKTKPREEQYGST YRVVSVLTVLHQDWLNGKEYKCKVSNKALPAPIEKTISKAKGQPR EPQVYTLPPSRDELTKNQVSLTCLVKGFYPSDIAVEWESNGQPENN YKTTPPVLDSDGSFFLYSKLTVDKSRWQQGNVFSCSVMHEALHNH YTQKSLSLSPGK |
| mut61-linker2-hFc (H16E/V91R) | SEQ ID NO: 54 | APTSSSTKKTQLQLEELLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut61.08-linker2-hFc (H16E/V91R/Y31V/A73L/ H79Q) | SEQ ID NO: 55 | APTSSSTKKTQLQLEELLLDLQMILNGINNVKNPKLTRMLTFKFYM PKKATELKHLQCLEEELKPLEEVLNLLQSKNFQLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut61.46-linker2-hFc (H16E/V91R/L18I/I89L/ V93I) | SEQ ID NO: 56 | APTSSSTKKTQLQLEELILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLTGGGGSGG GSGGGGSEPKSSDKTHTCPPCPAPELLGGPSVFLFPPKPKDTLMISR TPEVTCVVVDVSHEDPEVKFNWYVDGVEVHNAKTKPREEQYGST YRVVSVLTVLHQDWLNGKEYKCKVSNKALPAPIEKTISKAKGQPR EPQVYTLPPSRDELTKNQVSLTCLVKGFYPSDIAVEWESNGQPENN YKTTPPVLDSDGSFFLYSKLTVDKSRWQQGNVFSCSVMHEALHNH YTQKSLSLSPGK |

Example 5—Production and Purification of IL-2 Mutants

HEK293 cells (purchased from the Cell Bank of the Chinese Academy of Sciences) were transiently transfected (PEI, polysciences) with the plasmids constructed in Example 4, and then expanded at 37° C. in FreeStyle™ 293 Expression Medium (purchased from Gibco). After 7 days, the cell culture medium was collected, and the cell components were removed by centrifugation to obtain the culture supernatant containing IL-2-hFc fusion proteins.

The fusion proteins in the cell culture supernatant were purified using a 10 mL protein A column (purchased from Bestchrom). The protein A column was first equilibrated with 3 to 5 column volumes of an equilibrium buffer (PBS phosphate buffer, pH7.4), and then loaded with the clear culture supernatant at a flow rate of 10 mL/min. After loading, the protein A column was washed with 3 to 5 column volumes of the equilibrium buffer. The protein bound to the protein A column was eluted with an eluent buffer (0.02 M citric acid buffer, 0.1 M glycine, 0.1 M sodium chloride, pH 3.0), and the elution was monitored by a nucleic acid/protein detector (A280 ultraviolet absorption peak). The eluted proteins were collected and neutralized with the added buffer (1 M arginine, 0.4 M succinic acid, pH 9.0). The target proteins were then collected through a molecular sieve (purchased from Bestchrom) with a buffer system (20 mM PB, 200 mM sodium chloride, pH 6.0-6.5). The purified IL-2 mutant fusion proteins were obtained by aseptic filtration with a 0.22 μm filter and preserved in sterile condition.

The purified IL-2 mutant fusion proteins (mutXX-linker2-hFc) were analyzed for protein concentration (A280/1.4) and SEC purity. The purified IL-2 mutant fusion proteins were qualified. The results of protein yield and concentration are shown in Table 5.

TABLE 5

Detection results of IL-2 mutant fusion proteins

| Mutant | Protein SEC purity | Protein concentration (mg/ml) |
|---|---|---|
| IL-2-linker2-hFc | 97.25% | 1.11 |
| mut7-linker2-hFc | 100% | 0.97 |
| mut7.08-linker2-hFc | 99.84% | 1.73 |
| mut7.36-linker2-hFc | 99.94% | 2.40 |
| mut7.39-linker2-hFc | 99.77% | 1.16 |
| mut7.46-linker2-hFc | 99.90% | 1.28 |
| mut7.57-linker2-hFc | 99.89% | 1.37 |
| mut7.66-linker2-hFc | 99.89% | 1.92 |
| mut8-linker2-hFc | 97.19% | 0.98 |
| mut8.08-linker2-hFc | — | 0.82 |
| mut8.36-linker2-hFc | — | 1.65 |
| mut11-linker2-hFc | 99.13% | 1.65 |
| mut11.08-linker2-hFc | 99.88% | 1.29 |
| mut11.31-linker2-hFc | 100.00% | 1.37 |
| mut11.36-linker2-hFc | 99.97% | 1.15 |
| mut11.46-linker2-hFc | 99.90% | 1.52 |
| mut61-linker2-hFc | 99.93% | 1.36 |
| mut61.08-linker2-hFc | 99.99% | 1.15 |
| mut61.46-linker2-hFc | 99.99% | 1.30 |

Example 6 DSF Assay of IL-2 Mutants

The buffer in Protein Thermal Shift Dye Kit (purchased from Applied Biosystems, Cat. No. 4461146) diluted to 50 times, the IL-2 mutant proteins (purified in Example 5) diluted to 0.5 mg/ml, and the dye diluted to 2 times were added to a 20 μL reaction system. After being mixed evenly, the mixture was added into 8-tube strips with 2 duplicate tubes for each sample. The tubes were covered, centrifuged for 5-10 seconds, and analyzed by the Applied Biosystems 7500. The Tm values were then obtained by using Boltzmann method to analyze the melting curve. The specific Tm values are shown in Table 6.

According to the results shown in Table 6, compared to wild-type IL-2 (IL2-linker2-hFc), the IL-2 mutants (mutXX-linker2-hFc) in Examples 4-5 had increased Tm values by more than 5° C., and some IL-2 mutants had increased Tm values by more than 9° C. As can be seen, all mutants had significantly improved thermal stability.

Surprisingly, compared to wild-type IL-2, the IL-2 mutants with decreased binding ability to βγ subunits had higher Tm values and improved thermal stability. The mutants which further combine thermal stability mutations maintained high Tm values, and some of the mutants combining thermal stability mutations still had Tm values by more than 2° C. and up to 6° C. as compared to the IL-2 mutants comprising only mutations that decrease the binding ability to βγ subunits, and the thermal stability was further improved.

TABLE 6

DSF assay results of IL-2 mutants

| Mutant | Tm (° C.) |
|---|---|
| IL-2-linker2-hFc | 45.95 |
| mut7-linker2-hFc | 51.08 |
| mut7.08-linker2-hFc | 54.70 |
| mut7.36-linker2-hFc | 56.95 |
| mut7.57-linker2-hFc | 57.54 |
| mut7.66-linker2-hFc | 56.64 |
| mut8-linker2-hFc | 55.24 |
| mut8.08-linker2-hFc | 55.32 |
| mut8.36-linker2-hFc | 56.84 |
| mut11-linker2-hFc | 56.63 |
| mut11.08-linker2-hFc | 58.80 |
| mut11.31-linker2-hFc | 59.37 |
| mut11.36-linker2-hFc | 57.56 |
| IL-2-linker2-hFc | 46.74 |
| mut7-linker2-hFc | 51.05 |
| mut7.39-linker2-hFc | 56.30 |
| mut7.46-linker2-hFc | 54.84 |
| mut11-linker2-hFc | 57.17 |
| mut11.46-linker2-hFc | 57.02 |
| IL-2-linker2-hFc | 46.86 |
| mut61-linker2-hFc | 56.84 |
| mut61.08-linker2-hFc | 57.71 |
| mut61.46-linker2-hFc | 56.84 |

Example 7—Construction of Stably Transfected Cell Lines Overexpressing Human or Mouse IL-2 Receptor A. Construction of Stably Transfected Cell Lines Overexpressing Human IL-2 Receptor α

The amino acid sequence of the human IL-2 receptor α subunit (gene accession number in NCBI is P01589, the specific sequence is as shown in SEQ ID NO: 57) was cloned into a pLVX-IRES-Puro vector (purchased from YouBio, Cat NO. VT1464) for lentiviral packaging. The CHO-K1 cell line (purchased from the Cell Bank of the Chinese Academy of Sciences) was then transfected with lentivirus. After transfected with the virus for 72 hours, the CHO cells were detected by flow cytometry with a known IL-2 receptor α subunit antibody (Art NO. 302606, purchased from BioLegend). When the transfected cells were detected to begin to express human IL-2 receptor α subunit, Puromycin (purchased from Gibco) was then added for screening. After the cells were recovered, they were subcloned into 96-well culture plates by limiting dilution, and cultured at 37° ° C. with 5% (v/v) $CO_2$. After about 2 weeks, some monoclonal cells were selected and expanded into 6-well plates. The expanded clones were further screened by flow cytometry with the known IL-2 receptor α subunit antibody. The monoclonal cell lines with better growth and higher fluorescence intensity were selected for further expansion, re-detected by flow cytometry and then frozen in liquid nitrogen to obtain stably transfected cell lines expressing human IL-2 receptor α subunit. Specific selection results are shown in Table 7 and FIG. 1. Positive cells (%) in Table 7 refer to the percentage of positive cells in the total number of cells. Table 7 shows that a series of CHO-K1 cell lines overexpressing IL-2 receptor α subunit have been prepared.

TABLE 7

FACS characterization of CHO-K1 cells expressing human IL-2 receptor α

| | | IL-2 receptor α antibody | | IgG subtype control | |
|---|---|---|---|---|---|
| Serial Number | Transfected cell clone name | Positive cells (%) | Average fluorescence intensity | Positive cells (%) | Average fluorescence intensity |
| 1 | CHO-K1 hIL-2Rα 1A6 | 100.00 | 38168 | — | — |
| 2 | CHO-K1 hIL-2Rα 2D2 | 100.00 | 21817 | — | — |
| 3 | CHO-K1 hIL-2Rα 2D5 | 100.00 | 18111 | — | — |
| 4 | CHO-K1 hIL-2Rα 2B8 | 99.80 | 19018 | 0.04 | 80.70 |

B. Construction of Stably Transfected Cell Lines Overexpressing Human IL-2 Receptor β

Figure 2:
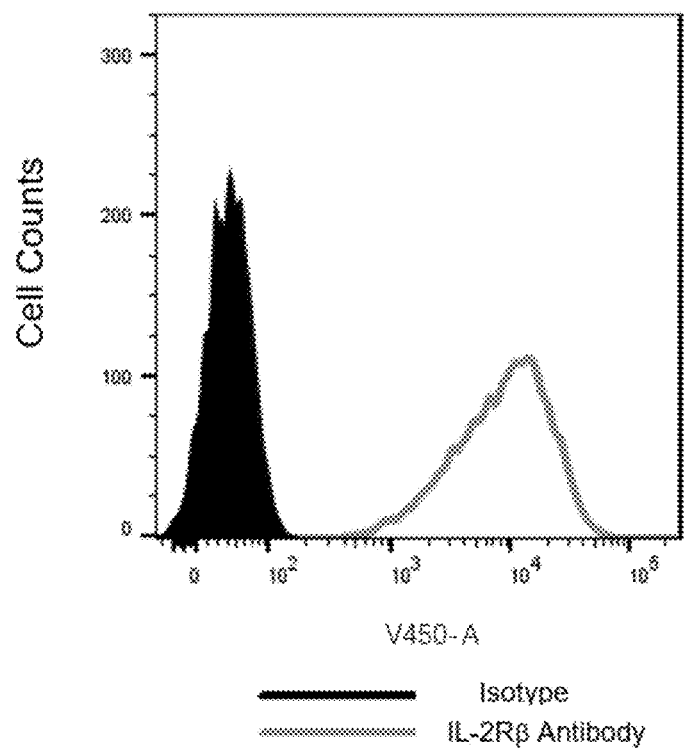
FIG. 2 shows the expression level of human IL-2 receptor β protein in the CHO-K1 hIL-2Rβ recombinant cell line (clone 2A5) detected by flow cytometry (FACS), wherein the IL-2 receptor β antibody is purchased from BioLegend; and the negative control refers to isotype control.

The amino acid sequence of the human IL-2 receptor β subunit (gene accession number in NCBI is P14784, the specific sequence is as shown in SEQ ID NO: 58) was cloned into a pLVX-IRES-Puro vector (purchased from YouBio, Cat NO. VT1464) for lentiviral packaging. The CHO-K1 cell line (purchased from the Cell Bank of the Chinese Academy of Sciences) was then transfected with lentivirus. After transfected with the virus for 72 hours, the CHO-K1 cells were detected by flow cytometry with a known IL-2 receptor β subunit antibody (Cat NO. 339010, purchased from BioLegend). When the transfected cells were detected to begin to express human IL-2 receptor β subunit, Puromycin (purchased from Gibco) was then added for screening. After the cells were recovered, they were subcloned into 96-well culture plates by limiting dilution, and cultured at 37° C. with 5% (v/v) $CO_2$. After about 2 weeks, some monoclonal cells were selected and expanded into 6-well plates. The expanded clones were further screened by flow cytometry with the known IL-2 receptor β subunit antibody. The monoclonal cell lines with better growth and higher fluorescence intensity were selected for further expansion, re-detected by flow cytometry and then frozen in liquid nitrogen to obtain stably transfected cell lines expressing human IL-2 receptor β subunit. Specific selection results are shown in Table 8 and FIG. 2. Positive cells (%) in Table 8 refer to the percentage of positive cells in the total number of cells. Table 8 shows that a series of CHO-K1 cell lines overexpressing IL-2 receptor β subunit have been prepared.

TABLE 8

FACS characterization of CHO-K1 cells expressing human IL-2 receptor β

| | | IL-2 receptor β antibody | | IgG subtype control | |
|---|---|---|---|---|---|
| Serial Number | Transfected cell clone | Positive cells (%) | Average fluorescence intensity | Positive cells (%) | Average fluorescence intensity |
| 1 | CHO-K1 hIL-2Rβ 2A5 | 100.00 | 7905 | — | — |
| 2 | CHO-K1 hIL-2Rβ 2B3 | 99.40 | 5081 | 0.03 | 41.50 |
| 3 | CHO-K1 hIL-2Rβ 2H4 | 99.40 | 1226 | — | — |

C. Construction of Stably Transfected Cell Lines Overexpressing Human IL-2 Receptor βγ

Figure 3A:
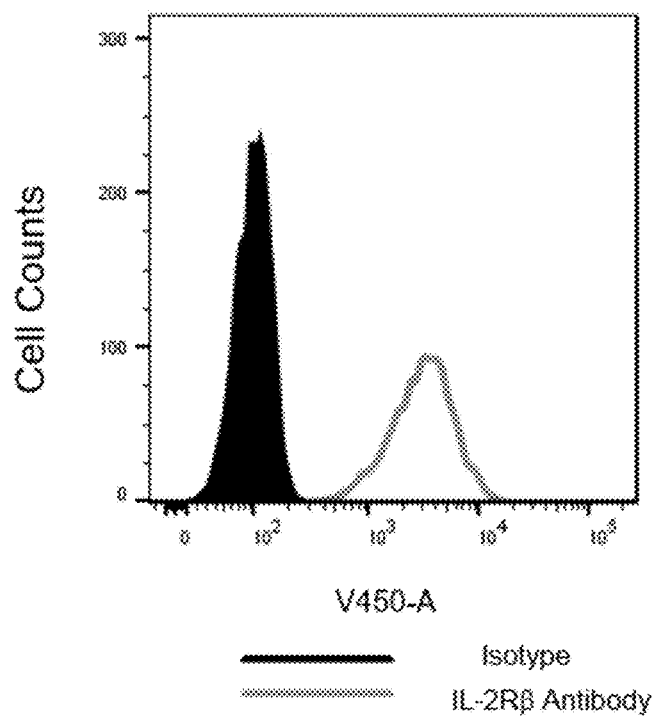
FIG. 3A-3B show the expression level of human IL-2 receptor βγ protein in the CHO-K1 hIL-2Rβγ recombinant cell line (clone 2E6) detected by flow cytometry (FACS), wherein the IL-2 receptor β, γ antibodies were purchased from BioLegend; and the negative control refers to isotype control.
Figure 3B:
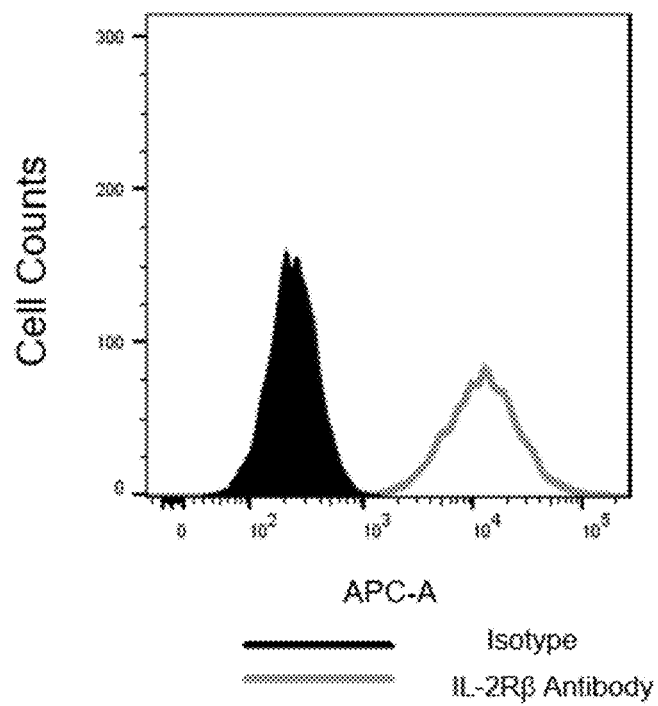

The amino acid sequence of the human IL-2 receptor γ subunit (gene accession number in NCBI is P31785, the specific sequence is SEQ ID NO: 59) was cloned into a pLVX-IRES-Hygro vector for lentiviral packaging. The CHO-K1 cell line overexpressing human IL-2 receptor β subunit (CHO-K1 hIL-2R β, clone 2A5) was then transfected with lentivirus. After transfected with the virus for 72 hours, the CHO-K1 cells were detected by flow cytometry with known IL-2 receptor β and γ☐ subunit antibodies (Cat NOs. 339010 and 338608, purchased from BioLegend). When the transfected cells were detected to begin to express human IL-2 receptor βγ subunits, Puromycin and Hygromycin (purchased from Gibco, Thermo) were then added for screening. After the cells were recovered, they were subcloned into 96-well culture plates by limiting dilution, and cultured at 37° ° C. with 5% (v/v) $CO_2$. After about 2 weeks, some monoclonal cells were selected and expanded into 6-well plates. The expanded clones were screened by flow cytometry with the known IL-2 receptor β and γ subunit antibodies. The monoclonal cell lines with better growth and higher fluorescence intensity were selected for further expansion, re-detected by flow cytometry and then frozen in liquid nitrogen to obtain stably transfected cell lines expressing human IL-2 receptor βγ subunits. Specific selection results are shown in Table 9 and FIG. 3A-FIG. 3B. Positive cells (%) in Table 9 refer to the percentage of positive cells in the total number of cells. Table 9 shows that a series of CHO-K1 cell lines overexpressing IL-2 receptor βγ subunits have been prepared.

TABLE 9

FACS characterization of CHO-K1 cells expressing human IL-2 receptor βγ

| Serial Number | Transfected cell clone | IL-2 receptor β antibody | | IgG subtype control | | IL-2 receptor γ antibody | | IgG subtype control | |
|---|---|---|---|---|---|---|---|---|---|
| | | Positive cells (%) | Average fluorescence intensity | Positive cells (%) | Average fluorescence intensity | Positive cells (%) | Average fluorescence intensity | Positive cells (%) | Average fluorescence intensity |
| 1 | CHO-K1 IL-2Rβγ 2D3 | 100.00 | 4569 | 0.65 | 115 | 98.90 | 8932 | 23.30 | 1070 |
| 2 | CHO-K1 hIL-2Rβγ 2C11 | 99.70 | 2111 | — | — | 99.00 | 31664 | — | — |
| 3 | CHO-K1 IL-2Rβγ 2E6 | 100.00 | 2909 | — | — | 98.80 | 11764 | — | — |

D. Construction of Stably Transfected Cell Lines Overexpressing Human IL-2 Receptor αβγ

Figure 4A:
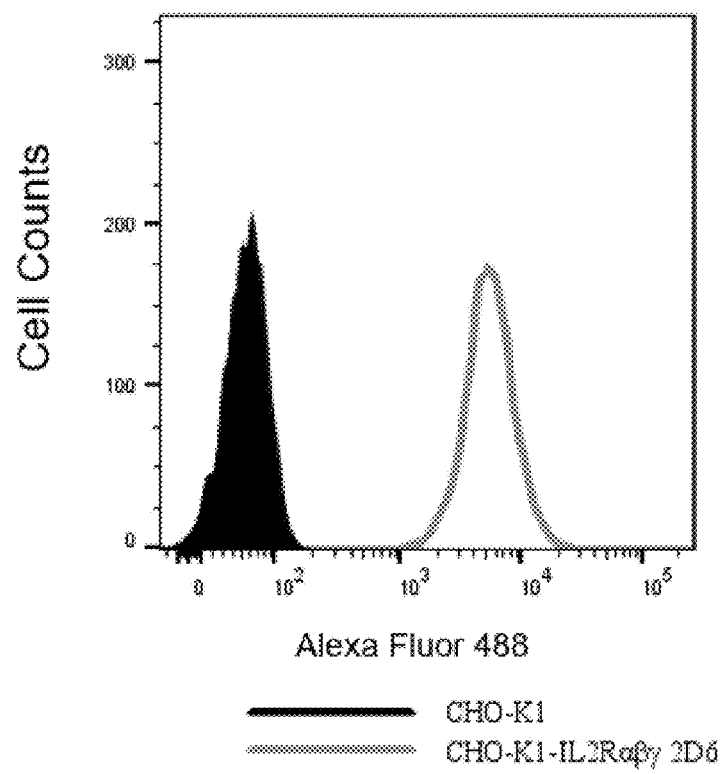
FIG. 4A-4C show the expression level of human IL-2 receptor αβγ protein in the CHO-K1 hIL-2Rαβγ recombinant cell line (clone 2D6) detected by flow cytometry (FACS), wherein the IL-2 receptor α, β, γ antibodies were purchased from BioLegend; and the negative control refers to the expression level of corresponding receptors in the parental CHO-K1 cells.
Figure 4B:
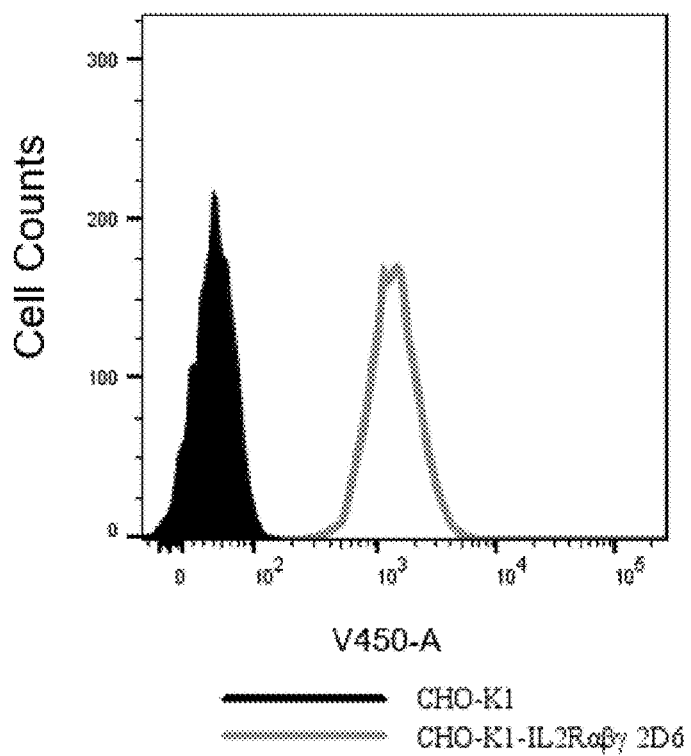
Figure 4C:
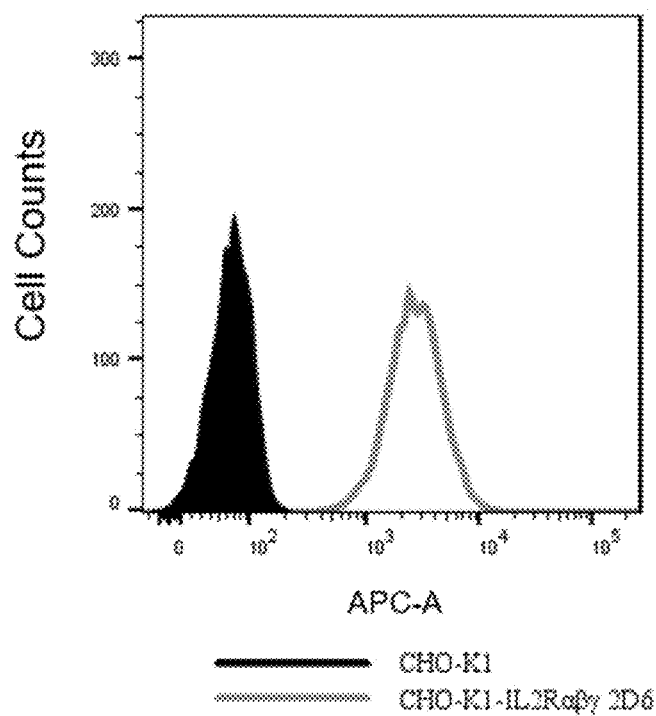
Figure 5A:
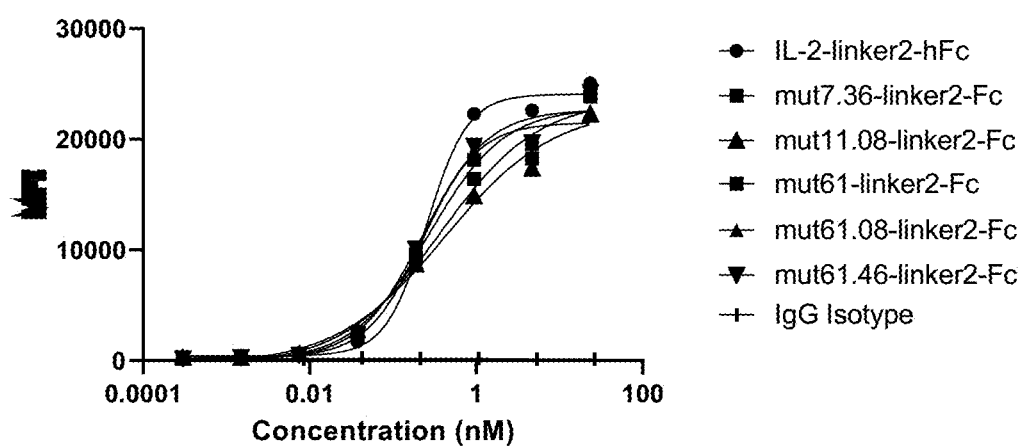
FIG. 5A-5D show the binding activity of IL-2 mutant protein to CHO-K1 IL-2 receptor αβγ and IL-2 receptor βγ recombinant cells detected by flow cytometry (FACS)
Figure 5B:
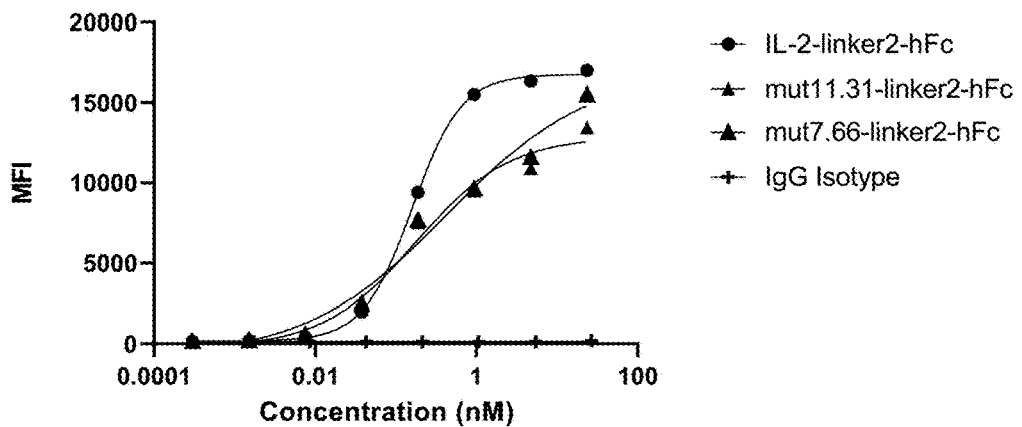
Figure 5C:
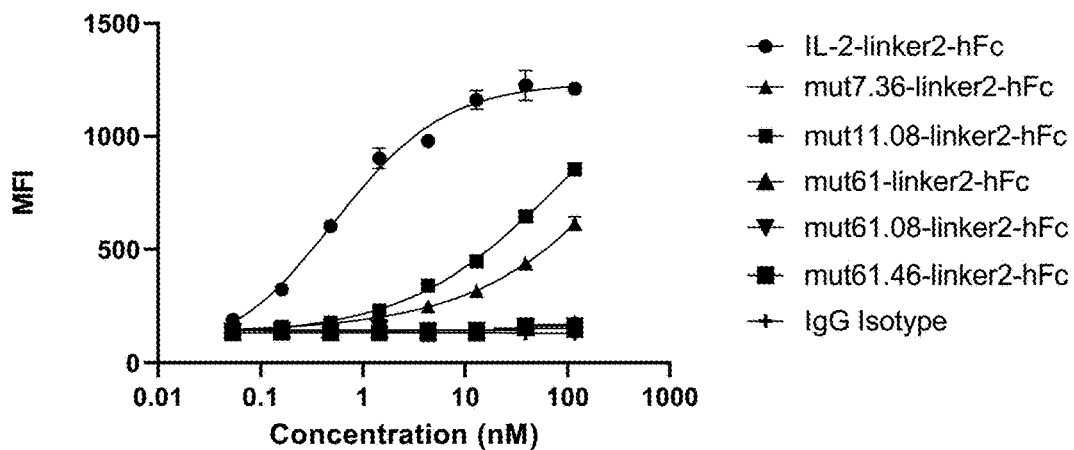
Figure 5D:
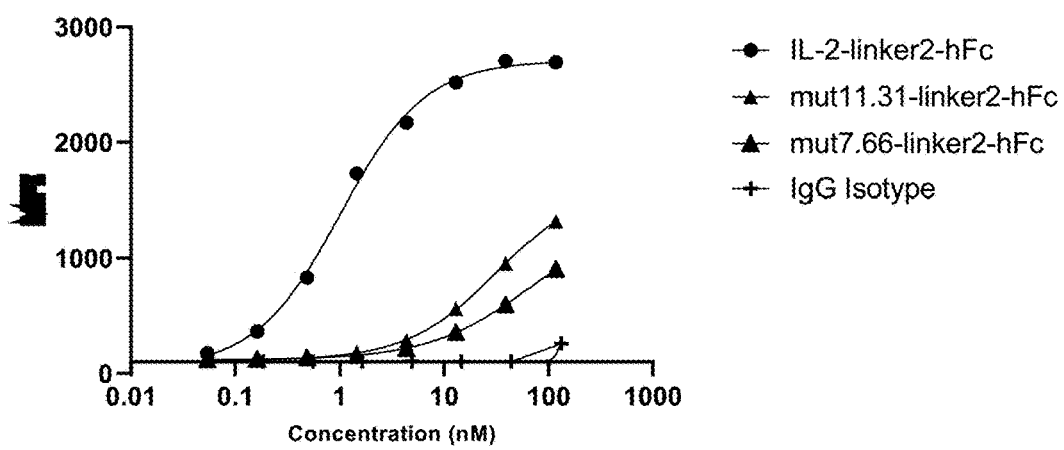
Figure 6A:
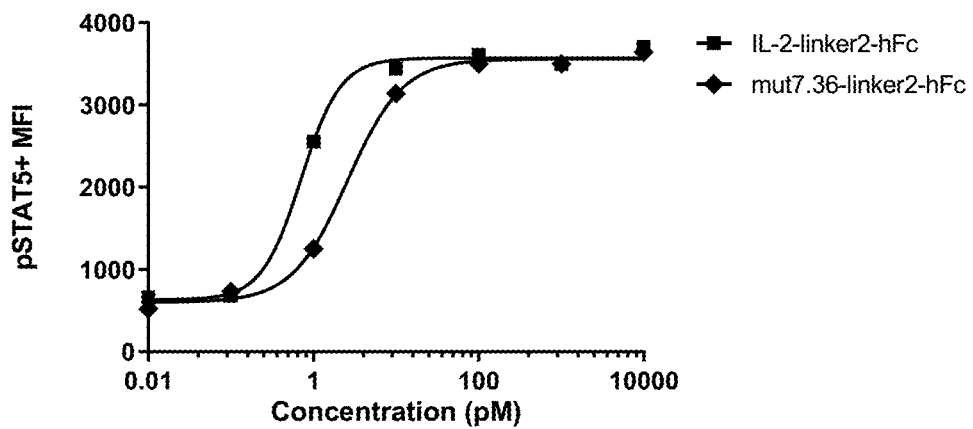
FIG. 6A-6I show the effect of IL-2 mutant protein on the level of STAT5 phosphorylation in Tregs (FIGS. 6A-6C), $CD4^+CD25^-FoxP3^-$ T cells (FIGS. 6D-6F) and $CD8^+$ T cells (FIGS. 6G-6I)
Figure 6B:
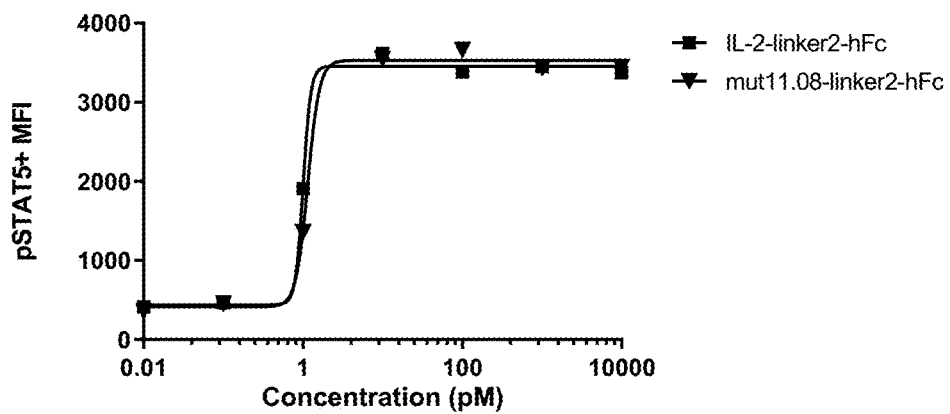
Figure 6C:
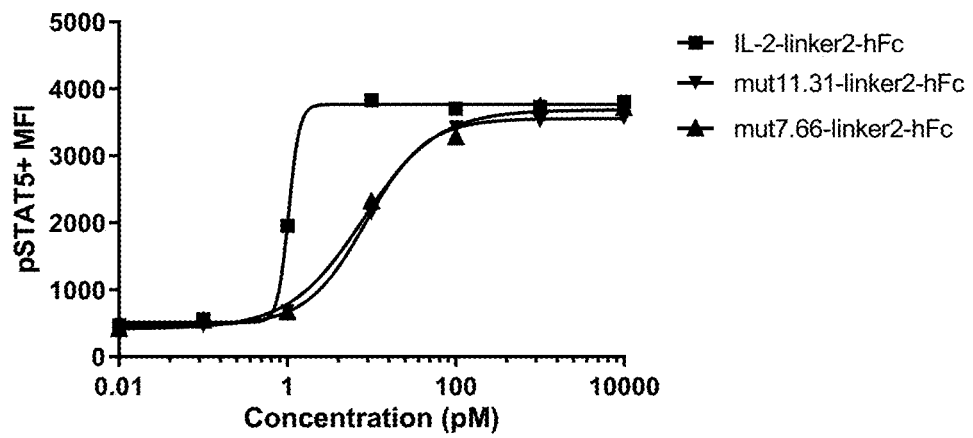
Figure 6D:
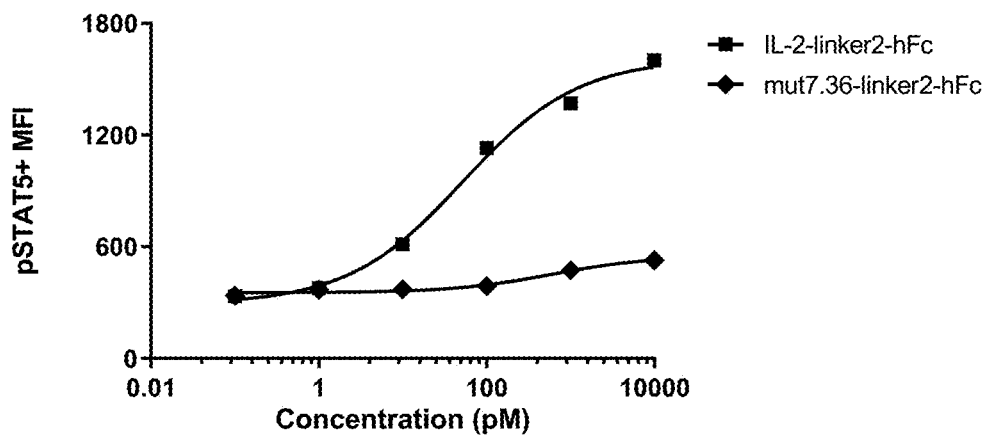
Figure 6E:
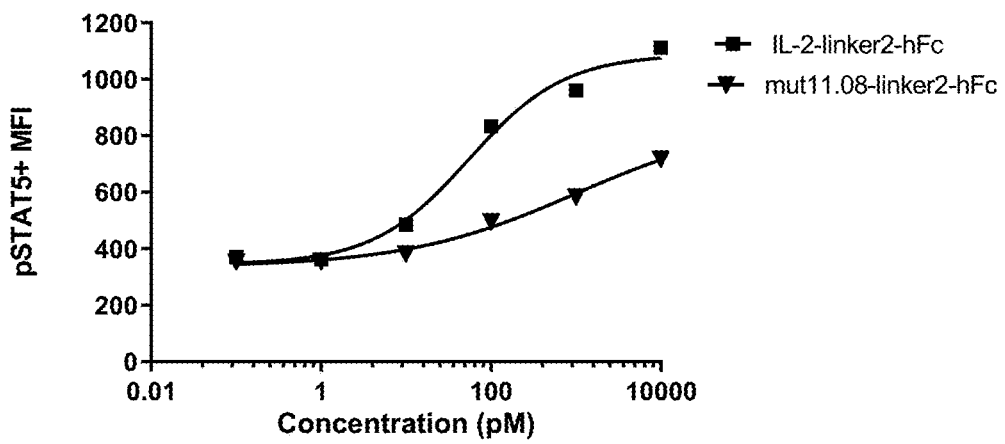
Figure 6F:
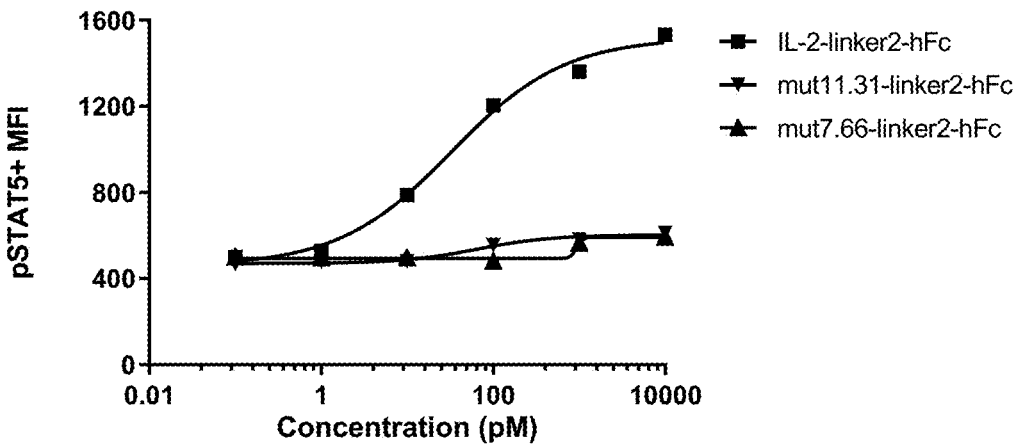
Figure 6G:
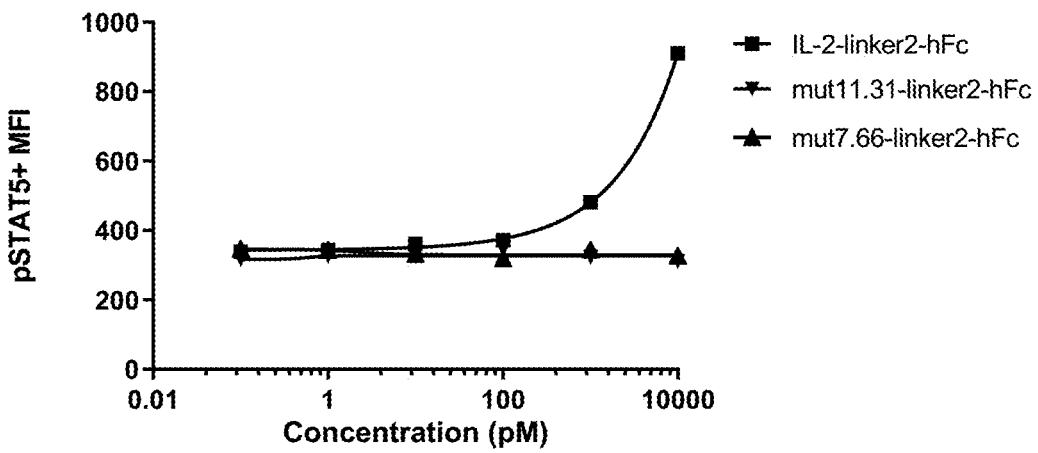
Figure 6H:
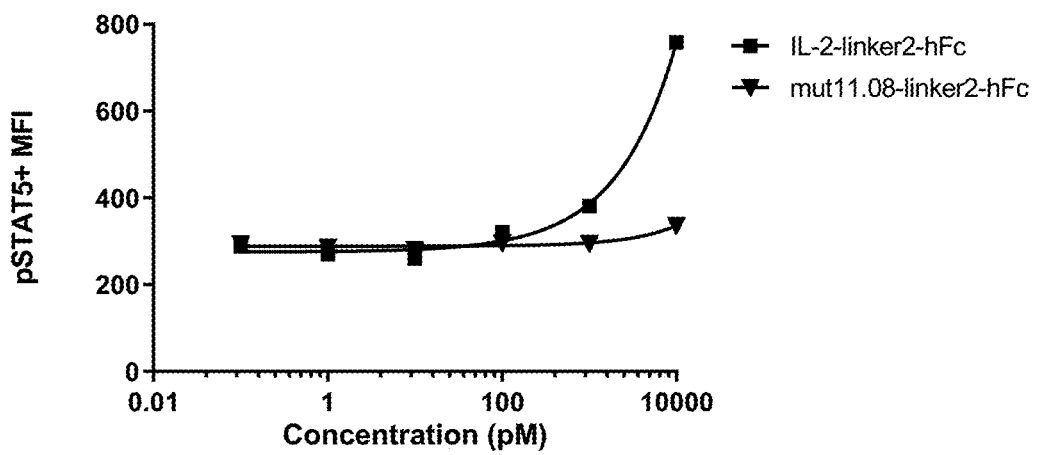
Figure 6I:
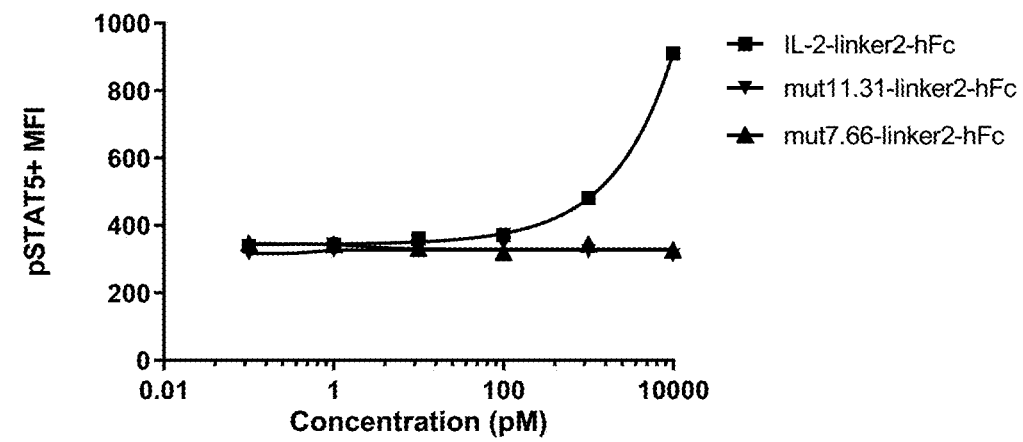
Figure 7A:
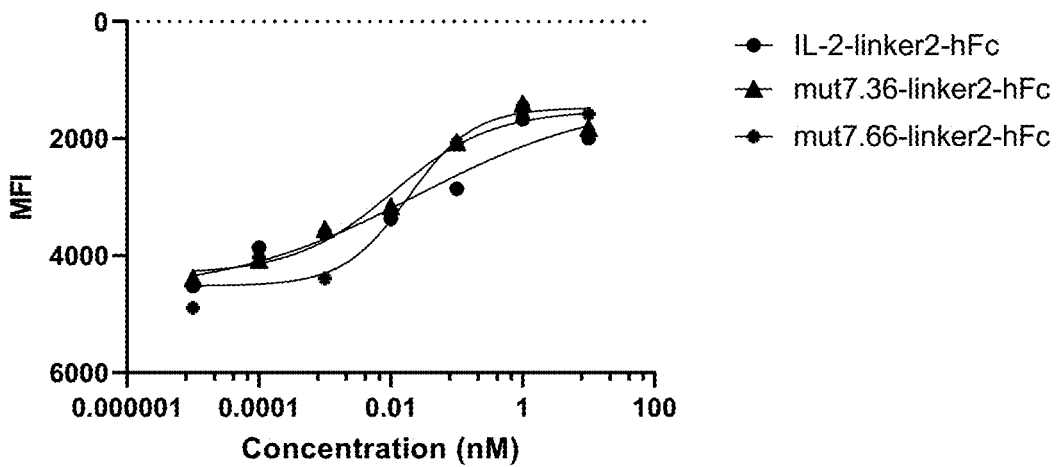
FIG. 7A-7F show the effect of IL-2 mutant protein on the level of proliferation of Tregs (FIGS. 7A-7B), $CD4^+CD25^-$ $FoxP3^-$T cells (FIGS. 7C-7D), and $CD8^+CD25^-$ T cells (FIGS. 7E-7F)
Figure 7B:
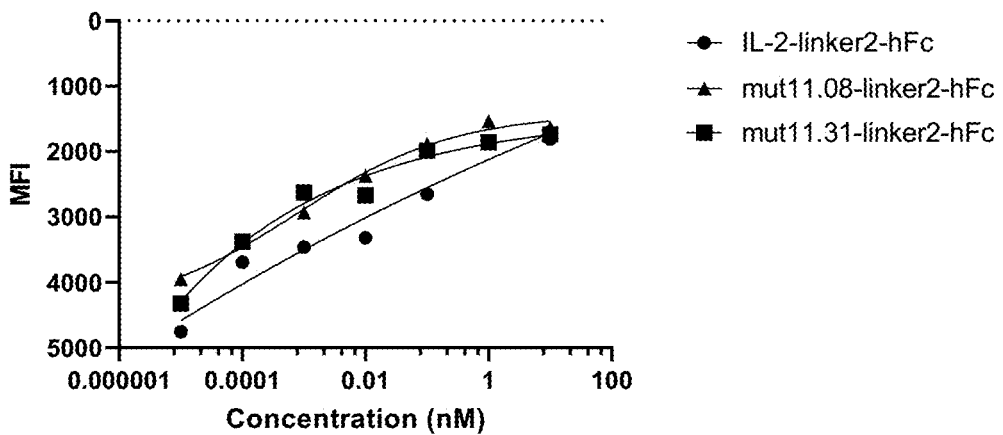
Figure 7C:
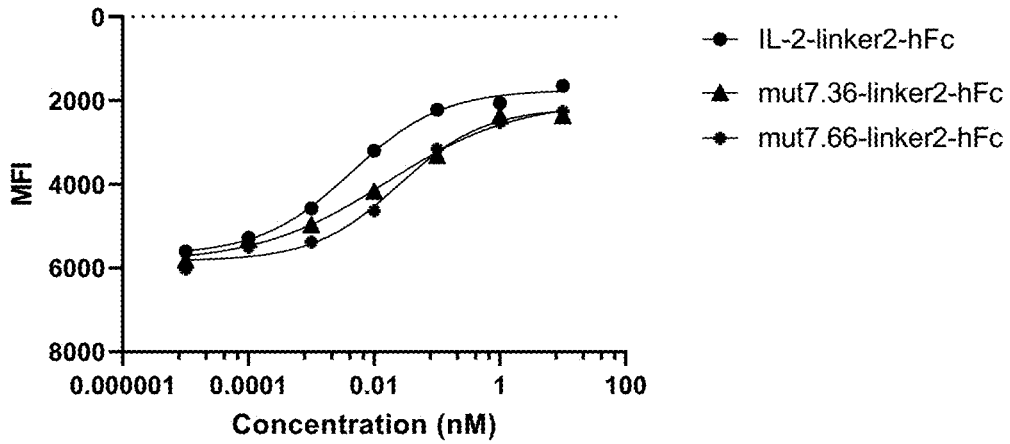
Figure 7D:
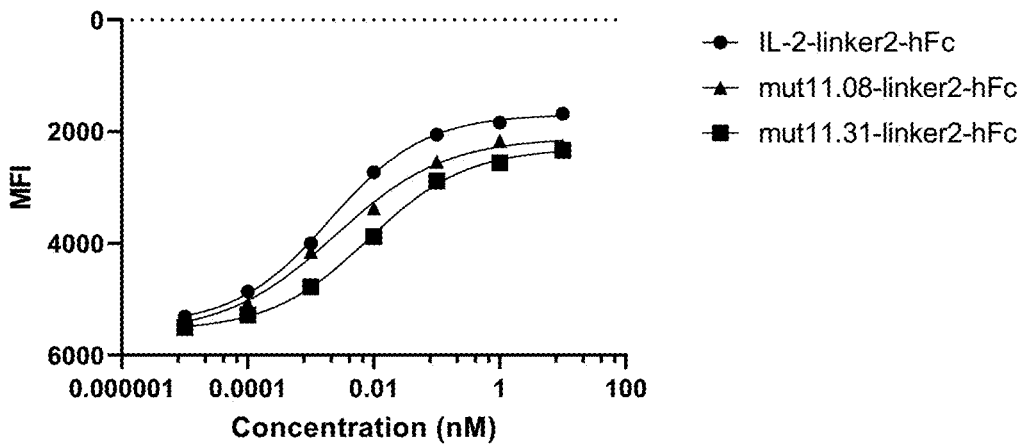
Figure 7E:
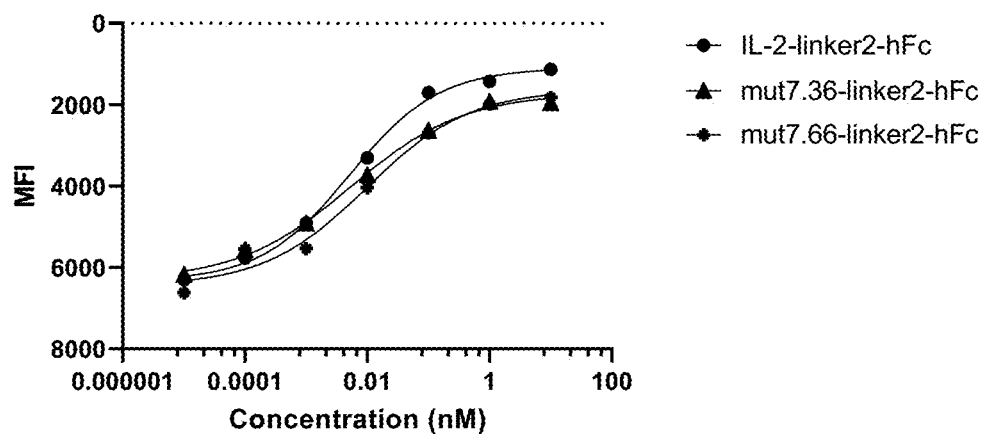
Figure 7F:
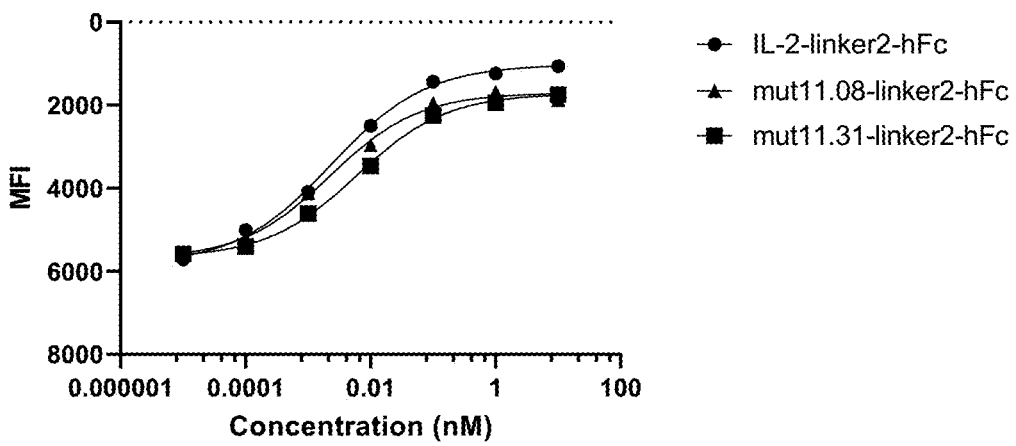

The amino acid sequence of the human IL-2 receptor α subunit was cloned into a pLVX-IRES-zsGreen vector for lentiviral packaging. The CHO-K1 cell line overexpressing human IL-2 receptor βγ subunits were transfected with ventivirus. After transfected with the virus for 72 hours, the CHO-K1 cells were detected by flow cytometry with the known IL-2 receptor α, β and γ subunit antibodies (ibid., purchased from BioLegend). When the transfected cells were detected to begin to express human IL-2 receptor αβγ subunits, Puromycin, Hygromycin (purchased from Gibco, Thermo) and GFP (for fluorescent expression) were added for screening. After the cells were recovered, they were subcloned into 96-well culture plates by limiting dilution, and cultured at 37° ° C. with 5% (v/v) $CO_2$. After about 2 weeks, some monoclonal cells were selected and expanded into 6-well plates. The expanded clones were screened by flow cytometry with the known IL-2 receptor α, β and γ subunit antibodies. The monoclonal cell lines with better growth and higher fluorescence intensity were selected for further expansion, re-detected by flow cytometry and then frozen in liquid nitrogen to obtain stably transfected cell lines expressing human IL-2 receptor αβγ subunits. Specific selection results are shown in Table 10 and FIG. 4A-FIG. 4B. Positive cells (%) in Table 10 refer to the percentage of positive cells in the total number of cells. Table 10 shows that a series of CHO-K1 cell lines overexpressing IL-2 receptor αβγ subunits have been prepared.

TABLE 10

FACS characterization of CHO-K1 cells expressing human IL-2 receptor αβγ

| Serial Number | Transfected cell clone | IL-2 receptor α antibody | | IL-2 receptor β antibody | | IL-2 receptor γ antibody | |
|---|---|---|---|---|---|---|---|
| | | Positive cells (%) | Average fluorescence intensity | Positive cells (%) | Average fluorescence intensity | Positive cells (%) | Average fluorescence intensity |
| 1 | CHO-K1 hIL-2R αβγ 1E3 | 99.90 | 10667 | 100.00 | 3002 | 99.90 | 14863 |
| 2 | CHO-K1 hIL-2R αβγ 2D6 | 99.90 | 5265 | 99.90 | 1324 | 99.80 | 2575 |
| 3 | CHO-K1 hIL-2R αβγ 1A10 | 100.00 | 12255 | 88.60 | 465 | 99.60 | 4106 |

TABLE 11

Genes used in the construction of stably transfected cell lines in Example 7 (A-D) and sequence information of encoded proteins thereof

| Gene | SEQ ID NO | Sequence information |
|---|---|---|
| hIL2Rα | SEQ ID NO: 57 | MDSYLLMWGLLTFIMVPGCQAELCDDDPPEIPHATFKAMAYKEGTMLNCEC KRGFRRIKSGSLYMLCTGNSSHSSWDNQCQCTSSATRNTTKQVTPQPEEQKE RKTTEMQSPMQPVDQASLPGHCREPPPWENEATERIYHFVVGQMVYYQCVQ GYRALHRGPAESVCKMTHGKTRWTQPQLICTGEMETSQFPGEEKPQASPEG RPESETSCLVTTTDFQIQTEMAATMETSIFTTEYQVAVAGCVFLLISVLLLSGL TWQRRQRKSRRTI |
| hIL2Rβ | SEQ ID NO: 58 | MAAPALSWRLPLLILLLPLATSWASAAVNGTSQFTCFYNSRANISCVWSQDG ALQDTSCQVHAWPDRRRWNQTCELLPVSQASWACNLILGAPDSQKLTTVDI VTLRVLCREGVRWRVMAIQDFKPFENLRLMAPISLQVVHVETHRCNISWEIS QASHYFERHLEFEARTLSPGHTWEEAPLLTLKQKQEWICLETLTPDTQYEFQ VRVKPLQGEFTTWSPWSQPLAFRTKPAALGKDTIPWLGHLLVGLSGAFGFIIL |

TABLE 11-continued

Genes used in the construction of stably transfected cell lines in Example 7 (A-D) and sequence information of encoded proteins thereof

| Gene | SEQ ID NO | Sequence information |
|------|-----------|---------------------|
|  |  | VYLLINCRNTGPWLKKVLKCNTPDPSKFFSQLSSEHGGDVQKWLSSPFPSSSF SPGGLAPEISPLEVLERDKVTQLLLQQDKVPEPASLSSNHSLTSCFTNQGYFFF HLPDALEIEACQVYFTYDPYSEEDPDEGVAGAPTGSSPQPLQPLSGEDDAYCT FPSRDDLLLFSPSLLGGPSPPSTAPGGSGAGEERMPPSLQERVPRDWDPQPLG PPTPGVPDLVDFQPPPELVLREAGEEVPDAGPREGVSFPWSRPPGQGEFRALN ARLPLNTDAYLSLQELQGQDPTHLV |
| hIL2Rγ | SEQ ID NO: 59 | MLKPSLPFTSLLFLQLPLLGVGLNTTILTPNGNEDTTADFFLTTMPTDSLSVST LPLPEVQCFVFNVEYMNCTWNSSSEPQPTNLTLHYWYKNSDNDKVQKCSHY LFSEEITSGCQLQKKEIHLYQTFVVQLQDPREPRRQATQMLKLQNLVIPWAPE NLTLHKLSESQLELNWNNRFLNHCLEHLVQYRTDWDHSWTEQSVDYRHKFS LPSVDGQKRYTFRVRSRFNPLCGSAQHWSEWSHPIHWGSNTSKENPFLFALE AVVISVGSMGLIISLLCVYFWLERTMPRIPTLKNLEDLVTEYHGNFSAWSGVS KGLAESLQPDYSERLCLVSEIPPKGGALGEGPGASPCNQHSPYWAPPCYTLKP ET |

Example 8—Detection of the Binding Activity of IL-2 Mutant to Receptor-Expressing Cells by Flow Cytometry (FACS)

CHO-K1 cells expressing IL-2 receptor αβγ (CHO-K1 hIL-2R αβγ 2D6) or CHO-K1 cells expressing IL-2 receptor βγ (CHO-K1 hIL-2R βγ 2E6) were expanded to 90% confluency in T-75 cell culture flasks. The medium was removed, followed by washing of the flask once with PBS buffer (purchased from Hyclone, Cat NO. SH30256.01). The cells were treated with 2 mL of trypsin containing 0.25% EDTA (purchased from Invitrogen, Cat NO. 25200072) for 2-3 minutes, neutralized with 8 mL of DMEM/F-12 (purchased from Gibco, Cat NO. 12634-010) containing 10% (w/w) fetal bovine serum (purchased from Gibco, Cat NO. 10099-141C), pipetted for 3-4 times, then collected into a 15 ml centrifuge tube, counted, and centrifuged at 1000 rpm for 5 minutes at room temperature. After the culture medium was discarded, the cells were re-suspended with RPMI-1640 containing 2% (w/w) fetal bovine serum (purchased from Gibco, Cat NO. A10491-01) and then diluted to 1.43×10$^6$ cells/ml. The cells were added into a U-shaped bottom 96-well FACS reaction plate at 70 μL per well and placed at 4° C. or on ice for later use. The IL-2 mutants to be detected were diluted with RPMI-1640 containing 2% (w/w) fetal bovine serum, added into the cells at 30 μL per well, mixed well, and incubated on ice for 1 hour. The plate was then washed twice with FACS buffer (PBS buffer containing 2% (w/w) bovine serum albumin).

Fluorescence-labeled secondary antibody (purchased from Biolegend, Cat NO. 409306) was added into the plate at 100 μL per well and incubated on ice for 30 minutes. The plate was then washed twice with FACS buffer. Detection and analysis were performed by FACS (FACS Canto II, purchased from BD Company). Alternatively, the cells were suspended with 100 μL FACS buffer containing 2% (w/w) paraformaldehyde (purchased from DingGuo, Cat NO. AR-0211) and then stored at 4° C. until further FACS detection. 100 μL PBS buffer was added to each well before FACS detection. Detection and analysis was performed by FACS. The results are shown in FIG. 5A-FIG. 5D and Table 12-Table 13. The results show that IL-2 mutants could bind to human IL-2 receptor αβγ trimer on the cell surface. The binding activity of IL-2 mutants to human IL-2 receptor βγ dimer on the cell surface was weaker than that of wild type IL-2. The binding activity of mut61-linker2-hFc, mut61.08-linker2-hFc and mut61.46-linker2-hFc to CHO-K1 IL-2R βγ dimer was greatly inhibited. The MFI in the following tables is the average fluorescence intensity value of the detected cell populations.

TABLE 12

Binding Activity of IL-2 mutants to CHO-K1 IL2 receptor αβγ recombinant cell line (CHO-K1 IL2R αβγ) detected by FACS

| | Protein concentration (nM) | | | | | | | |
|---|---|---|---|---|---|---|---|---|
| | 23.529 | 4.7059 | 0.9412 | 0.1882 | 0.0376 | 0.0075 | 0.0015 | 0.0003 |
| IL-2-linker2-hFc(MFI) | 25072 | 22623 | 22295 | 9026 | 1728 | 457 | 161 | 251 |
| Mut7.36-linker2-hFc(MFI) | 23892 | 19565 | 18132 | 9608 | 2416 | 570 | 272 | 171 |
| Mut11.08-linker2-hFc(MFI) | 22230 | 17370 | 14857 | 8713 | 2736 | 621 | 268 | 251 |
| Mut61-linker2-hFc(MFI) | 23858 | 18259 | 16403 | 9188 | 2307 | 544 | 224 | 194 |
| Mut61.08-linker2-hFc(MFI) | 22558 | 19652 | 18992 | 9557 | 2131 | 575 | 303 | 190 |
| Mut61.46-linker2-hFc(MFI) | 24244 | 19701 | 19386 | 10124 | 2384 | 521 | 280 | 186 |
| Protein concentration (nM) | 26.667 | 5.3333 | 1.0667 | 0.2133 | 0.0427 | 0.0085 | 0.0017 | 0.0003 |
| Human IgG control | 118 | 124 | 157 | 181 | 274 | 119 | 120 | 146 |

| | Protein concentration (nM) | | | | | | | |
|---|---|---|---|---|---|---|---|---|
| | 23.529 | 4.7059 | 0.9412 | 0.1882 | 0.0376 | 0.0075 | 0.0015 | 0.0003 |
| IL-2-linker2-hFc(MFI) | 17021 | 16362 | 15503 | 9402 | 1983 | 423 | 188 | 156 |
| Mut7.66-linker2-hFc(MFI) | 15503 | 11604 | 9659 | 7683 | 2485 | 568 | 227 | 177 |

TABLE 12-continued

Binding Activity of IL-2 mutants to CHO-K1 IL2 receptor αβγ recombinant cell line (CHO-K1 IL2R αβγ) detected by FACS

| | | | | | | | | |
|---|---|---|---|---|---|---|---|---|
| Mut11.31-linker2-hFc(MFI) | 13449 | 10906 | 9502 | 7521 | 2181 | 553 | 214 | 172 |
| Protein concentration (nM) | 26.667 | 5.3333 | 1.0667 | 0.2133 | 0.0427 | 0.0085 | 0.0017 | 0.0003 |
| Human IgG control | 187 | 136 | 138 | 139 | 144 | 145 | 140 | 146 |

TABLE 13

Binding Activity of IL-2 mutants to CHO-K1 IL2 receptor βγ recombinant cell line (CHO-K1 IL2R βγ) detected by FACS

| | Protein concentration (nM) | | | | | | |
|---|---|---|---|---|---|---|---|
| | 117.65 | 39.216 | 13.072 | 4.357 | 1.452 | 0.484 | 0.161 | 0.054 |
| IL-2-linker2-hFc(MFI) | 1210 | 1226 | 1162 | 980 | 904 | 603 | 325 | 191 |
| Mut7.36-linker2-hFc(MFI) | 615 | 438 | 318 | 250 | 210 | 165 | 156 | 153 |
| Mut11.08-linker2-hFc(MFI) | 854 | 645 | 447 | 342 | 232 | 178 | 160 | 144 |
| Mut61-linker2-hFc(MFI) | 169 | 155 | 142 | 142 | 145 | 146 | 148 | 142 |
| Mut61.08-linker2-hFc(MFI) | 164 | 163 | 144 | 144 | 157 | 144 | 146 | 141 |
| Mut61.46-linker2-hFc(MFI) | 148 | 159 | 132 | 131 | 134 | 133 | 136 | 134 |
| Protein concentration (nM) | 133.33 | 44.444 | 14.815 | 4.938 | 1.646 | 0.549 | 0.183 | 0.061 |
| Human IgG control | 130 | 130 | 136 | 134 | 139 | 141 | 141 | 146 |

| | Protein concentration (nM) | | | | | | |
|---|---|---|---|---|---|---|---|
| | 117.65 | 39.216 | 13.072 | 4.357 | 1.452 | 0.484 | 0.161 | 0.054 |
| IL-2-linker2-hFc(MFI) | 2694 | 2703 | 2518 | 2170 | 1729 | 831 | 363 | 177 |
| Mut7.66-linker2-hFc(MFI) | 905 | 597 | 357 | 216 | 157 | 136 | 124 | 118 |
| Mut11.31-linker2-hFc(MFI) | 1320 | 950 | 560 | 285 | 180 | 134 | 121 | 115 |
| Protein concentration (nM) | 133.33 | 44.444 | 14.815 | 4.938 | 1.646 | 0.549 | 0.183 | 0.061 |
| Human IgG control | 259 | 100 | 101 | 107 | 101 | 102 | 104 | 109 |

Example 9—Activation of Signaling Pathways in Different Cells by IL-2 Mutants Detected by STAT5 Phosphorylation Assay Frozen Peripheral Blood Mononuclear Cells (PBMCs) (purchased from Allcells) were thawed. 50 μL of 5×10$^5$ PBMCs and 50 μL of an IL-2 mutant were added to each well, and allowed to react in a carbon dioxide incubator for 15 minutes. After the reaction, 100 μL precooled DPBS was added to each well to stop the reaction. After centrifugation, PBMCs were stained with Livedead Violet (Invitrogen-L 34964), fixed with Fix I (BD-557870) at 37° C. for 10 minutes, and permeabilized with PermIII (BD-558050) on ice for 30 minutes. PBMCs were then stained with CD3-AF700 (BD-557943), CD4-PerCP Cy5.5 (BD-560650), CD8-FTIC (BD-555366), CD25-PE (BD-557138), FoxP3-AF647 (BD-560045), and pSTAT5-PE Cy7 (Invitrogen-25-9010-42) at room temperature for 1 hour and washed twice before detection. The results are shown in FIG. 6A-FIG. 6I and Table 14-Table 16. The results show that, compared to wild-type IL-2, the STAT5 phosphorylation level activated by IL-2 mutants was similar in Treg cells, but was significantly reduced in CD4$^+$CD25$^-$FoxP3$^-$ T cells or CD8$^+$ T cells. The MFI in the following tables is the average fluorescence intensity value of STAT5 phosphorylation in the detected cell populations.

TABLE 14

STAT5 phosphorylation signal activated by IL-2 mutants in Tregs detected by FACS

| | Protein concentration (pM) | | | | | | |
|---|---|---|---|---|---|---|---|
| | 10000 | 1000 | 100 | 10 | 1 | 0.1 | 0.01 |
| IL-2-linker2-hFc(MFI) | 3706 | 3498 | 3607 | 3440 | 2554 | 680 | 662 |
| Mut7.36-linker2-hFc(MFI) | 3463 | 3498 | 3498 | 3139 | 1250 | 735 | 522 |
| IL-2-linker2-hFc(MFI) | 3371 | 3451 | 3382 | 3619 | 1909 | 464 | 415 |
| Mut11.08-linker2-hFc(MFI) | 3451 | 3440 | 3668 | 3558 | 1365 | 462 | 366 |
| IL-2-linker2-hFc(MFI) | 3807 | 3731 | 3706 | 3833 | 1955 | 561 | 467 |
| Mut7.66-linker2-hFc(MFI) | 3718 | 3743 | 3280 | 2323 | 668 | 544 | 419 |
| Mut11.31-linker2-hFc(MFI) | 3570 | 3522 | 3428 | 2149 | 680 | 465 | 473 |

TABLE 15

STAT5 phosphorylation signal activated by IL-2 mutants in CD4$^+$CD25$^-$FoxP3$^-$T cells detected by FACS

| | Protein concentration (pM) | | | | | |
|---|---|---|---|---|---|---|
| | 10000 | 1000 | 100 | 10 | 1 | 0.1 |
| IL-2-linker2-hFc(MFI) | 1601 | 1370 | 1130 | 612 | 377 | 333 |
| Mut7.36-linker2-hFc(MFI) | 527 | 473 | 388 | 371 | 368 | 336 |
| IL-2-linker2-hFc(MFI) | 1111 | 960 | 833 | 485 | 362 | 370 |
| Mut11.08-linker2-hFc(MFI) | 718 | 584 | 496 | 382 | 355 | 354 |
| IL-2-linker2-hFc(MFI) | 1532 | 1361 | 1205 | 789 | 529 | 501 |
| Mut7.66-linker2-hFc(MFI) | 592 | 564 | 481 | 496 | 496 | 501 |
| Mut11.31-linker2-hFc(MFI) | 612 | 582 | 557 | 481 | 481 | 467 |

TABLE 16

STAT5 phosphorylation signal activated by IL-2 mutants in CD8$^+$ T cell detected by FACS

| | Protein concentration (pM) | | | | | |
|---|---|---|---|---|---|---|
| | 10000 | 1000 | 100 | 10 | 1 | 0.1 |
| IL-2-linker2-hFc(MFI) | 973 | 413 | 274 | 221 | 233 | 239 |
| Mut7.36-linker2-hFc(MFI) | 270 | 264 | 245 | 247 | 259 | 236 |
| IL-2-linker2-hFc(MFI) | 758 | 381 | 321 | 260 | 270 | 288 |
| Mut11.08-linker2-hFc(MFI) | 336 | 295 | 296 | 281 | 286 | 294 |
| IL-2-linker2-hFc(MFI) | 910 | 481 | 372 | 361 | 344 | 339 |
| Mut7.66-linker2-hFc(MFI) | 326 | 344 | 319 | 331 | 343 | 346 |
| Mut11.31-linker2-hFc(MFI) | 311 | 324 | 346 | 327 | 326 | 317 |

Example 10—Regulatory Effect of IL-2 Mutants on T Cell Proliferation

The frozen PBMCs were thawed, re-suspended in RPMI-1640 (purchased from Gibco, Cat NO. A10491-01) containing 10% FBS (purchased from Gibco, Cat NO. 10099-141C), and cultured in a six-well plate pre-coated with 100 ng/ml CD3 antibody (purchased from BD, Cat NO. 566685) for two days. The cells were collected, washed three times with PBS buffer (purchased from Hyclone, Cat NO. SH30256.01), re-suspended in RPMI-1640 containing 10% FBS, and then cultured in a six-well plate for five days. The cells were then collected, washed once with PBS buffer, stained with Celltrace Violet (purchased from Invitrogen, Cat NO. C34557), washed once with culture medium, re-suspended with culture medium, added into a 24-well plate (900 μL cell per well), added with 100 μL of the IL-2 mutant protein samples and then cultured for seven days.

The cells were then collected, re-suspended with PBS (purchased from Sangon Biotech, Cat NO. B548117-0500) containing 1% BSA (purchased from Sangon Biotech Cat NO. A500023-0100), and added into a 96-well plate.

The cells were stained with BV605-CD8 (purchased from Biolengend, Cat NO. 344742) at room temperature for 30 min, washed with PBS containing 1% BSA, fixed with 200 μL/well of fixing solution (purchased from eBioscience, Cat NO. 00-5523-00) at 4° C. for half an hour, and washed with PBS containing 1% BSA. The cells were then permeabilized with 200 μL/well of permeablizing solution (purchased from eBioscience, Cat NO. 00-5523-00) at 4° C. for 30 minutes, and washed with PBS containing 1% BSA. The cells were further stained with APC-CY7-CD3 antibody (purchased from Biolengend, Cat NO. 344818), CD25 antibody (purchased from Biolengend, Cat NO. 302606) and Foxp3 antibody (purchased from ThermoFisher #17-4777-42) at room temperature for 30 minutes, washed with PBS containing 1% BSA, re-suspended in 200 μL PBS containing 1% BSA, and detected and analyzed by FACS (FACS Canto II, purchased from BD). The results are shown in FIG. 7A-FIG. 7F and Table 17-Table 19. The results show that, compared to wild-type IL-2, IL-2 mutants had similar effects on proliferation of Tregs, but slightly less effects on proliferation of CD4$^+$CD25$^-$FoxP3$^-$T cells or CD8$^+$T CD25$^-$T cells. The MFI in the following tables is the average fluorescence intensity value of Celltrace Violet in the detected cells, which was decreased in proliferated cells. That is, in the same detection time, the faster the cells proliferated, the lower the average fluorescence intensity was detected.

TABLE 17

Treg proliferation activated by IL-2 mutants detected by FACS

| | Protein concentration (nM) | | | | | | |
|---|---|---|---|---|---|---|---|
| | 10 | 1 | 0.1 | 0.01 | 0.001 | 0.0001 | 0.00001 |
| IL-2-linker2-hFc(MFI) | 1995 | 1670 | 2857 | 3362 | 3624 | 3863 | 4518 |
| Mut7.36-linker2-hFc(MFI) | 1823 | 1407 | 2070 | 3162 | 3555 | 4077 | 4389 |
| Mut7.66-linker2-hFc(MFI) | 1583 | 1437 | 2068 | 3384 | 4392 | 4027 | 4887 |
| IL-2-linker2-hFc(MFI) | 1807 | 1838 | 2651 | 3319 | 3459 | 3691 | 4758 |
| Mut11.08-linker2-hFc(MFI) | 1633 | 1536 | 1884 | 2371 | 2930 | 3369 | 3953 |
| Mut11.31-linker2-hFc(MFI) | 1735 | 1855 | 1985 | 2669 | 2626 | 3379 | 4323 |

TABLE 18

CD4$^+$CD25$^-$FoxP3$^-$T cell proliferation activated by IL-2 mutants detected by FACS

| | Protein concentration (nM) | | | | | | |
|---|---|---|---|---|---|---|---|
| | 10 | 1 | 0.1 | 0.01 | 0.001 | 0.0001 | 0.00001 |
| IL-2-linker2-hFc(MFI) | 1653 | 2058 | 2216 | 3198 | 4578 | 5274 | 5602 |
| Mut7.36-linker2-hFc(MFI) | 2361 | 2372 | 3317 | 4169 | 4971 | 5319 | 5815 |
| Mut7.66-linker2-hFc(MFI) | 2258 | 2524 | 3160 | 4633 | 5374 | 5495 | 6022 |

TABLE 18-continued

CD4+CD25−FoxP3−T cell proliferation activated
by IL-2 mutants detected by FACS

| | Protein concentration (nM) | | | | | | |
|---|---|---|---|---|---|---|---|
| | 10 | 1 | 0.1 | 0.01 | 0.001 | 0.0001 | 0.00001 |
| IL-2-linker2-hFc(MFI) | 1679 | 1838 | 2055 | 2728 | 3997 | 4826 | 5314 |
| Mut11.08-linker2-hFc(MFI) | 2254 | 2166 | 2538 | 3372 | 4154 | 5072 | 5391 |
| Mut11.31-linker2-hFc(MFI) | 2332 | 2559 | 2885 | 3878 | 4779 | 5284 | 5509 |

TABLE 19

CD8+T CD25−T cell proliferation activated by IL-2 mutants detected by FACS

| | Protein concentration (nM) | | | | | | |
|---|---|---|---|---|---|---|---|
| | 10 | 1 | 0.1 | 0.01 | 0.001 | 0.0001 | 0.00001 |
| IL-2-linker2-hFc(MFI) | 1128 | 1422 | 1696 | 3303 | 4907 | 5767 | 6303 |
| Mut7.36-linker2-hFc(MFI) | 1955 | 1921 | 2640 | 3732 | 4917 | 5562 | 6179 |
| Mut7.66-linker2-hFc(MFI) | 1820 | 1983 | 2683 | 4038 | 5539 | 5553 | 6617 |
| IL-2-linker2-hFc(MFI) | 1064 | 1236 | 1435 | 2497 | 4087 | 5010 | 5715 |
| Mut11.08-linker2-hFc(MFI) | 1876 | 1682 | 1956 | 2965 | 4124 | 5195 | 5567 |
| Mut11.31-linker2-hFc(MFI) | 1750 | 1945 | 2252 | 3463 | 4610 | 5406 | 5583 |

Example 11. Regulatory Effect of IL-2 Mutants on NK Cell Proliferation

Figure 8:
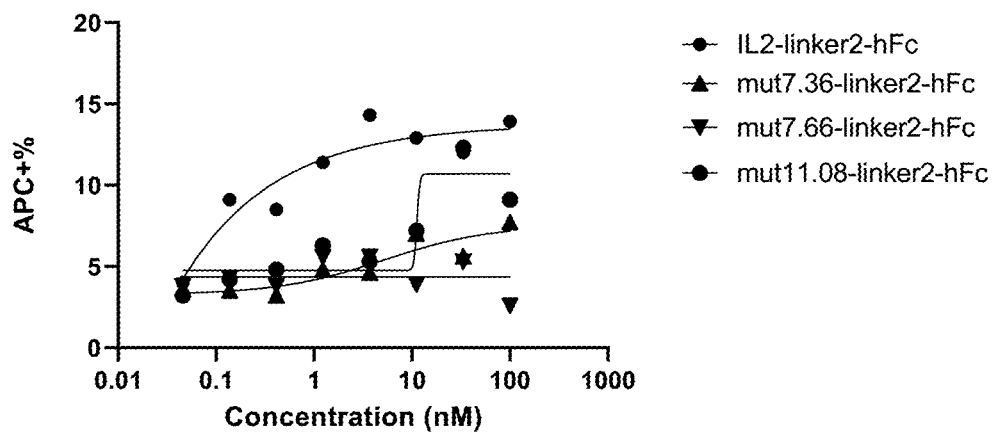
FIG. 8 shows the effect of IL-2 mutant protein on the level of proliferation of NK cells.
Figure 9A:
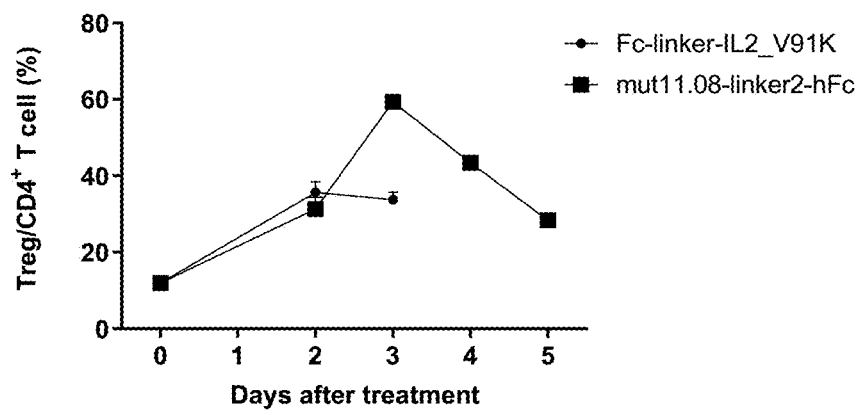
FIG. 9A shows the percentage of Tregs in $CD4^+$ T cells in the spleen.
Figure 9B:
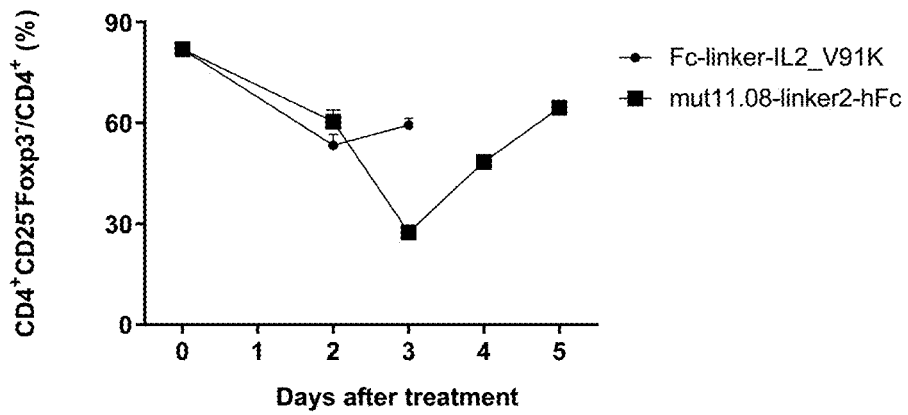
FIG. 9B shows the percentage of $CD4^+CD25^-Foxop3^-$ cells in $CD4^+$ cells in the spleen.
Figure 9C:
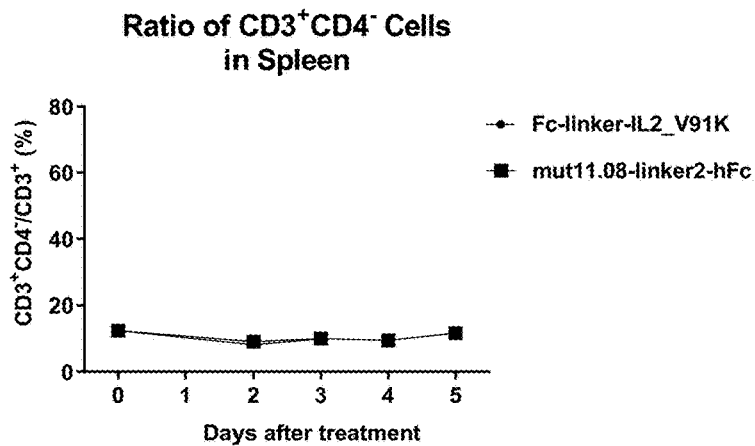
FIG. 9C shows the percentage of $CD3^+CD4^-$ cells in $CD3^+$ cells in the spleen.
Figure 10A:
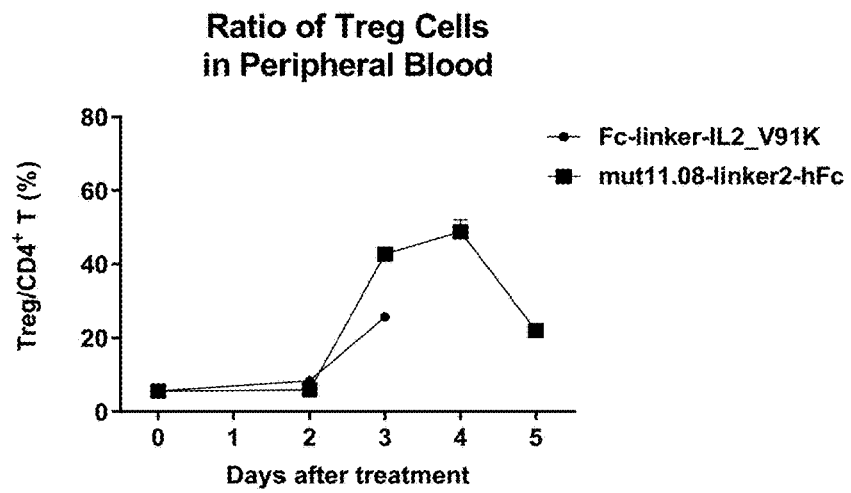
FIG. 10A shows the percentage of Tregs in $CD4^+$ cells in peripheral blood.
Figure 10B:
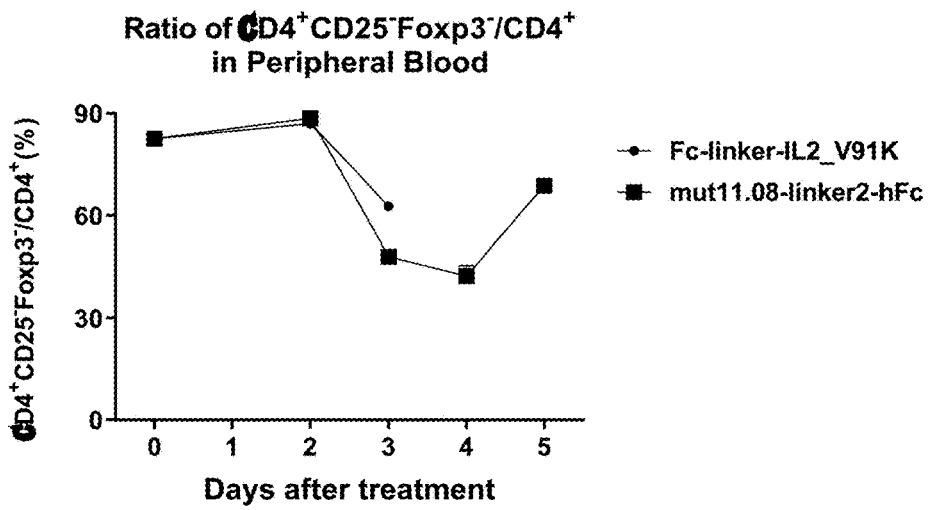
FIG. 10B shows the percentage of $CD4^+CD25^-Foxop3^-$ cells in $CD4^+$ cells in peripheral blood.
Figure 10C:
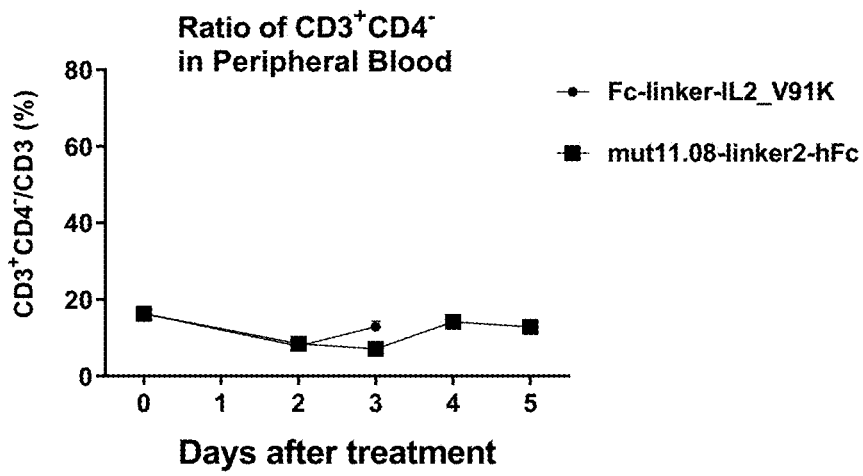
FIG. 10C shows the percentage of $CD3^+CD4^-$ cells in $CD3^+$ cells in peripheral blood.

NK cells were sorted and counted using an NK sorting kit (purchased from Miltenyi Biotec, Cat NO. 130-092-657), and then re-suspended in MEM medium (purchased from Gibco, Cat NO. 12634-010) comprising 25% bovine serum (purchased from Gibco, Cat NO. 10099-141C), 0.2 mM inositol (purchased from Sigma Aldrich, Cat NO. 17508-50G), 0.1 mM β-mercaptoethanol (purchased from Sigma Aldrich, Cat NO. M3148-100ML), and 0.02 mM folic acid (purchased from Sigma Aldrich, Cat NO. F8758-5G). The cells were seeded into a 96-well plate added with Fc blocker (purchased from Biolengend, Cat NO. 422302) and an IL-2 mutant in each well, and cultured for three days. BrdU (purchased from Biolengend, Cat NO. 423401) was added at the last 18 hours. The cells were collected, washed and re-suspended with PBS containing 1% BSA, fixed with an equal volume of 4% paraformaldehyde (purchased from DingGuo, Cat NO. AR-0211) at room temperature for 30 minutes, and washed with PBS containing 1% BSA. The cells were permeabilized with 0.5% Triton-X 100 (purchased from Thermo Fisher, Cat NO. HFH10) at room temperature for 15 minutes, washed with PBS containing 1% BSA, and digested with Dnase I (purchased from Sigma Aldrich, Cat NO. D4513-1VL) at 37° C. for one hour. The cells were washed and re-suspended with PBS containing 1% BSA, stained with APC anti-BrdU antibody (purchased from Biolengend, Cat NO. 339808) at room temperature for 20 minutes, and washed with PBS containing 1% BSA. The samples were re-suspended in 200 μL of PBS containing 1% BSA, detected and analyzed by FACS (FACS Canto II, purchased from BD). The results are shown in FIG. 8 and Table 20. The results show that, compared to wild-type IL-2, the effect of IL-2 mutants on NK cell proliferation was significantly reduced. The data in Table 20 is the proportion of BrdU positive cells in the NK cell population.

TABLE 20

NK cell proliferation activated by IL-2 mutants detected by FACS

| | Protein concentration (nM) | | | | | | | |
|---|---|---|---|---|---|---|---|---|
| | 100.00 | 33.33 | 11.11 | 3.70 | 1.23 | 0.41 | 0.14 | 0.05 |
| IL-2-linker2-hFc(APC + %) | 13.9 | 12.0 | 12.9 | 14.3 | 11.4 | 8.5 | 9.1 | 4.0 |
| Mut7.36-linker2-hFc(APC + %) | 7.7 | 5.6 | 7.0 | 4.6 | 4.8 | 3.2 | 3.5 | 3.6 |
| Mut7.66-linker2-hFc(APC + %) | 2.6 | 5.3 | 3.9 | 5.6 | 5.6 | 3.8 | 4.3 | 3.8 |
| Mut11.08-linker2-hFc(APC + %) | 9.1 | 12.3 | 7.2 | 5.3 | 6.3 | 4.8 | 4.2 | 3.2 |

Example 12. Pharmacodynamics (PD) Results in Wild-Type Mice after Subcutaneous Administration Balb/c mice, female, 6-8 weeks old, were purchased from Vital River. Fc-linker-IL2_V91K and mut11.08-linker2-hFc were diluted with PBS and administered subcutaneously to the back of mice at 200 μL per mouse. After administration, the whole blood and spleen samples of mice were collected at different time points for FACS analysis. The sequence of Fc-linker-IL2_V91K is as shown in SEQ ID NO: 61, which was purified as described in Example 2.

(SEQ ID NO: 60)
PKSSDKTHTCPPCPAPELLGGPSVFLFPPKPKDTLMISRTPEVTCVVVDV

SHEDPEVKFNWYVDGVEVHNAKTKPCEEQYGSTYRCVSVLTVLHQDWLNG

-continued
KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGGGGGSAPTSSSTKKTQLQLE

HLLLDLQMILNGINNYKNPKLTRMLTFKFYMPKKATELKHLQCLEEELKP

LEEVLNLAQSKNFHLRPRDLISNINKIVLELKGSETTFMCEYADETATIV

EFLNRWITFAQSIISTLT

The whole blood of mice was collected in a 2 mL EDTA/2K anticoagulant tube (Xinkang Medical, Cat. No. X424), and well mixed with the anticoagulant by upside down tilting the tube for full contact. 300 μL of whole blood was transferred to a FACS tube, which was added with a mixed solution of staining antibodies and incubated at room temperature in the dark for 20 min. The sample was then added with red blood cell lysis buffer (1 mL per sample) (Hybri-Max Cat. No. R7757-100 mL) and allowed to stand at room temperature in the dark for 5 min, and floccules were observed. The sample was then centrifuged at 400 g for 6 min at 20° C. After the supernatant was discarded, the cells were dispersed. Red blood cell lysis was repeated. Cell washing: the cells were re-suspended in PBS (4 mL per sample) and centrifuged at 500 g for 6 min at 4° C.; the supernatant was discarded; and the cells were dispersed. Fixation buffer (500 μL per tube) was added into the tube drop by drop, while shaking the FACS tube intermittently after each addition. The sample was fixed at 4° C. for an hour or overnight.

The spleens of mice were milled on a 70 μm cell strainer (Falcon Corning, Cat. No. 352350) and centrifuged at 500 g. Each spleen was added with 3 mL red blood cell lysis buffer and lysed for 5 min, and then added with 20 mL PBS to terminate the lysis. The mixture was centrifuged at 500 g for 5 min. The cells were re-suspended with 5 mL PBS and screened by a 70 μm cell strainer. After cell counting, 1×10⁶ cells were added into each FACS tube. After Fc Blocker (5 μL per tube) (Biolengend, Cat. No. 156 603) was added, the cells were vortexed and incubated at 4° C. for 20 min (vortexed every 10 min). The cells were then added with FACS washing buffer (4 mL per tube) (PBS+1% BSA) and centrifuged at 400 g for 6 min at 4° C. The supernatant was discarded and the mouth of the tube was dried with absorbent paper. The cells were added with Anti-Mouse CD3e (BD Bioscience, Cat. No. 740014), Anti-Mouse CD4 (BD Bioscience, Cat. No. 553407) and Anti-mouse CD25 (Biolengend, Cat. No. 102008), vortexed and incubated at 4° C. for 20 min (vortexed every 10 min). The cells were then added with FACS washing buffer (4 mL per tube) and centrifuged at 400 g for 6 min at 4° C. The supernatant was discarded and the mouth of the tube was dried with absorbent paper. After vortexing once, fixation buffer (500 μL per tube) was added into the tube drop by drop, while shaking the tube intermittently after each addition. The sample was fixed at 4° C. for an hour or overnight.

Fixation buffer: Fixation/Permeabilization Concentrate and Fixation/Permeabilization Diluent in Set3901 (eBioscience, Cat. No. 00-5523-00) were mixed in a ratio of 1:3 to prepare the fixation buffer.

Permeabilization buffer and ddH$_2$O were mixed well in a ratio of 1:9 to prepare the permeabilization solution. The cells were added with the permeabilization solution (2 mL per tube) and centrifuged at 500 g for 6 min at 4° C. The supernatant was discarded and the mouth of the tube was dried with absorbent paper. The permeabilization process was repeated with permeabilization solution (3 mL per tube). The cells were added with Foxp3 antibodies (10 μL per tube) (eBioscience, Cat. No. 25-5773-82) and kept at 4° C. for 40 min (vortexed every 20 min). The cells were then added with FACS buffer (4 mL per tube) and centrifuged at 500 g for 6 min at 4° C. The supernatant was discarded and the mouth of the tube was dried with absorbent paper. After vortexing once, 100 μL FACS buffer was added into the tube to re-suspend the cells for detection. The percentages of Tregs (CD4$^+$ CD25$^+$ Foxp3$^+$), CD4$^+$ CD25$^-$ Foxp3$^-$ and CD3$^+$CD4$^-$ T cells in groups of animals were represented as mean±standard deviation (Mean±SEM), and graphed and analyzed by Graphpad Prism 5 software.

As shown in FIG. 9A-9C and FIG. 10A-10C, when being administered subcutaneously at a single dose of 1 mpk, mut11.08-linker2-hFc significantly increased the percentage of Tregs and decreased the percentage of CD4$^+$ CD25$^-$ Foxp3$^-$ T cells in the spleen and peripheral blood of mice. The percentage of CD3$^+$CD4$^-$ T cells was not significantly changed. The efficacy of mut11.08-linker2-hFc was better than that of Fc-linker-IL2_V91K.

Example 13. Wild-Type Mice DTH (Delayed-Type Hypersensitivity) Model

Sensitization phase: Antigens were emulsified with 3 mg/mL KLH (Sigma, Cat. No. H7017, 50 mg), IFA (Sigma, Cat. No. F5506, 10 mL) and CFA (Sigma, Cat. No. F5581, 10 mL) in a volume ratio of 1:1:1 by using the Double-hubbed needle method. The antigens could be fully emulsified to form a viscous emulsion in about 1 hour. Each mouse was injected with 100 μL emulsifier, that is, 100 μg KLH. Each mouse was injected subcutaneously with emulsified KLH at two sites (50 μL at each site) in the middle part of scapula. At the same time, the mice were injected subcutaneously with WT IL-2-linker2-hFc (WT IL-2, SEQ ID NO: 12), Fc-linker-IL2_V91K or mut11.08-linker2-hFc at a dose of 1 mpk, 200 μL per mouse, once every 3 days, as WT IL-2-linker2-hFc, Fc-linker-IL2_V91K and mut11.08-linker2-hFc group, respectively; the mice were injected intraperitoneally with cyclosporin A (CsA, Sigma, Cat. No. F5581, 10 mL) at a dose of 10 mpk, 200 μL per mouse, once per day, as CsA group; the mice were injected intraperitoneally with PBS as vehicle control group.

Stimulation was performed on the 5th day after sensitization. 10 mg/mL KLH was diluted to 1 μg/μL by 10 times with PBS. Each mouse was injected intradermally with 10 μL KLH (i.e., 10 μg KLH) on right ear and 10 μL PBS on left ear as control.

Before sensitization, the left and right ears thickness of each mouse was measured by a spiral micrometer (0-25 mm, accuracy: 0.001, purchased from Nanjing SuCe Measuring Instruments Co., Ltd) and recorded. Before stimulation, the left and right ears thickness of each mouse was measured with the spiral micrometer as a baseline value. The ear thickness was measured at 24 h, 48 h, 72 h, and 96 h after stimulation. The changes of body weight and ear thickness in each group were represented as mean±standard deviation (Mean±SEM), and graphed and analyzed by Graphpad Prism 5 software.

Figure 11A:
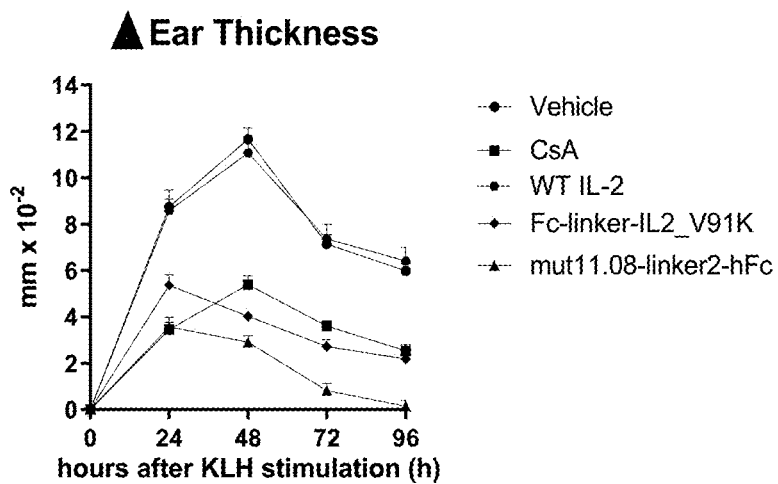
FIG. 11A shows the change of Δ ear thickness in different groups of wild-type mice DTH models, wherein Δ ear thickness refers to the change of thickness of the right ear before and after stimulation.
Figure 11B:
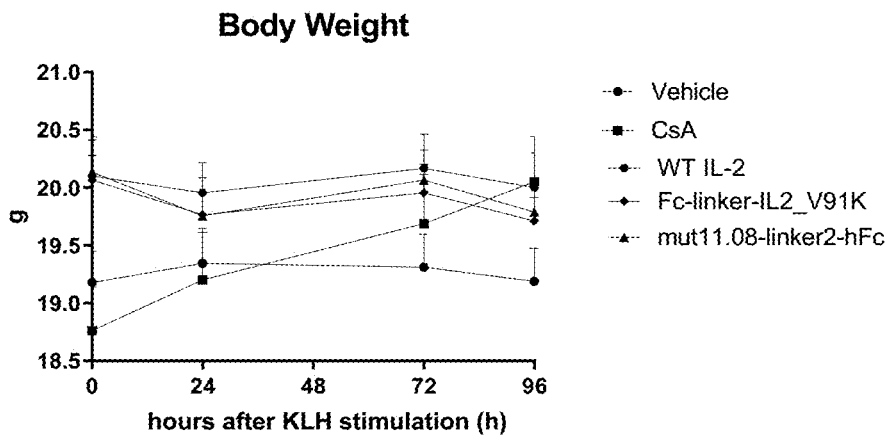
FIG. 11B shows the change of body weight in different groups of wild-type mice DTH models.

The result is shown in FIG. 11A. After a single subcutaneous administration of 1 mpk, compared to the vehicle control group, the change of Δ ear thickness in WT IL-2 group was not significant, while the Δ ear thickness of mice in mut11.08-linker2-hFc group became less, which suggests the anti-inflammatory effect of mut11.08-linker2-hFc, and the anti-inflammatory efficacy of mut11.08-linker2-hFc is better than that of Fc-linker-IL2 V91K and CsA. As shown in FIG. 11B, there was no significant change in the body weight of animals in the groups.

Figure 12A:
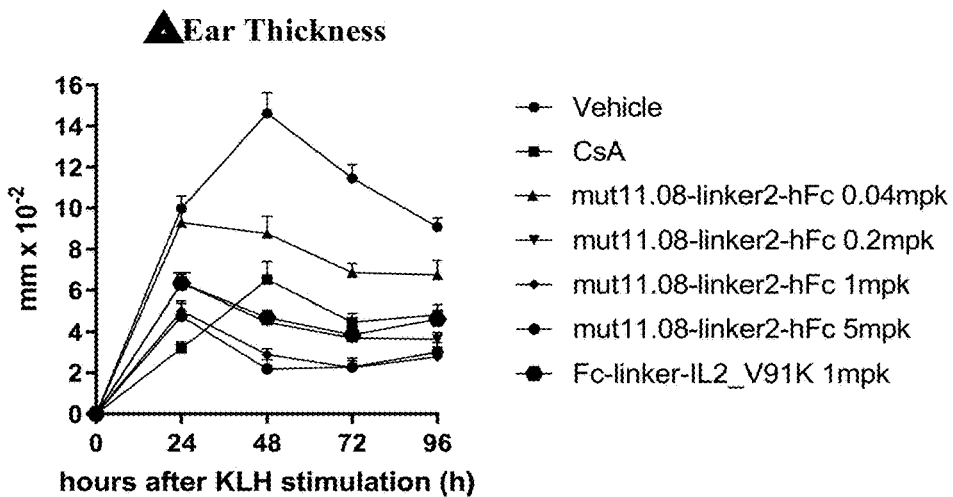
FIG. 12A shows the change of Δ ear thickness in different groups of wild-type mice DTH models, wherein Δ ear thickness refers to the change of thickness of the right ear before and after stimulation.
Figure 12B:
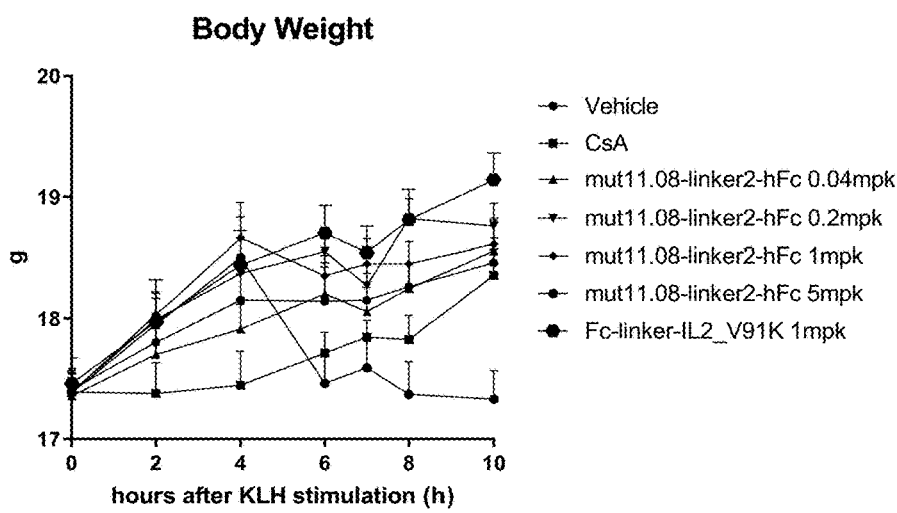
FIG. 12B shows the change of body weight in different groups of wild-type mice DTH models.
Figure 13A:
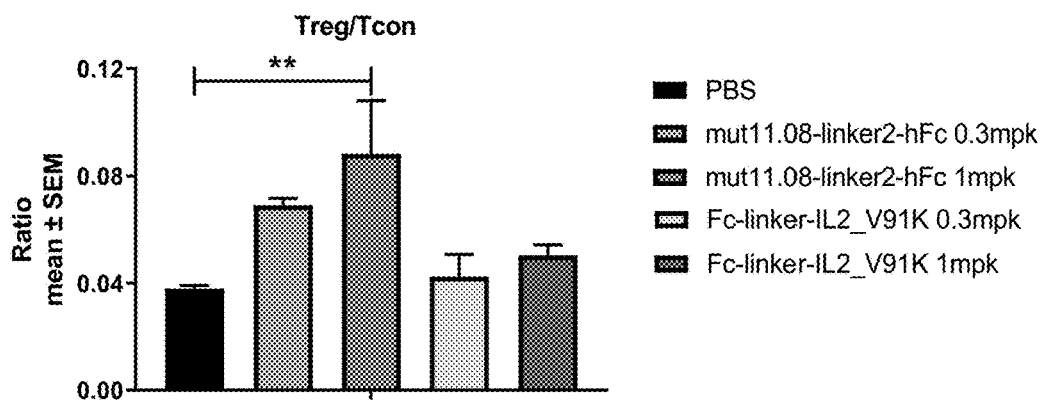
FIG. 13A shows Treg/Tcon in different groups of NOG mice.
Figure 13B:
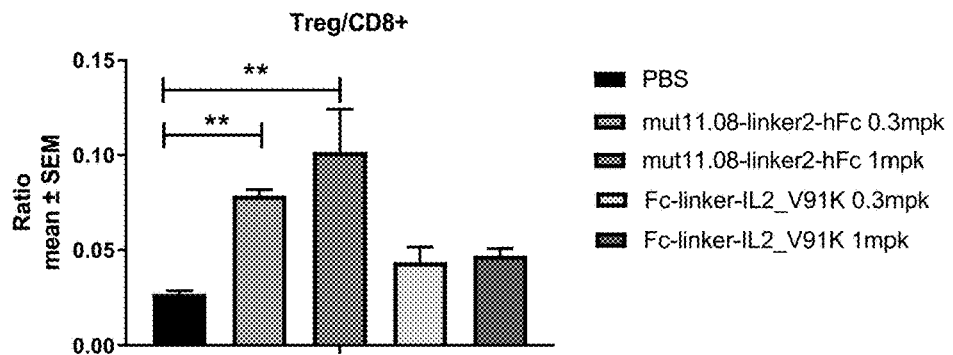
FIG. 13B shows Treg/$CD8^+$ in different groups of NOG mice.
Figure 14A:
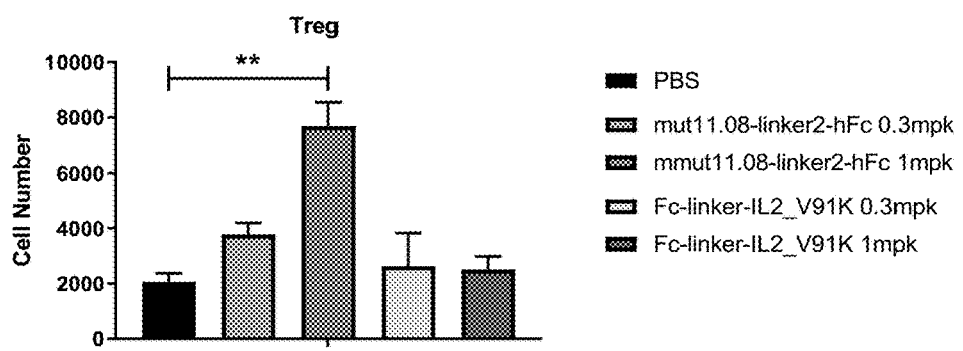
FIG. 14A shows the number of Tregs in different groups of NOG mice.
Figure 14B:
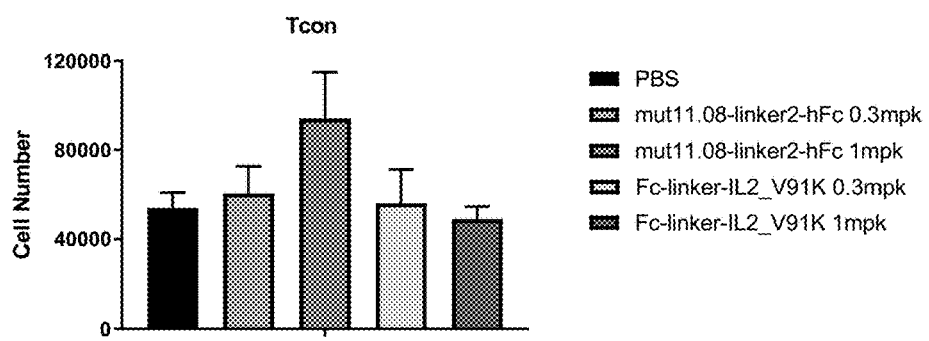
FIG. 14B shows the number of Tcons in different groups of NOG mice.
Figure 14C:
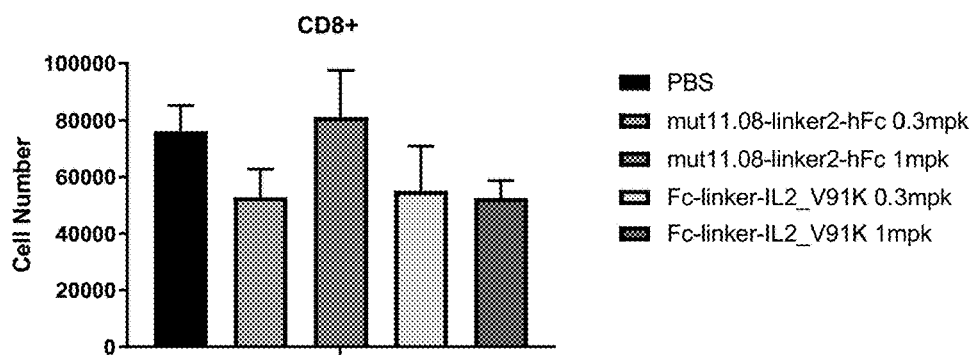
FIG. 14C shows the number of $CD8^+$ cells in different groups of NOG mice.

The results of the second round of experiments are shown in FIG. 12A. A single dose of Fc-linker-IL2_V91K (1 mpk) was administered subcutaneously, while mut11.08-linker2-hFc was administered subcutaneously at a single dose of 0.04, 0.2, 1 or 5 mpk. The anti-inflammatory effect of mut11.08-linker2-hFc was dose dependent. 0.2 mpk mut11.08-linker2-hFc had the same effect as 1 mpk Fc-linker-IL2_V91K, and no abnormality in body weight was observed under this condition. As shown in FIG. 12B, when 5 mpk mut11.08-linker2-hFc was administrated, the body weight of mice fluctuated and decreased, while the body weight of other groups was normal.

Example 14. PD Results in PBMC Mice after Subcutaneous Administration

NOG mice, female, 11-12 weeks old, were purchased from Vital River. On Day 1, PBMCs were thawed, activated by adding CD3 (purchased from eBioscience, Cat. No. 16-0037-85/2106800, with a final concentration of 12.5 ng/mL) and CD28 (purchased from eBioscience, Cat. No. 16-0289-85/2073954, with a final concentration of 25 ng/mL) and incubated overnight in a 5% $CO_2$ incubator at 37° C. for 16 hours. PBMCs ($20 \times 10^6$ per mouse, 400 µL) were collected on Day 0 and inoculated into NOG mice by tail veins. The inoculated mice were randomly divided into five groups based on body weight, including PBS control group, mut11.08-linker2-hFc groups (0.3 mpk, 1 mpk) and Fc-linker-IL2_V91K groups (0.3 mpk, 1 mpk), with 3 mice in each group. The drug was then injected subcutaneously into the neck (Day 0) in a single dose. On Day 3 after administration, the spleen of euthanized mice was taken for FACS analysis, and data were recorded. The number and the fold change of Tregs ($CD4^+$ $CD25^+$ $Foxp3^+$), Tcons ($CD4^+$ $CD25^-$) and $CD8^+$ T cells in the groups of animals were graphed and analyzed by Graphpad Prism 8 software.

The experimental results are shown in FIG. 13A-13B and FIG. 14A-14C. After a single subcutaneous administration of 1 mpk, mut11.08-linker2-hFc increased the ratio of Treg/Tcon and the ratio of Treg/$CD8^+$T on day 3 in a dose-dependent manner and showed a better result than Fc-linker-IL2_V91K. On Day 3 after administration, except for the significant change in the number of Tregs, the number of Tcons increased but was not significant, and the number of $CD8^+$T cells did not change significantly.

Example 15. PBMC Mice Graft-Versus-Host Disease (GVHD) Model

NOG mice, females, 13-14 weeks old, were purchased from Vital River. The protocol was same as Example 14. The NOG mice were randomly divided into three groups based on body weight, including G1 group (PBS, no activated PBMCs were inoculated, 3 mice), G2 group (PBS, 10 mice) and G3 group (0.2 mpk mut11.08-linker2-hFc was given, 10 mice), wherein G2 and G3 groups were inoculated with activated PBMCs according to Example 14. The drug was then injected subcutaneously into the neck (Day 0) in a single dose. The mice were weighed twice per week, and scored after the appearance of GVHD characteristics [Scoring System: weight loss (0: <10%, 1: 10%-20%, 2: >20%, 3: >30%); anemia (0: red or pink tail, 1: white tail); posture (0: normal, 1: hunchback); general activities (0: normal, 1: limited); shedding (0: without shedding, 1: shedding) and jaundice (0: white or red tail, 1: yellow tail); the maximum disease severity or death corresponds to 8]. The data were recorded. Note: 1. If a mouse gets the maximum disease severity score, other symptoms will not be scored; 2. After death, the dead mice were continually scored until the end of the experiment.

Figure 15A:
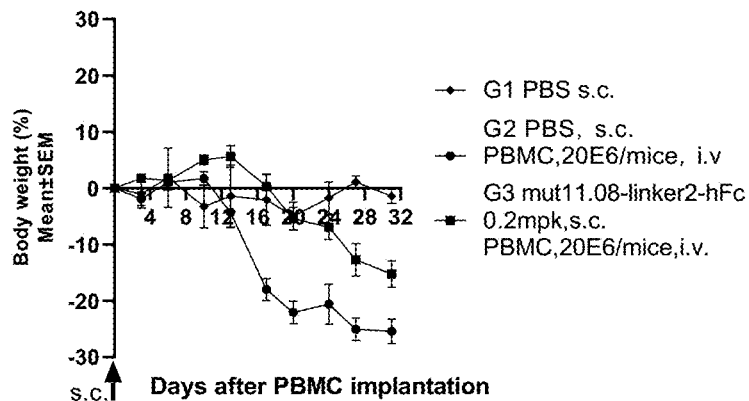
FIG. 15A shows the change of body weight in different groups of NOG mice.
Figure 15B:
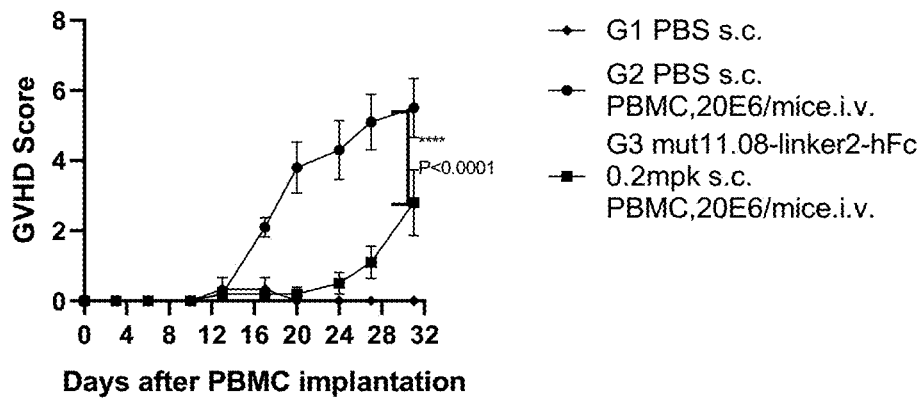
FIG. 15B shows the GVHD scores in different groups of NOG mice.

The experimental results are shown in FIG. 15A-15B. 13 days after PBMCs inoculation, the body weight of the G2 group decreased, and GVHD symptoms occurred early in the G2 group. 17 days after PBMCs inoculation, the body weight of the G3 group decreased, and the overall weight loss of the G3 group was less than that of the G1 group, and the weight loss of the G3 group occurred later than that of the G2 group, which suggests mut11.08-linker2-hFc effectively inhibits the occurrence of GVHD in mice in accordance with pharmacological expectation. The mut11.08-linker2-hFc showed no toxic and side effects at 0.2 mpk, and good anti-GVHD ability, according to the body weight assessment. In addition, the animal mortality and GVHD score of the G3 group were lower than those of the G2 group, and there were significant differences.

Example 16. Pharmacokinetics in Mice

The method for determining the plasma drug concentration in mice in this example was as follows: The plate was coated with 1 µg/mL hIL2R alpha protein (ACROBiosystems, Cat. No. ILA-H52H9-100 µg). A standard curve was formed with drugs in blank serum at concentrations ranging from 500 to 3.90625 ng/mL. Quality controls with high/medium/low concentrations were prepared, and all samples to be detected, standards and the quality controls were diluted 40 times with diluents and then added into a plate in duplicate (100 µl/well) (samples can be diluted additionally, according to the actual situation). The detection antibody Peroxidase AffiniPure Mouse Anti-Human IgG, Fc γ fragment specific (Jackson, Cat. No. 209-035-098) was diluted 10000 times and then added into the plate. The TMB chromogenic solution was added into the plate (100 µl/well) for color development, which was then stopped by using 1 M sulfuric acid (50 µl/well).

Figure 16A:
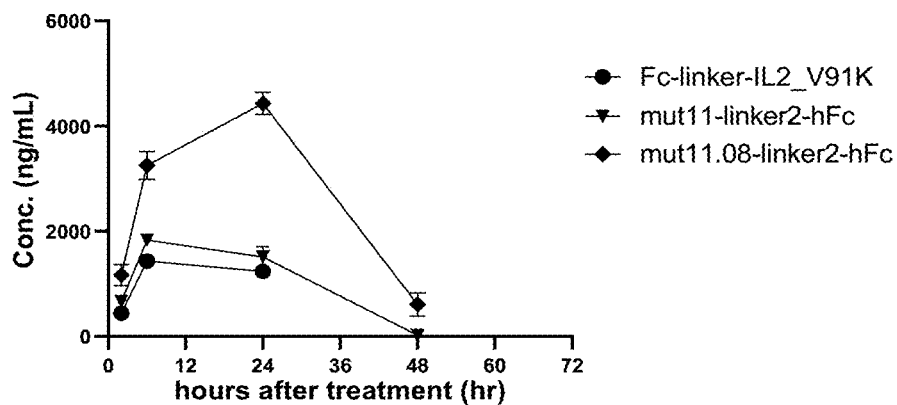
FIG. 16A shows the plasma drug concentration in wild-type mice after subcutaneous administration.
Figure 16B:
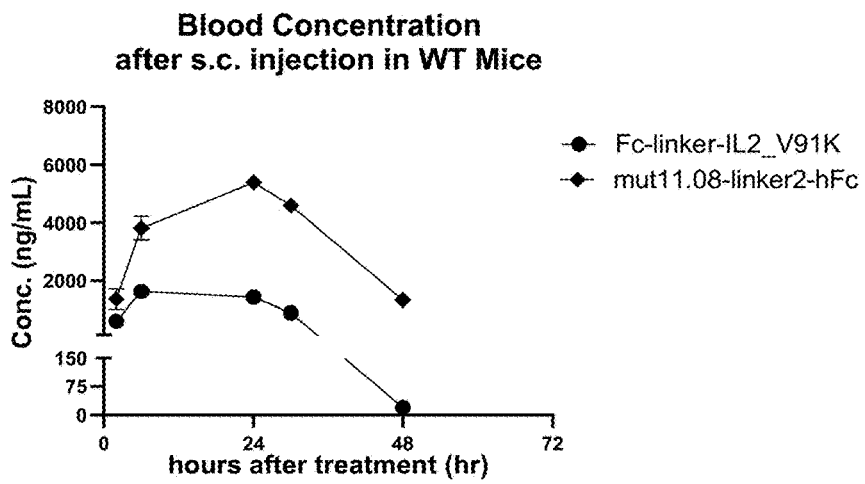
FIG. 16B shows the plasma drug concentration in wild-type mice after subcutaneous administration.

The plasma drug concentration in wild-type mice was determined after subcutaneous administration (1 mpk). The two experimental results are shown in FIG. 16A-16B and Table 21-22. In both experiments, the exposure amount of mut11.08-linker2-hFc was 4-6 times higher than that of Fc-linker-IL2_V91K (control group), and the $T_{max}$ was delayed compared to Fc-linker-IL2_V91K. The exposure amount of mut11.08-linker2-hFc was higher than that of mut11-linker2-hFc after a single subcutaneous administration (1 mpk).

TABLE 21

Pharmacokinetic parameters in wild-type mice after a single subcutaneous administration

| Mean | T1/2 (h) | $T_{max}$ (h) | $C_{max}$ (ng/mL) | AUClast (h*ng/mL) |
|---|---|---|---|---|
| Fc-linker-IL2_V91K | NA* | 6.00 | 1,430.94 | 28,208.77 |
| mut11-linker2-hFc | NA* | 12.00 | 1843.32 | 43,254.14 |
| mut11.08-linker2-hFc | NA* | 24.00 | 4,433.17 | 139,652.97 |

TABLE 22

Pharmacokinetic parameters in wild-type mice after a single subcutaneous administration

| Mean | T1/2 (h) | $T_{max}$ (h) | $C_{max}$ (ng/mL) | AUClast (h*ng/mL) |
|---|---|---|---|---|
| Fc-linker-IL2_V91K | NA* | 6.00 | 1628.30 | 42,874.91 |
| mut11.08-linker2-hFc | 11.51 | 24.00 | 5,391.62 | 177,902.19 |

Figure 17:
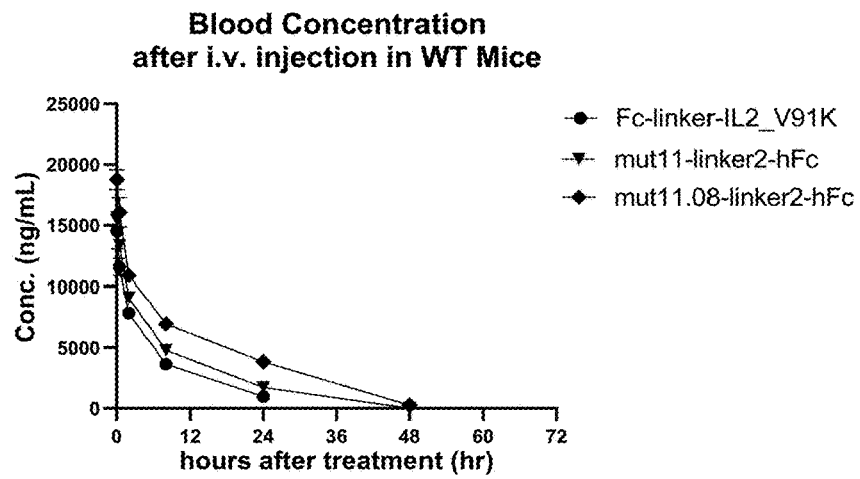
FIG. 17 shows the plasma drug concentration in wild-type mice after intravenous administration.

The plasma drug concentration in wild-type mice was determined after intravenous administration (1 mpk). The results are shown in FIG. 17 and Table 23. The exposure amount of mut11.08-linker2-hFc was higher than that of Fc-linker-IL2_V91K, but the difference became smaller ($C_{max}$: 3×→1.3×, AUC: 4×→2.4×) compared to subcutaneous administration. The exposure amount of mut11.08-linker2-hFc was higher than that of mut11-linker2-hFc, but the difference became smaller ($C_{max}$: 2.4×→1.2×, AUC: 3.2×→1.6×) compared to subcutaneous administration.

Therefore, the bioavailability of mut11.08-linker2-hFc administered subcutaneously was better than that of Fc-linker-IL2 V91K and mut11-linker2-hFc. Stability mutations increased drug exposure and bioavailability.

TABLE 23

Pharmacokinetic parameters in wild type mice after a single intravenous administration

| Mean | T1/2 (h) | $T_{max}$ (h) | $C_{max}$ (ng/mL) | AUClast (h*ng/mL) |
|---|---|---|---|---|
| Fc-linker-IL2_V91K | 7.35 | 0.08 | 14,518.61 | 92,522.67 |
| mut11-linker2-hFc | 5.27 | 0.08 | 15,450.84 | 138,450.96 |
| mut11.08-linker2-hFc | 8.41 | 0.08 | 18,761.22 | 217851.01 |

Figure 18:
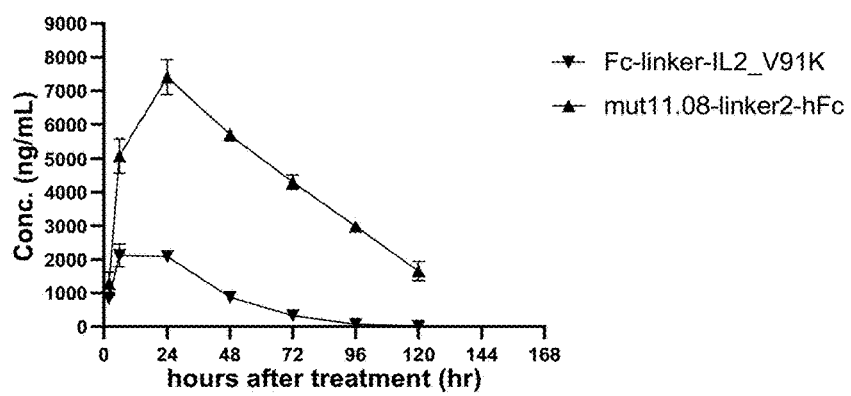
FIG. 18 shows the plasma drug concentration in mice inoculated with PBMCs after subcutaneous administration.

Mice were inoculated with PBMCs by the method described in Example 14. The plasma drug concentration in wild-type mice was determined after subcutaneous administration (1 mpk). The results are shown in FIG. 18 and Table 24. In PBMCs mice, after a single subcutaneous administration (1 mpk), the exposure amount of mut11.08-linker2-hFc showed an obvious advantage, which was 5-8 times higher than that of Fc-linker-IL2_V91K, and $T_{max}$ of mut11.08-linker2-hFc was later than that of Fc-linker-IL2_V91K.

TABLE 24

Pharmacokinetic parameters in PBMC mice after a single subcutaneous administration

| Mean | T1/2 (h) | $T_{max}$ (h) | $C_{max}$ (ng/mL) | AUClast (h*ng/mL) |
|---|---|---|---|---|
| Fc-linker-IL2_V91K | 12.29 | 12.00 | 2,338.82 | 99848.69 |
| mut11.08-linker2-hFc | 43.06 | 24.00 | 7,405.26 | 546719.71 |

Example 17. Pharmacokinetics and PD Results in Cynomolgus Monkeys

The method for determining the plasma drug concentration of cynomolgus monkeys in this example was as follow: The plate was coated with 1 μg/mL hIL2R alpha protein (ACROBiosystems, Cat. No. ILA-H52H9-100 μg). A standard curve was formed with drugs in blank serum from cynomolgus monkey at concentrations ranging from 15-0.11718 ng/mL. Quality controls with high/medium/low concentrations were prepared, and all samples to be detected, standards and the quality controls were diluted to 5 times and then added into the plate in duplicate (100 μl/well). The detection antibody Goat Anti-Human IgG, Monkey ads-BIOT (SoutherBiotech, Cat. No. 2049-08) was diluted 1000 times and then added into the plate, and then Streptavidin-HRP (Thermo, Cat. No. 21126) diluted 5000 times was added into the plate. Finally, the TMB chromogenic solution (100 μl/well) was added for color development, which was then stopped by using 1M sulfuric acid (50 μl/well). Cynomolgus monkey blank serum was purchased from Shanghai HkeyBio Technology Co., Ltd.

Figure 19:
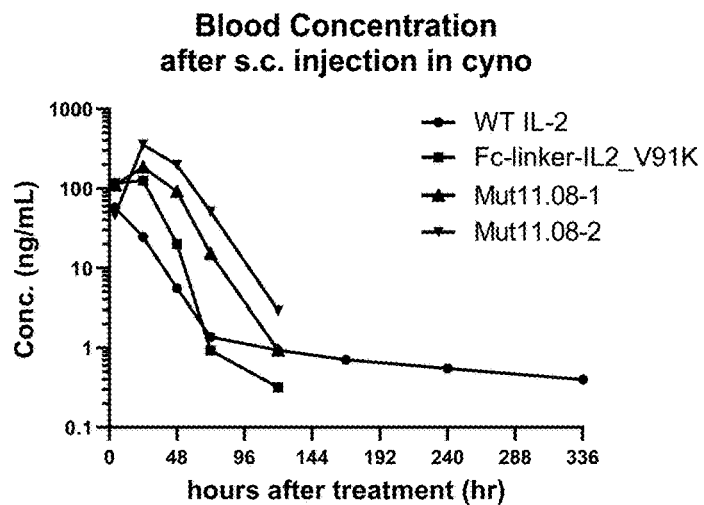
FIG. 19 shows the plasma drug concentration in cynomolgus monkey after subcutaneous administration.
Figure 20A:
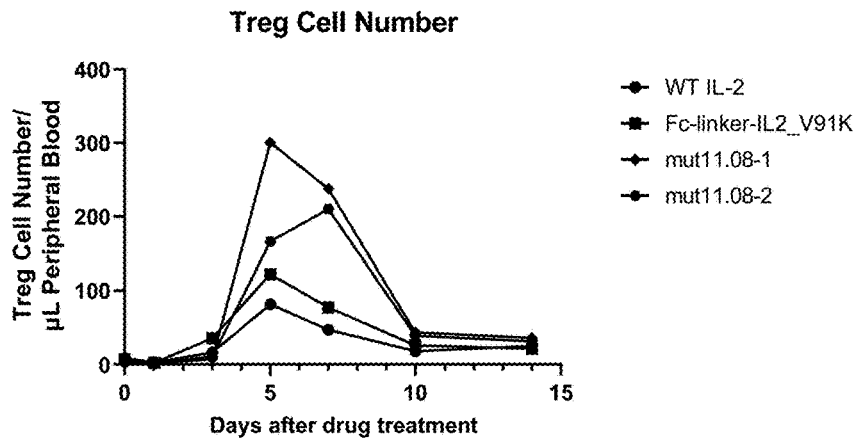
FIG. 20A shows the number of Tregs in cynomolgus monkeys after subcutaneous administration.
Figure 20B:
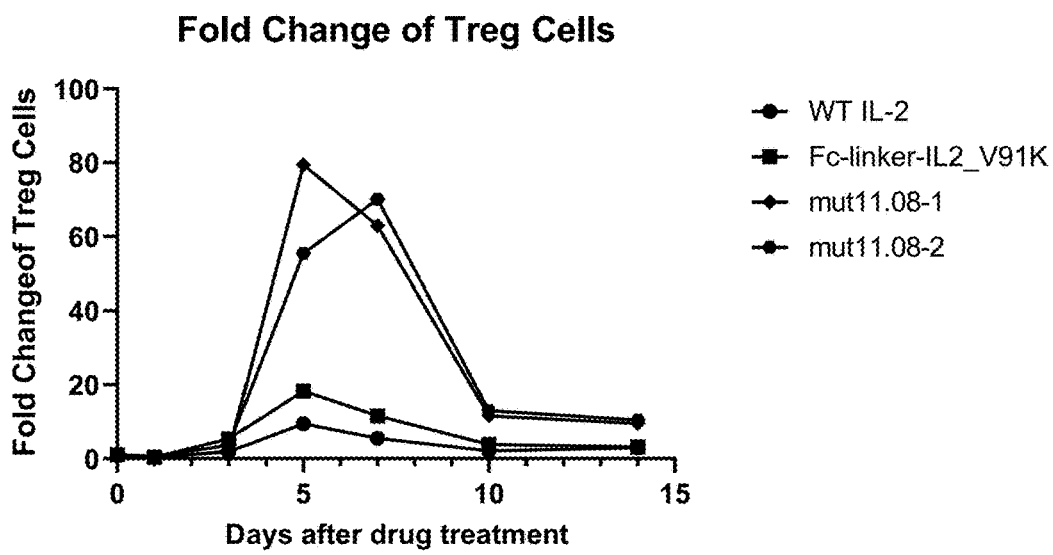
FIG. 20B shows the fold change of Treg number in cynomolgus monkeys after subcutaneous administration.
Figure 20C:
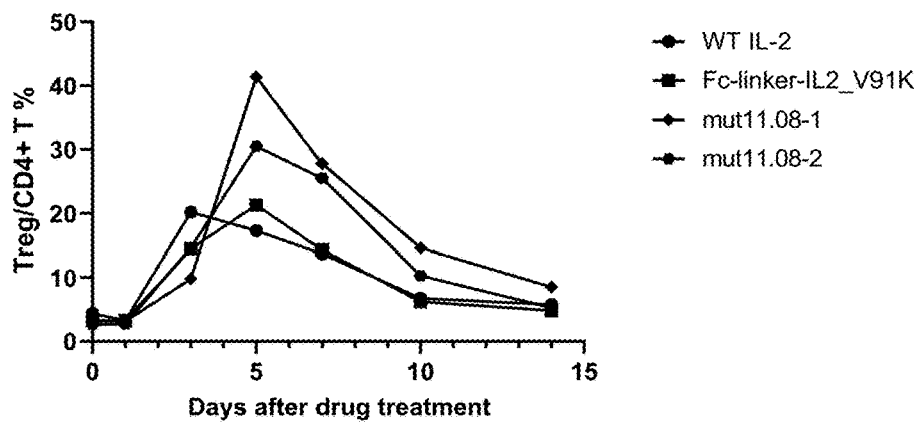
FIG. 20C shows the percentage of Tregs in CD4+ T cells in cynomolgus monkeys after subcutaneous administration.
Figure 20D:
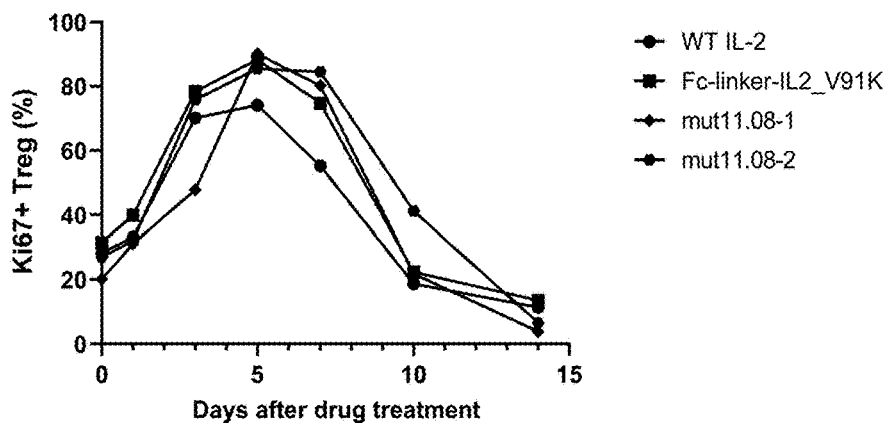
FIG. 20D shows the percentage of Ki67+ Tregs in cynomolgus monkeys after subcutaneous administration.
Figure 20E:
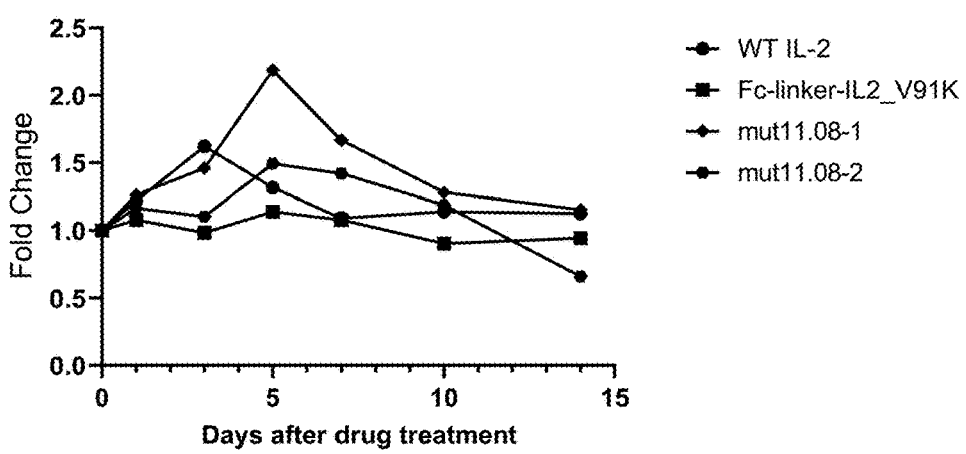
FIG. 20E shows the fold change of FoxP3 average fluorescence intensity in cynomolgus monkeys after subcutaneous administration.
Figure 20F:
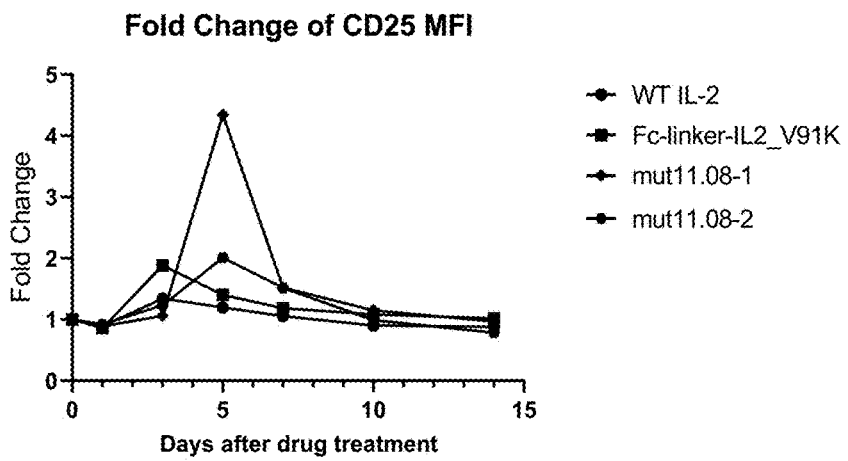
FIG. 20F shows the fold change of CD25 average fluorescence intensity in cynomolgus monkeys after subcutaneous administration.
Figure 21A:
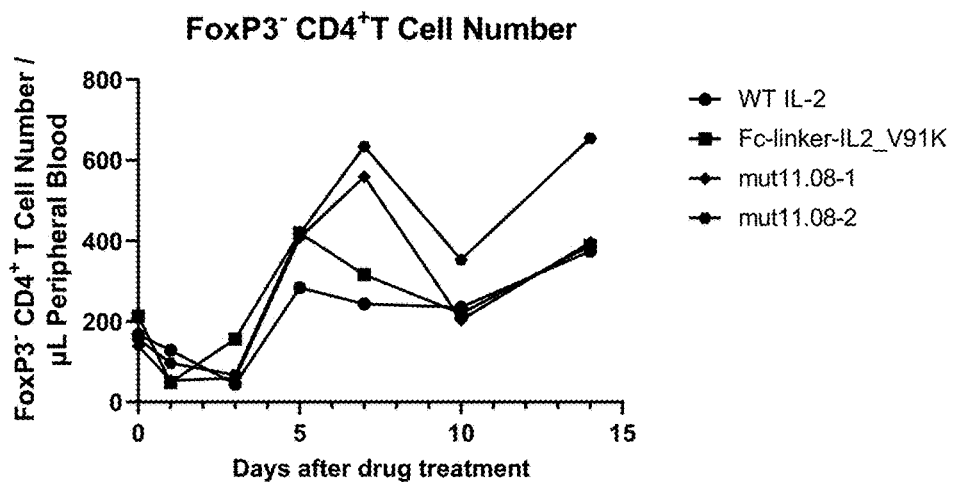
FIG. 21A shows the number of FoxP3−CD4+ cells in cynomolgus monkeys after subcutaneous administration.
Figure 21B:
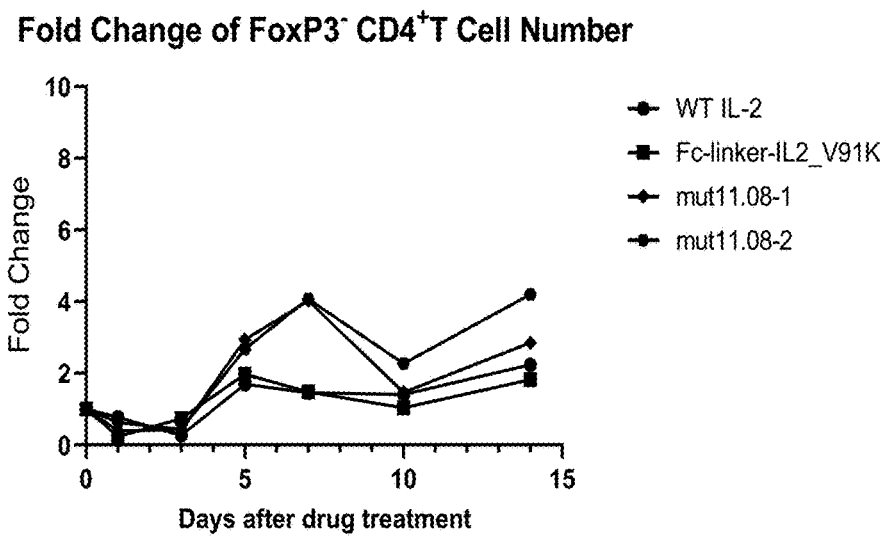
FIG. 21B shows the fold change of FoxP3−CD4+ cell number in cynomolgus monkeys after subcutaneous administration.
Figure 21C:
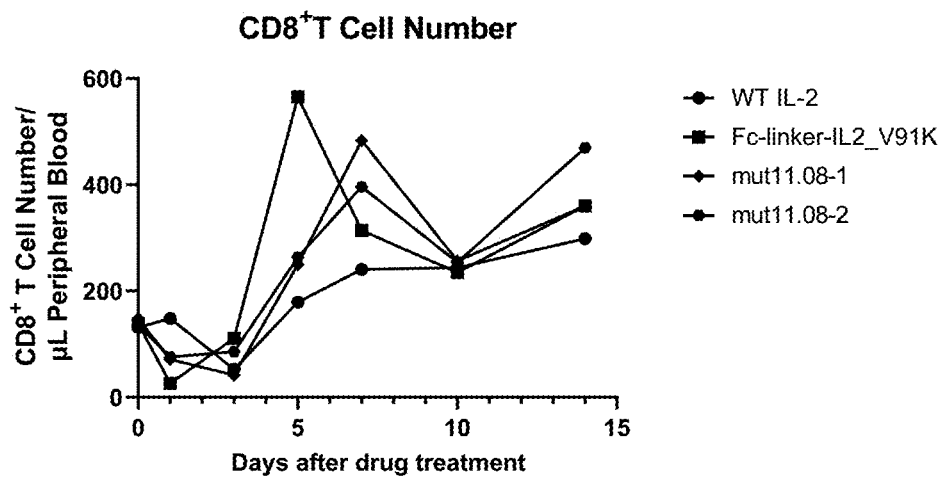
FIG. 21C shows the number of CD8+ T cells in cynomolgus monkeys after subcutaneous administration.
Figure 21D:
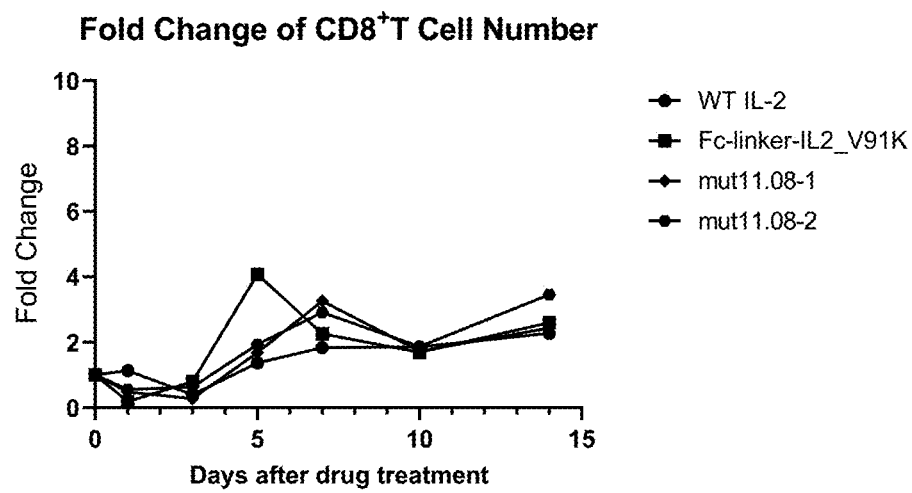
FIG. 21D shows the fold change of CD8+ T cell number in cynomolgus monkeys after subcutaneous administration.
Figure 21E:
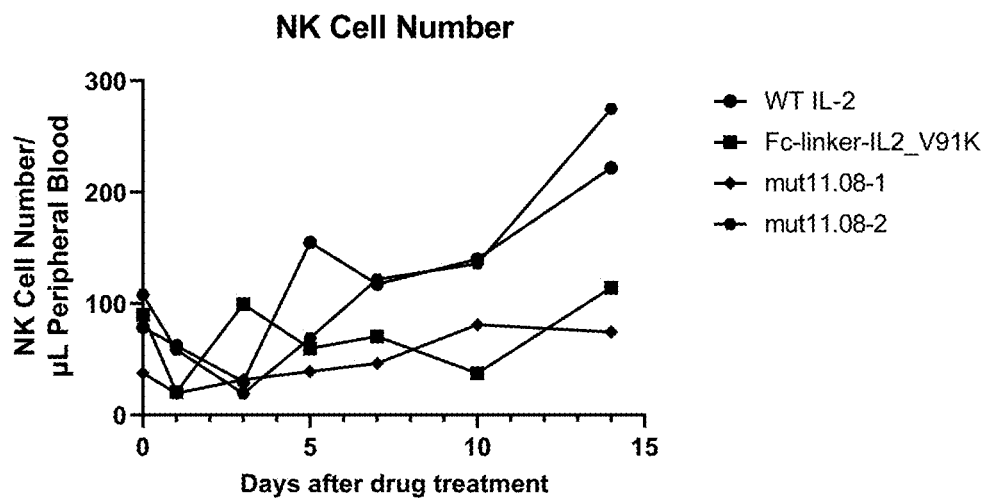
FIG. 21E shows the number of NK cells in cynomolgus monkeys after subcutaneous administration.
Figure 21F:
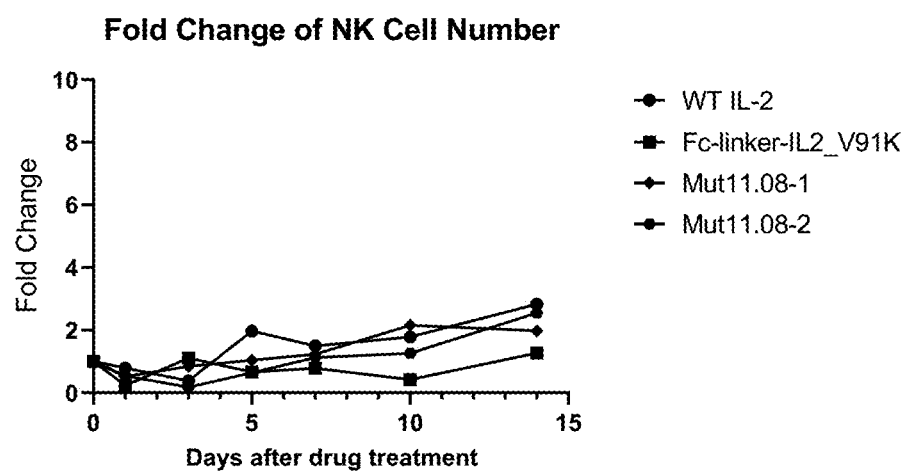
FIG. 21F shows the fold change of NK cell number in cynomolgus monkeys after subcutaneous administration.

4 cynomolgus monkeys were administered IL-2 subcutaneously at a dose of 0.05 mpk, of which 1 monkey was administered with WT IL-2-linker2-hFc (abbreviated as WT IL-2, as shown in SEQ ID NO: 12), 1 monkey was administered with Fc-linker-IL2_V91K, 2 monkeys were administered with mut11.08-linker2-hFc (abbreviated as Mut11.08-1 and Mut11.08-2, respectively), and the plasma drug concentration was detected after administration. The results are shown in FIG. 19 and Table 25. At the dose of 0.05 mpk, WT IL-2 molecule had a longer terminal half-life, and Fc-linker-IL2_V91K and mut11.08-linker2-hFc had a similar terminal half-life. The rank of $C_{max}$ and AUC was mut11.08-linker2-hFc >Fc-linker-IL2_V91K>WT IL-2.

TABLE 25

Pharmacokinetic parameters in cynomolgus monkey after a single subcutaneous administration

| Mean | T1/2 (h) | Tmax (h) | $C_{max}$ (ng/mL) | AUClast (h*ng/mL) |
|---|---|---|---|---|
| WT IL-2 | 204.97 | 4.00 | 57.70 | 1564.86 |
| Fc-linker-IL2_V91K | 13.20 | 24.00 | 125.07 | 4,669.24 |
| mut11.08-1 | 11.05 | 24.00 | 185.40 | 8,165.21 |
| mut11.08-2 | 11.80 | 24.00 | 355.50 | 15033.23 |

4 cynomolgus monkeys were used to determine the effect of a single subcutaneous administration of mut11.08-linker2-hFc on the expansion of Tregs from cynomolgus monkeys. 1 monkey was administered with WT IL-2-linker2-hFc, 1 monkey was administered with Fc-linker-IL2_V91K, and the other 2 monkeys were administered with mut11.08-linker2-hFc, at a dose of 0.05 mpk (by a single subcutaneous administration). The peripheral blood of cynomolgus monkeys was collected before administration and on Days 1, 3, 5, 7, 10 and 14 after administration. PBMCs were isolated from 2 mL blood sample of cynomolgus monkey collected at different time points and frozen. A vial of frozen PBMCs at each time point was taken and thawed for analysis together. The thawed PBMCs were re-suspended in 1 mL Staining Buffer (DPBS buffer containing 2% FBS), and then 200 μL each was transferred to two 96-well V-Bottom plates, which were labeled as Panel 1 and Panel 2. The two plates were washed once with PBS and then stained with Live/Dead Fixable Near-IR (Thermo, Cat. No. 134976) for 20 min. After staining was terminated by using Staining Buffer, Human TruStain FcX (Biolegend, Cat. No. 422302) was added into the plates and incubated for 20 min. Then the two plates were stained with mixtures of different fluorescent antibodies for 30 min. In panel 1, BV605 Mouse Anti-Human CD3 (BD, Cat. No. 562994), PerCP-Cy5.5 Mouse Anti-Human CD4 (BD, Cat. No. 552838), FITC Mouse Anti-Human CD8 (Biolegend, Cat. No. 301050) and BV421 Mouse Anti-Human CD25 (Biolegend, Cat. No. 302630) were diluted in Brilliant stain buffer (BD, Cat. No. 563794).

In panel 2, BV605 Mouse Anti-Human CD3 (BD, Cat. No. 562994), PerCP-Cy5.5 Mouse Anti-Human CD4 (BD, Cat. No. 552838), FITC Mouse Anti-Human CD8 (Biolegend, Cat. No. 301050) and Brilliant Violet 421 anti-human CD16 (Biolegend, Cat. No. 302038) were diluted in Brilliant stain buffer. The cells were washed once after staining was terminated, and fixed and permeabilized by using Foxp3/Transcription Factor Staining Buffer Kit (eBioscience, Cat. No. 00-5523-00). Mixtures of different fluorescent antibodies were added into the two plates to stain cells for 45 min. In panel 1, PE anti-human FOXP3 (Biolegend, Cat. No. 320208) and Ki67 Monoclonal Antibody APC (eBioscience, Cat. No. 17-5698-82) were diluted in Permeabilization Buffer. In panel 2, Ki67 Monoclonal Antibody APC was diluted in Permeabilization Buffer. After staining, the cells were washed once with Permeabilization Buffer and re-suspended with 400 μL Staining Buffer, and 200 μL samples were then analyzed by FACS. The number and the fold change of Tregs, CD4$^+$ Foxp3$^-$ T cells, CD8$^+$ T cells and NK cells in the groups of animals were graphed and analyzed by Graphpad Prism 9 software.

The experimental results are shown in FIG. 20A-20F. After a single subcutaneous administration (0.05 mpk), mut11.08-linker2-hFc significantly increased the number and percentage of Tregs in peripheral blood of cynomolgus monkeys. According to the ratio of Tregs/CD4$^+$T, mut11.08-linker2-hFc favored Treg activation, and thus the percentage of Tregs was about 2 times that of Fc-linker-IL2_V91K. Compared to Fc-linker-IL2_V91K, mut11.08-linker2-hFc showed a greater effect on increasing the proliferation of Tregs (11.08 vs Fc-linker-IL2_V91K=79/55 vs 18), while Fc-linker-IL2_V91K was better than WT (18 vs 9.5) in this respect. According to the analysis of Treg activation markers, there was little difference among Ki67$^+$ Treg % after administration of different molecules. The expression of Treg activation markers (Foxp3 and CD25) increased significantly, which was positively correlated with the proliferation level of Tregs.

As shown in FIG. 21A-21F, after a single subcutaneous administration of Fc-linker-IL2_V91K (0.05 mpk), the maximum fold change of FoxoP3$^-$CD4$^+$T cells was about 2 times, and that of CD8$^+$T cells was slightly higher, about 4 times. The effect of mut11.08-linker2-hFc on proliferation of FoxoP3$^-$CD4$^+$T cells was about 2-3 times greater than that of Fc-linker-IL2_V91K, while the effect on the proliferation of CD8$^+$T cell was slightly weaker than or similar to that of Fc-linker-IL2_V91K and was about 1.5-2 times than that of WT. The number of NK cells had not changed significantly after the administration of Fc-linker-IL2_V91K. The effect of mut11.08-linker2-hFc on proliferation level of NK was similar to that of Fc-linker-IL2_V91K.

SEQUENCE LISTING

```
Sequence total quantity: 61
SEQ ID NO: 1              moltype = AA  length = 133
FEATURE                   Location/Qualifiers
source                    1..133
                          mol_type = protein
                          organism = Homo sapiens
SEQUENCE: 1
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFAQSIIS TLT                                                   133

SEQ ID NO: 2              moltype = AA  length = 133
FEATURE                   Location/Qualifiers
source                    1..133
                          mol_type = protein
                          organism = synthetic construct
SEQUENCE: 2
APTSSSTKKT QLQLEHLLLD LQMILNGINN VKNPKLTRML TFKFYMPKKA TELKHLQCLE  60
EELKPLEEVL NLLQSKNFQL RPRDLISNIN VIVLELKGSE TTFMCEYADE TATIVEFLNR 120
WITFAQSIIS TLT                                                   133

SEQ ID NO: 3              moltype = AA  length = 133
FEATURE                   Location/Qualifiers
source                    1..133
                          mol_type = protein
                          organism = synthetic construct
SEQUENCE: 3
APTSSSTKKT QLLLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFAQSIIS TLT                                                   133

SEQ ID NO: 4              moltype = AA  length = 133
FEATURE                   Location/Qualifiers
source                    1..133
                          mol_type = protein
                          organism = synthetic construct
SEQUENCE: 4
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNF 120
WITFAQSIIS TLT                                                   133

SEQ ID NO: 5              moltype = AA  length = 133
FEATURE                   Location/Qualifiers
source                    1..133
                          mol_type = protein
```

```
                        organism = synthetic construct
SEQUENCE: 5
APTSSSTKKT QLQLEHLILD LQMILNGINN YKNPKLTRML TFKFYMPKKA TELKHLQCLE    60
EELKPLEEVL NLAQSKNFHL RPRDLISNIN AIVLELKGSE TTFMCEYADE TATIVEWLNR   120
WITFAQSIIS TLT                                                     133

SEQ ID NO: 6            moltype = AA   length = 133
FEATURE                 Location/Qualifiers
source                  1..133
                        mol_type = protein
                        organism = synthetic construct
SEQUENCE: 6
APTSSSTKKT QLQLEHLILD LQMILNGINN YKNPKLTRML TFKFYMPKKA TELKHLQCLE    60
EELKPLEEVL NLAQSKNFHL RPRDLISNLN VIILELKGSE TTFMCEYADE TATIVEFLNR   120
WITFAQSIIS TLT                                                     133

SEQ ID NO: 7            moltype = AA   length = 133
FEATURE                 Location/Qualifiers
source                  1..133
                        mol_type = protein
                        organism = synthetic construct
SEQUENCE: 7
APTSSSTKKT QLQLEHLLLD LQMILNWINN YKNPKLTRML TFKFYMPKKA TELKHLQCLE    60
EELKPLEEVL NLAQSKNFHL RPRDLISNIN VIVLELKGSE TTFMCEYADE TATIVEFLNF   120
WITFAQSIIS TLT                                                     133

SEQ ID NO: 8            moltype = AA   length = 133
FEATURE                 Location/Qualifiers
source                  1..133
                        mol_type = protein
                        organism = synthetic construct
SEQUENCE: 8
APTSSSTKKT QLQLEHLLLD LQMILNGINN YKNPKLTRML TFKFYMPKKA TELKHLQCLE    60
EELKPLEEVL NLAQSKNFHL RLRDLISNIN VIVLELKGSE TTFMCEYADE TATIVEFLNF   120
WITFAQSIIS TLT                                                     133

SEQ ID NO: 9            moltype = AA   length = 133
FEATURE                 Location/Qualifiers
source                  1..133
                        mol_type = protein
                        organism = synthetic construct
SEQUENCE: 9
APTSSSTKKT QLQLEHLLLD LQMILNGINN YKNPKLTRML TFKFYMPKKA TELKHLQCLE    60
EELKPLEEVL NLAQSKNFHL RPRDLISNIY VIVLELKGSE TTFMCEYADE TATIVEFLNF   120
WITFAQSIIS TLT                                                     133

SEQ ID NO: 10           moltype = AA   length = 15
FEATURE                 Location/Qualifiers
source                  1..15
                        mol_type = protein
                        organism = synthetic construct
SEQUENCE: 10
GGGGSGGGGS GGGGS                                                    15

SEQ ID NO: 11           moltype = AA   length = 232
FEATURE                 Location/Qualifiers
source                  1..232
                        mol_type = protein
                        organism = synthetic construct
SEQUENCE: 11
EPKSSDKTHT CPPCPAPELL GGPSVFLFPP KPKDTLMISR TPEVTCVVVD VSHEDPEVKF    60
NWYVDGVEVH NAKTKPREEQ YGSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 12           moltype = AA   length = 380
FEATURE                 Location/Qualifiers
source                  1..380
                        mol_type = protein
                        organism = synthetic construct
SEQUENCE: 12
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380
```

```
SEQ ID NO: 13              moltype = AA   length = 380
FEATURE                    Location/Qualifiers
source                     1..380
                           mol_type = protein
                           organism = synthetic construct
SEQUENCE: 13
APTSSSTKKT QLQLEHLLLD LQMILNGINN VKNPKLTRML TFKFYMPKKA TELKHLQCLE   60
EELKPLEEVL NLLQSKNFQL RPRDLISNIN IVIVLELKGSE TTFMCEYADE TATIVEFLNR  120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 14              moltype = AA   length = 380
FEATURE                    Location/Qualifiers
source                     1..380
                           mol_type = protein
                           organism = synthetic construct
SEQUENCE: 14
APTSSSTKKT QLLLEHLLLD LQMILNGINN YKNPKLTRML TFKFYMPKKA TELKHLQCLE   60
EELKPLEEVL NLAQSKNFHL RPRDLISNIN IVIVLELKGSE TTFMCEYADE TATIVEFLNR  120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 15              moltype = AA   length = 380
FEATURE                    Location/Qualifiers
source                     1..380
                           mol_type = protein
                           organism = synthetic construct
SEQUENCE: 15
APTSSSTKKT QLQLEHLLLD LQMILNGINN YKNPKLTRML TFKFYMPKKA TELKHLQCLE   60
EELKPLEEVL NLAQSKNFHL RPRDLISNIN IVIVLELKGSE TTFMCEYADE TATIVEFLNF  120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 16              moltype = AA   length = 380
FEATURE                    Location/Qualifiers
source                     1..380
                           mol_type = protein
                           organism = synthetic construct
SEQUENCE: 16
APTSSSTKKT QLQLEHLILD LQMILNGINN YKNPKLTRML TFKFYMPKKA TELKHLQCLE   60
EELKPLEEVL NLAQSKNFHL RPRDLISNIN AIVLELKGSE TTFMCEYADE TATIVEWLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 17              moltype = AA   length = 380
FEATURE                    Location/Qualifiers
source                     1..380
                           mol_type = protein
                           organism = synthetic construct
SEQUENCE: 17
APTSSSTKKT QLQLEHLILD LQMILNGINN YKNPKLTRML TFKFYMPKKA TELKHLQCLE   60
EELKPLEEVL NLAQSKNFHL RPRDLISNLN VIILELKGSE TTFMCEYADE TATIVEFLNR  120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 18              moltype = AA   length = 380
FEATURE                    Location/Qualifiers
source                     1..380
                           mol_type = protein
                           organism = synthetic construct
SEQUENCE: 18
APTSSSTKKT QLQLEHLLLD LQMILNWINN YKNPKLTRML TFKFYMPKKA TELKHLQCLE   60
EELKPLEEVL NLAQSKNFHL RPRDLISNIN VIVLELKGSE TTFMCEYADE TATIVEFLNF  120
WITFAQSIIS TLTGGGGSGG GGSGGGGSEP KSSDKTHTCP PCPAPELLGG PSVFLFPPKP   180
```

```
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 19          moltype = AA  length = 380
FEATURE                Location/Qualifiers
source                 1..380
                       mol_type = protein
                       organism = synthetic construct
SEQUENCE: 19
APTSSSTKKT QLQLEHLLLD LQMILNGINN YKNPKLTRML TFKFYMPKKA TELKHLQCLE    60
EELKPLEEVL NLAQSKNFHL RLRDLISNIN VIVLELKGSE TTFMCEYADE TATIVEFLNF   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 20          moltype = AA  length = 380
FEATURE                Location/Qualifiers
source                 1..380
                       mol_type = protein
                       organism = synthetic construct
SEQUENCE: 20
APTSSSTKKT QLQLEHLLLD LQMILNGINN YKNPKLTRML TFKFYMPKKA TELKHLQCLE    60
EELKPLEEVL NLAQSKNFHL RPRDLISNIY VIVLELKGSE TTFMCEYADE TATIVEFLNF   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 21          moltype = AA  length = 133
FEATURE                Location/Qualifiers
source                 1..133
                       mol_type = protein
                       organism = synthetic construct
SEQUENCE: 21
APTSSSTKKT QLQLEELLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFAQSIIS TLT                                                     133

SEQ ID NO: 22          moltype = AA  length = 133
FEATURE                Location/Qualifiers
source                 1..133
                       mol_type = protein
                       organism = synthetic construct
SEQUENCE: 22
APTSSSTKKT QLQLEELLLD LQMILNGINN VKNPKLTRML TFKFYMPKKA TELKHLQCLE    60
EELKPLEEVL NLLQSKNFQL RPRDLISNIN VIVLELKGSE TTFMCEYADE TATIVEFLNR   120
WITFAQSIIS TLT                                                     133

SEQ ID NO: 23          moltype = AA  length = 133
FEATURE                Location/Qualifiers
source                 1..133
                       mol_type = protein
                       organism = synthetic construct
SEQUENCE: 23
APTSSSTKKT QLQLEELLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNF   120
WITFAQSIIS TLT                                                     133

SEQ ID NO: 24          moltype = AA  length = 133
FEATURE                Location/Qualifiers
source                 1..133
                       mol_type = protein
                       organism = synthetic construct
SEQUENCE: 24
APTSSSTKKT QLQLEELILD LQMILNGINN YKNPKLTRML TFKFYMPKKA TELKHLQCLE    60
EELKPLEEVL NLAQSKNFHL RPRDLISNIN AIVLELKGSE TTFMCEYADE TATIVEWLNR   120
WITFAQSIIS TLT                                                     133

SEQ ID NO: 25          moltype = AA  length = 133
FEATURE                Location/Qualifiers
source                 1..133
                       mol_type = protein
                       organism = synthetic construct
SEQUENCE: 25
```

```
APTSSSTKKT QLQLEELILD LQMILNGINN YKNPKLTRML TFKFYMPKKA TELKHLQCLE    60
EELKPLEEVL NLAQSKNFHL RPRDLISNLN VIILELKGSE TTFMCEYADE TATIVEFLNR   120
WITFAQSIIS TLT                                                     133

SEQ ID NO: 26          moltype = AA   length = 133
    FEATURE                Location/Qualifiers
    source                 1..133
                           mol_type = protein
                           organism = synthetic construct
SEQUENCE: 26
APTSSSTKKT QLQLEELLLD LQMILNWINN YKNPKLTRML TFKFYMPKKA TELKHLQCLE    60
EELKPLEEVL NLAQSKNFHL RPRDLISNIN VIVLELKGSE TTFMCEYADE TATIVEFLNF   120
WITFAQSIIS TLT                                                     133

SEQ ID NO: 27          moltype = AA   length = 133
    FEATURE                Location/Qualifiers
    source                 1..133
                           mol_type = protein
                           organism = synthetic construct
SEQUENCE: 27
APTSSSTKKT QLQLEELLLD LQMILNGINN YKNPKLTRML TFKFYMPKKA TELKHLQCLE    60
EELKPLEEVL NLAQSKNFHL RLRDLISNIN VIVLELKGSE TTFMCEYADE TATIVEFLNF   120
WITFAQSIIS TLT                                                     133

SEQ ID NO: 28          moltype = AA   length = 133
    FEATURE                Location/Qualifiers
    source                 1..133
                           mol_type = protein
                           organism = synthetic construct
SEQUENCE: 28
APTSSSTKKT QLQLEHLLLA LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFAQSIIS TLT                                                     133

SEQ ID NO: 29          moltype = AA   length = 133
    FEATURE                Location/Qualifiers
    source                 1..133
                           mol_type = protein
                           organism = synthetic construct
SEQUENCE: 29
APTSSSTKKT QLQLEHLLLA LQMILNGINN VKNPKLTRML TFKFYMPKKA TELKHLQCLE    60
EELKPLEEVL NLLQSKNFQL RPRDLISNIN VIVLELKGSE TTFMCEYADE TATIVEFLNR   120
WITFAQSIIS TLT                                                     133

SEQ ID NO: 30          moltype = AA   length = 133
    FEATURE                Location/Qualifiers
    source                 1..133
                           mol_type = protein
                           organism = synthetic construct
SEQUENCE: 30
APTSSSTKKT QLQLEHLLLA LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNF   120
WITFAQSIIS TLT                                                     133

SEQ ID NO: 31          moltype = AA   length = 133
    FEATURE                Location/Qualifiers
    source                 1..133
                           mol_type = protein
                           organism = synthetic construct
SEQUENCE: 31
APTSSSTKKT QLQLEHLLLD LQMILNGINN YKNPKLTRML TFKFYMPKKA TELKHLQCLE    60
EELKPLEEVL NLAQSKNFHL RPRDLISNIN RIVLELKGSE TTFMCEYADE TATIVEFLNR   120
WITFAQSIIS TLT                                                     133

SEQ ID NO: 32          moltype = AA   length = 133
    FEATURE                Location/Qualifiers
    source                 1..133
                           mol_type = protein
                           organism = synthetic construct
SEQUENCE: 32
APTSSSTKKT QLQLEHLLLD LQMILNGINN VKNPKLTRML TFKFYMPKKA TELKHLQCLE    60
EELKPLEEVL NLLQSKNFQL RPRDLISNIN RIVLELKGSE TTFMCEYADE TATIVEFLNR   120
WITFAQSIIS TLT                                                     133

SEQ ID NO: 33          moltype = AA   length = 133
    FEATURE                Location/Qualifiers
    source                 1..133
                           mol_type = protein
                           organism = synthetic construct
```

```
SEQUENCE: 33
APTSSSTKKT QLLLEHLLLD LQMILNGINN YKNPKLTRML TFKFYMPKKA TELKHLQCLE    60
EELKPLEEVL NLAQSKNFHL RPRDLISNIN RIVLELKGSE TTFMCEYADE TATIVEFLNR   120
WITFAQSIIS TLT                                                     133

SEQ ID NO: 34           moltype = AA   length = 133
FEATURE                 Location/Qualifiers
source                  1..133
                        mol_type = protein
                        organism = synthetic construct
SEQUENCE: 34
APTSSSTKKT QLQLEHLLLD LQMILNGINN YKNPKLTRML TFKFYMPKKA TELKHLQCLE    60
EELKPLEEVL NLAQSKNFHL RPRDLISNIN RIVLELKGSE TTFMCEYADE TATIVEFLNF   120
WITFAQSIIS TLT                                                     133

SEQ ID NO: 35           moltype = AA   length = 133
FEATURE                 Location/Qualifiers
source                  1..133
                        mol_type = protein
                        organism = synthetic construct
SEQUENCE: 35
APTSSSTKKT QLQEHLILD LQMILNGINN YKNPKLTRML TFKFYMPKKA TELKHLQCLE     60
EELKPLEEVL NLAQSKNFHL RPRDLISNLN RIILELKGSE TTFMCEYADE TATIVEFLNR   120
WITFAQSIIS TLT                                                     133

SEQ ID NO: 36           moltype = AA   length = 133
FEATURE                 Location/Qualifiers
source                  1..133
                        mol_type = protein
                        organism = synthetic construct
SEQUENCE: 36
APTSSSTKKT QLQLEELLLD LQMILNGINN YKNPKLTRML TFKFYMPKKA TELKHLQCLE    60
EELKPLEEVL NLAQSKNFHL RPRDLISNIN RIVLELKGSE TTFMCEYADE TATIVEFLNR   120
WITFAQSIIS TLT                                                     133

SEQ ID NO: 37           moltype = AA   length = 133
FEATURE                 Location/Qualifiers
source                  1..133
                        mol_type = protein
                        organism = synthetic construct
SEQUENCE: 37
APTSSSTKKT QLQLEELLLD LQMILNGINN VKNPKLTRML TFKFYMPKKA TELKHLQCLE    60
EELKPLEEVL NLLQSKNFQL RPRDLISNIN RIVLELKGSE TTFMCEYADE TATIVEFLNR   120
WITFAQSIIS TLT                                                     133

SEQ ID NO: 38           moltype = AA   length = 133
FEATURE                 Location/Qualifiers
source                  1..133
                        mol_type = protein
                        organism = synthetic construct
SEQUENCE: 38
APTSSSTKKT QLQLEELILD LQMILNGINN YKNPKLTRML TFKFYMPKKA TELKHLQCLE    60
EELKPLEEVL NLAQSKNFHL RPRDLISNLN RIILELKGSE TTFMCEYADE TATIVEFLNR   120
WITFAQSIIS TLT                                                     133

SEQ ID NO: 39           moltype = AA   length = 380
FEATURE                 Location/Qualifiers
source                  1..380
                        mol_type = protein
                        organism = synthetic construct
SEQUENCE: 39
APTSSSTKKT QLQLEELLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                              380

SEQ ID NO: 40           moltype = AA   length = 380
FEATURE                 Location/Qualifiers
source                  1..380
                        mol_type = protein
                        organism = synthetic construct
SEQUENCE: 40
APTSSSTKKT QLQLEELLLD LQMILNGINN VKNPKLTRML TFKFYMPKKA TELKHLQCLE    60
EELKPLEEVL NLLQSKNFQL RPRDLISNIN VIVLELKGSE TTFMCEYADE TATIVEFLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
```

```
VLHQDWLNGK EYKCKVSNKA LPAPIEKTIS KAKGQPREPQ VYTLPPSRDE LTKNQVSLTC    300
LVKGFYPSDI AVEWESNGQP ENNYKTTPPV LDSDGSFFLY SKLTVDKSRW QQGNVFSCSV    360
MHEALHNHYT QKSLSLSPGK                                                380

SEQ ID NO: 41            moltype = AA   length = 380
FEATURE                  Location/Qualifiers
source                   1..380
                         mol_type = protein
                         organism = synthetic construct
SEQUENCE: 41
APTSSSTKKT QLQLEELLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNF    120
WITFAQSIIS TLTGGGGSGG GGSGGGGSEP KSSDKTHTCP PCPAPELLGG PSVFLFPPKP    180
KDTLMISRTP EVTCVVVDVS HEDPEVKFNW YVDGVEVHNA KTKPREEQYG STYRVVSVLT    240
VLHQDWLNGK EYKCKVSNKA LPAPIEKTIS KAKGQPREPQ VYTLPPSRDE LTKNQVSLTC    300
LVKGFYPSDI AVEWESNGQP ENNYKTTPPV LDSDGSFFLY SKLTVDKSRW QQGNVFSCSV    360
MHEALHNHYT QKSLSLSPGK                                                380

SEQ ID NO: 42            moltype = AA   length = 380
FEATURE                  Location/Qualifiers
source                   1..380
                         mol_type = protein
                         organism = synthetic construct
SEQUENCE: 42
APTSSSTKKT QLQLEELILD LQMILNGINN YKNPKLTRML TFKFYMPKKA TELKHLQCLE     60
EELKPLEEVL NLAQSKNFHL RPRDLISNIN AIVLELKGSE TTFMCEYADE TATIVEWLNR    120
WITFAQSIIS TLTGGGGSGG GGSGGGGSEP KSSDKTHTCP PCPAPELLGG PSVFLFPPKP    180
KDTLMISRTP EVTCVVVDVS HEDPEVKFNW YVDGVEVHNA KTKPREEQYG STYRVVSVLT    240
VLHQDWLNGK EYKCKVSNKA LPAPIEKTIS KAKGQPREPQ VYTLPPSRDE LTKNQVSLTC    300
LVKGFYPSDI AVEWESNGQP ENNYKTTPPV LDSDGSFFLY SKLTVDKSRW QQGNVFSCSV    360
MHEALHNHYT QKSLSLSPGK                                                380

SEQ ID NO: 43            moltype = AA   length = 380
FEATURE                  Location/Qualifiers
source                   1..380
                         mol_type = protein
                         organism = synthetic construct
SEQUENCE: 43
APTSSSTKKT QLQLEELILD LQMILNGINN YKNPKLTRML TFKFYMPKKA TELKHLQCLE     60
EELKPLEEVL NLAQSKNFHL RPRDLISNLN VIILELKGSE TTFMCEYADE TATIVEFLNR    120
WITFAQSIIS TLTGGGGSGG GGSGGGGSEP KSSDKTHTCP PCPAPELLGG PSVFLFPPKP    180
KDTLMISRTP EVTCVVVDVS HEDPEVKFNW YVDGVEVHNA KTKPREEQYG STYRVVSVLT    240
VLHQDWLNGK EYKCKVSNKA LPAPIEKTIS KAKGQPREPQ VYTLPPSRDE LTKNQVSLTC    300
LVKGFYPSDI AVEWESNGQP ENNYKTTPPV LDSDGSFFLY SKLTVDKSRW QQGNVFSCSV    360
MHEALHNHYT QKSLSLSPGK                                                380

SEQ ID NO: 44            moltype = AA   length = 380
FEATURE                  Location/Qualifiers
source                   1..380
                         mol_type = protein
                         organism = synthetic construct
SEQUENCE: 44
APTSSSTKKT QLQLEELLLD LQMILNWINN YKNPKLTRML TFKFYMPKKA TELKHLQCLE     60
EELKPLEEVL NLAQSKNFHL RPRDLISNIN VIVLELKGSE TTFMCEYADE TATIVEFLNF    120
WITFAQSIIS TLTGGGGSGG GGSGGGGSEP KSSDKTHTCP PCPAPELLGG PSVFLFPPKP    180
KDTLMISRTP EVTCVVVDVS HEDPEVKFNW YVDGVEVHNA KTKPREEQYG STYRVVSVLT    240
VLHQDWLNGK EYKCKVSNKA LPAPIEKTIS KAKGQPREPQ VYTLPPSRDE LTKNQVSLTC    300
LVKGFYPSDI AVEWESNGQP ENNYKTTPPV LDSDGSFFLY SKLTVDKSRW QQGNVFSCSV    360
MHEALHNHYT QKSLSLSPGK                                                380

SEQ ID NO: 45            moltype = AA   length = 380
FEATURE                  Location/Qualifiers
source                   1..380
                         mol_type = protein
                         organism = synthetic construct
SEQUENCE: 45
APTSSSTKKT QLQLEELLLD LQMILNGINN YKNPKLTRML TFKFYMPKKA TELKHLQCLE     60
EELKPLEEVL NLAQSKNFHL RLRDLISNIN VIVLELKGSE TTFMCEYADE TATIVEFLNF    120
WITFAQSIIS TLTGGGGSGG GGSGGGGSEP KSSDKTHTCP PCPAPELLGG PSVFLFPPKP    180
KDTLMISRTP EVTCVVVDVS HEDPEVKFNW YVDGVEVHNA KTKPREEQYG STYRVVSVLT    240
VLHQDWLNGK EYKCKVSNKA LPAPIEKTIS KAKGQPREPQ VYTLPPSRDE LTKNQVSLTC    300
LVKGFYPSDI AVEWESNGQP ENNYKTTPPV LDSDGSFFLY SKLTVDKSRW QQGNVFSCSV    360
MHEALHNHYT QKSLSLSPGK                                                380

SEQ ID NO: 46            moltype = AA   length = 380
FEATURE                  Location/Qualifiers
source                   1..380
                         mol_type = protein
                         organism = synthetic construct
```

```
SEQUENCE: 46
APTSSSTKKT QLQLEHLLLA LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFAQSIIS TLTGGGGSGG GGSGGGGSEP KSSDKTHTCP PCPAPELLGG PSVFLFPPKP  180
KDTLMISRTP EVTCVVVDVS HEDPEVKFNW YVDGVEVHNA KTKPREEQYG STYRVVSVLT  240
VLHQDWLNGK EYKCKVSNKA LPAPIEKTIS KAKGQPREPQ VYTLPPSRDE LTKNQVSLTC  300
LVKGFYPSDI AVEWESNGQP ENNYKTTPPV LDSDGSFFLY SKLTVDKSRW QQGNVFSCSV  360
MHEALHNHYT QKSLSLSPGK                                              380

SEQ ID NO: 47            moltype = AA   length = 380
FEATURE                  Location/Qualifiers
source                   1..380
                         mol_type = protein
                         organism = synthetic construct
SEQUENCE: 47
APTSSSTKKT QLQLEHLLLA LQMILNGINN YKNPKLTRML TFKFYMPKKA TELKHLQCLE   60
EELKPLEEVL NLLQSKNFQL RPRDLISNIN VIVLELKGSE TTFMCEYADE TATIVEFLNR  120
WITFAQSIIS TLTGGGGSGG GGSGGGGSEP KSSDKTHTCP PCPAPELLGG PSVFLFPPKP  180
KDTLMISRTP EVTCVVVDVS HEDPEVKFNW YVDGVEVHNA KTKPREEQYG STYRVVSVLT  240
VLHQDWLNGK EYKCKVSNKA LPAPIEKTIS KAKGQPREPQ VYTLPPSRDE LTKNQVSLTC  300
LVKGFYPSDI AVEWESNGQP ENNYKTTPPV LDSDGSFFLY SKLTVDKSRW QQGNVFSCSV  360
MHEALHNHYT QKSLSLSPGK                                              380

SEQ ID NO: 48            moltype = AA   length = 380
FEATURE                  Location/Qualifiers
source                   1..380
                         mol_type = protein
                         organism = synthetic construct
SEQUENCE: 48
APTSSSTKKT QLQLEHLLLA LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNF  120
WITFAQSIIS TLTGGGGSGG GGSGGGGSEP KSSDKTHTCP PCPAPELLGG PSVFLFPPKP  180
KDTLMISRTP EVTCVVVDVS HEDPEVKFNW YVDGVEVHNA KTKPREEQYG STYRVVSVLT  240
VLHQDWLNGK EYKCKVSNKA LPAPIEKTIS KAKGQPREPQ VYTLPPSRDE LTKNQVSLTC  300
LVKGFYPSDI AVEWESNGQP ENNYKTTPPV LDSDGSFFLY SKLTVDKSRW QQGNVFSCSV  360
MHEALHNHYT QKSLSLSPGK                                              380

SEQ ID NO: 49            moltype = AA   length = 380
FEATURE                  Location/Qualifiers
source                   1..380
                         mol_type = protein
                         organism = synthetic construct
SEQUENCE: 49
APTSSSTKKT QLQLEHLLLD LQMILNGINN YKNPKLTRML TFKFYMPKKA TELKHLQCLE   60
EELKPLEEVL NLAQSKNFHL RPRDLISNIN RIVLELKGSE TTFMCEYADE TATIVEFLNR  120
WITFAQSIIS TLTGGGGSGG GGSGGGGSEP KSSDKTHTCP PCPAPELLGG PSVFLFPPKP  180
KDTLMISRTP EVTCVVVDVS HEDPEVKFNW YVDGVEVHNA KTKPREEQYG STYRVVSVLT  240
VLHQDWLNGK EYKCKVSNKA LPAPIEKTIS KAKGQPREPQ VYTLPPSRDE LTKNQVSLTC  300
LVKGFYPSDI AVEWESNGQP ENNYKTTPPV LDSDGSFFLY SKLTVDKSRW QQGNVFSCSV  360
MHEALHNHYT QKSLSLSPGK                                              380

SEQ ID NO: 50            moltype = AA   length = 380
FEATURE                  Location/Qualifiers
source                   1..380
                         mol_type = protein
                         organism = synthetic construct
SEQUENCE: 50
APTSSSTKKT QLQLEHLLLD LQMILNGINN YKNPKLTRML TFKFYMPKKA TELKHLQCLE   60
EELKPLEEVL NLLQSKNFQL RPRDLISNIN RIVLELKGSE TTFMCEYADE TATIVEFLNR  120
WITFAQSIIS TLTGGGGSGG GGSGGGGSEP KSSDKTHTCP PCPAPELLGG PSVFLFPPKP  180
KDTLMISRTP EVTCVVVDVS HEDPEVKFNW YVDGVEVHNA KTKPREEQYG STYRVVSVLT  240
VLHQDWLNGK EYKCKVSNKA LPAPIEKTIS KAKGQPREPQ VYTLPPSRDE LTKNQVSLTC  300
LVKGFYPSDI AVEWESNGQP ENNYKTTPPV LDSDGSFFLY SKLTVDKSRW QQGNVFSCSV  360
MHEALHNHYT QKSLSLSPGK                                              380

SEQ ID NO: 51            moltype = AA   length = 380
FEATURE                  Location/Qualifiers
source                   1..380
                         mol_type = protein
                         organism = synthetic construct
SEQUENCE: 51
APTSSSTKKT QLLLEHLLLD LQMILNGINN YKNPKLTRML TFKFYMPKKA TELKHLQCLE   60
EELKPLEEVL NLAQSKNFHL RPRDLISNIN RIVLELKGSE TTFMCEYADE TATIVEFLNR  120
WITFAQSIIS TLTGGGGSGG GGSGGGGSEP KSSDKTHTCP PCPAPELLGG PSVFLFPPKP  180
KDTLMISRTP EVTCVVVDVS HEDPEVKFNW YVDGVEVHNA KTKPREEQYG STYRVVSVLT  240
VLHQDWLNGK EYKCKVSNKA LPAPIEKTIS KAKGQPREPQ VYTLPPSRDE LTKNQVSLTC  300
LVKGFYPSDI AVEWESNGQP ENNYKTTPPV LDSDGSFFLY SKLTVDKSRW QQGNVFSCSV  360
MHEALHNHYT QKSLSLSPGK                                              380
```

```
SEQ ID NO: 52            moltype = AA   length = 380
FEATURE                  Location/Qualifiers
source                   1..380
                         mol_type = protein
                         organism = synthetic construct
SEQUENCE: 52
APTSSSTKKT QLQLEHLLLD LQMILNGINN YKNPKLTRML TFKFYMPKKA TELKHLQCLE    60
EELKPLEEVL NLAQSKNFHL RPRDLISNIN RIVLELKGSE TTFMCEYADE TATIVEFLNF   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                               380

SEQ ID NO: 53            moltype = AA   length = 380
FEATURE                  Location/Qualifiers
source                   1..380
                         mol_type = protein
                         organism = synthetic construct
SEQUENCE: 53
APTSSSTKKT QLQLEHLILD LQMILNGINN YKNPKLTRML TFKFYMPKKA TELKHLQCLE    60
EELKPLEEVL NLAQSKNFHL RPRDLISNLN RIILELKGSE TTFMCEYADE TATIVEFLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                               380

SEQ ID NO: 54            moltype = AA   length = 380
FEATURE                  Location/Qualifiers
source                   1..380
                         mol_type = protein
                         organism = synthetic construct
SEQUENCE: 54
APTSSSTKKT QLQLEELLLD LQMILNGINN YKNPKLTRML TFKFYMPKKA TELKHLQCLE    60
EELKPLEEVL NLAQSKNFHL RPRDLISNIN RIVLELKGSE TTFMCEYADE TATIVEFLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                               380

SEQ ID NO: 55            moltype = AA   length = 380
FEATURE                  Location/Qualifiers
source                   1..380
                         mol_type = protein
                         organism = synthetic construct
SEQUENCE: 55
APTSSSTKKT QLQLEELLLD LQMILNGINN VKNPKLTRML TFKFYMPKKA TELKHLQCLE    60
EELKPLEEVL NLLQSKNFQL RPRDLISNIN RIVLELKGSE TTFMCEYADE TATIVEFLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                               380

SEQ ID NO: 56            moltype = AA   length = 380
FEATURE                  Location/Qualifiers
source                   1..380
                         mol_type = protein
                         organism = synthetic construct
SEQUENCE: 56
APTSSSTKKT QLQLEELILD LQMILNGINN YKNPKLTRML TFKFYMPKKA TELKHLQCLE    60
EELKPLEEVL NLAQSKNFHL RPRDLISNLN RIILELKGSE TTFMCEYADE TATIVEFLNR   120
WITFAQSIIS TLTGGGGSGG GGSGGGGSEP KSSDKTHTCP PCPAPELLGG PSVFLFPPKP   180
KDTLMISRTP EVTCVVVDVS HEDPEVKFNW YVDGVEVHNA KTKPREEQYG STYRVVSVLT   240
VLHQDWLNGK EYKCKVSNKA LPAPIEKTIS KAKGQPREPQ VYTLPPSRDE LTKNQVSLTC   300
LVKGFYPSDI AVEWESNGQP ENNYKTTPPV LDSDGSFFLY SKLTVDKSRW QQGNVFSCSV   360
MHEALHNHYT QKSLSLSPGK                                               380

SEQ ID NO: 57            moltype = AA   length = 272
FEATURE                  Location/Qualifiers
source                   1..272
                         mol_type = protein
                         organism = Homo sapiens
SEQUENCE: 57
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS   120
LPGHCREPPP WENEATERIY HFVVGQMVYY QCVQGYRALH RGPAESVCKM THGKTRWTQP   180
```

```
QLICTGEMET SQFPGEEKPQ ASPEGRPESE TSCLVTTTDF QIQTEMAATM ETSIFTTEYQ  240
VAVAGCVFLL ISVLLLSGLT WQRRQRKSRR TI                              272

SEQ ID NO: 58          moltype = AA  length = 551
FEATURE                Location/Qualifiers
source                 1..551
                       mol_type = protein
                       organism = Homo sapiens
SEQUENCE: 58
MAAPALSWRL PLLILLLPLA TSWASAAVNG TSQFTCFYNS RANISCVWSQ DGALQDTSCQ  60
VHAWPDRRRW NQTCELLPVS QASWACNLIL GAPDSQKLTT VDIVTLRVLC REGVRWRVMA  120
IQDFKPFENL RLMAPISLQV VHVETHRCNI SWEISQASHY FERHLEFEAR TLSPGHTWEE  180
APLLTLKQKQ EWICLETLTP DTQYEFQVRV KPLQGEFTTW SPWSQPLAFR TKPAALGKDT  240
IPWLGHLLVG LSGAFGFIIL VYLLINCRNT GPWLKKVLKC NTPDPSKFFS QLSSEHGGDV  300
QKWLSSPFPS SSFSPGGLAP EISPLEVLER DKVTQLLLQQ DKVPEPASLS SNHSLTSCFT  360
NQGYFFFHLP DALEIEACQV YFTYDPYSEE DPDEGVAGAP TGSSPQPLQP LSGEDDAYCT  420
FPSRDDLLLF SPSLLGGPSP PSTAPGGSGA GEERMPPSLQ ERVPRDWDPQ PLGPPTPGVP  480
DLVDFQPPPE LVLREAGEEV PDAGPREGVS FPWSRPPGQG EFRALNARLP LNTDAYLSLQ  540
ELQGQDPTHL V                                                     551

SEQ ID NO: 59          moltype = AA  length = 369
FEATURE                Location/Qualifiers
source                 1..369
                       mol_type = protein
                       organism = Homo sapiens
SEQUENCE: 59
MLKPSLPFTS LLFLQLPLLG VGLNTTILTP NGNEDTTADF FLTTMPTDSL SVSTLPLPEV  60
QCFVFNVEYM NCTWNSSSEP QPTNLTLHYW YKNSDNDKVQ KCSHYLFSEE ITSGCQLQKK  120
EIHLYQTFVV QLQDPREPRR QATQMLKLQN LVIPWAPENL TLHKLSESQL ELNWNNRFLN  180
HCLEHLVQYR TDWDHSWTEQ SVDYRHKFSL PSVDGQKRYT FRVRSRFNPL CGSAQHWSEW  240
SHPIHWGSNT SKENPFLFAL EAVVISVGSM GLIISLLCVY FWLERTMPRI PTLKNLEDLV  300
TEYHGNFSAW SGVSKGLAES LQPDYSERLC LVSEIPPKGG ALGEGPGASP CNQHSPYWAP  360
PCYTLKPET                                                        369

SEQ ID NO: 60          moltype = AA  length = 133
FEATURE                Location/Qualifiers
SITE                   125
                       note = misc_feature - Xaa represents Cys, Ser, Ala or Val
source                 1..133
                       mol_type = protein
                       organism = synthetic construct
SEQUENCE: 60
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFXQSIIS TLT                                                   133

SEQ ID NO: 61          moltype = AA  length = 368
FEATURE                Location/Qualifiers
source                 1..368
                       mol_type = protein
                       organism = synthetic construct
SEQUENCE: 61
PKSSDKTHTC PPCPAPELLG GPSVFLFPPK PKDTLMISRT PEVTCVVVDV SHEDPEVKFN  60
WYVDGVEVHN AKTKPCEEQY GSTYRCVSVL TVLHQDWLNG KEYKCKVSNK ALPAPIEKTI  120
SKAKGQPREP QVYTLPPSRD ELTKNQVSLT CLVKGFYPSD IAVEWESNGQ PENNYKTTPP  180
VLDSDGSFFL YSKLTVDKSR WQQGNVFSCS VMHEALHNHY TQKSLSLSPG GGGGSAPTSS  240
STKKTQLQLE HLLLDLQMIL NGINNYKNPK LTRMLTFKFY MPKKATELKH LQCLEEELKP  300
LEEVLNLAQS KNFHLRPRDL ISNINKIVLE LKGSETTFMC EYADETATIV EFLNRWITFA  360
QSIISTLT                                                         368
```

What is claimed is:

1. An IL-2 mutant comprising mutations Y31V, A73L, H79Q and V91R compared to wild-type IL-2; wherein the wild-type IL-2 has an amino acid sequence as shown in SEQ ID NO: 1.

2. The IL-2 mutant according to claim 1, wherein the IL-2 mutant comprises the amino acid sequence as shown in SEQ ID NO: 32.

3. The IL-2 mutant according to claim 1, wherein the IL-2 mutant has a Tm value higher than that of the wild-type IL-2.

4. The IL-2 mutant according to claim 1, wherein the IL-2 mutant has a reduced binding ability to IL-2Rβγ subunit complex compared to the wild-type IL-2.

5. The IL-2 mutant according to claim 4, wherein the binding ability to IL-2Rβγ subunit complex/binding ability to IL-2 αβγ subunit complex decreases compared to wild-type IL-2.

6. The IL-2 mutant according to claim 1, wherein the mutant has a reduced stimulation ability to non-regulatory T cells or NK (natural killer) cells compared to the wild-type IL-2; the stimulation is from intracellular STAT5 phosphorylation or cell proliferation.

7. A fusion protein comprising a first polypeptide and a second polypeptide, wherein the first polypeptide is the IL-2 mutant according to claim 1, and wherein the second polypeptide is an Fc.

8. The fusion protein according to claim 7, wherein the Fc is a human IgG1 Fc.

9. The fusion protein according to claim 8, wherein the human IgG1 Fc comprises mutations of C220S and N297G.

10. The fusion protein according to claim 7, wherein C-terminus of the first polypeptide is linked to N-terminus of the second polypeptide with a linker.

11. The fusion protein according to claim 10, wherein the linker is $(G_4S)_3$.

12. The fusion protein according to claim 7, wherein the fusion protein comprises an amino acid sequence as shown in SEQ ID NO: 50.

13. A pharmaceutical composition comprising the IL-2 mutant of claim 1 and a pharmaceutically acceptable carrier, diluent or adjuvant, wherein the pharmaceutical composition is formulated for injection.

14. The pharmaceutical composition according to claim 13, wherein the pharmaceutical composition is formulated for intravenous or subcutaneous injection.

15. A pharmaceutical composition comprising the fusion protein of claim 7 and a pharmaceutically acceptable carrier, diluent or adjuvant, wherein the pharmaceutical composition is formulated for injection.

16. The pharmaceutical composition according to claim 15, wherein the pharmaceutical composition is formulated for intravenous or subcutaneous injection.

* * * * *